US011638764B2

(12) United States Patent
Agnew

(10) Patent No.: US 11,638,764 B2
(45) Date of Patent: May 2, 2023

(54) THERANOSTIC CAPTURE AGENTS, COMPOSITIONS, AND METHODS OF USING AND MAKING

(71) Applicant: Indi Molecular, Inc., Culver City, CA (US)

(72) Inventor: Heather Agnew, Culver City, CA (US)

(73) Assignee: INDI MOLECULAR, INC., Culver City, CA (US)

( * ) Notice: Subject to any disclaimer, the term of this patent is extended or adjusted under 35 U.S.C. 154(b) by 0 days.

(21) Appl. No.: 16/678,842

(22) Filed: Nov. 8, 2019

(65) Prior Publication Data

US 2020/0147244 A1    May 14, 2020

Related U.S. Application Data

(60) Provisional application No. 62/757,706, filed on Nov. 8, 2018.

(51) Int. Cl.
  *A61K 51/04*    (2006.01)
  *G01N 33/574*   (2006.01)

(52) U.S. Cl.
  CPC ............ *A61K 51/0497* (2013.01); *G01N 33/57434* (2013.01)

(58) Field of Classification Search
  CPC .... A61K 2123/00; A61K 51/00; A61K 51/04; A61K 51/0497; A61K 51/08; A61K 51/088; A61K 33/00; A61K 33/24; G01N 33/57434; G01N 33/532; G01N 33/574; G01N 33/531; C07K 5/1021; C07K 5/1016; C12N 9/485; C12Y 304/17201
  USPC .......... 424/1.11, 1.49, 1.65, 1.69, 1.81, 1.85, 424/1.89, 9.1, 9.2, 9.3, 9.4, 9.5, 9.6; 514/1, 1.1, 19.2, 19.3, 19.4, 19.5, 21.1, 514/21.5, 21.6, 21.7, 21.8, 21.9; 530/300; 534/7, 10–16
  See application file for complete search history.

(56) References Cited

U.S. PATENT DOCUMENTS

| | | |
|---|---|---|
| 4,899,755 A | 2/1990 | Lauffer |
| 5,021,556 A | 6/1991 | Srinivasan |
| 5,075,099 A | 12/1991 | Srinivasan |
| 5,118,797 A | 6/1992 | Jurisson |
| 5,183,653 A | 2/1993 | Linder |
| 5,364,613 A | 11/1994 | Sieving |
| 5,367,080 A | 11/1994 | Toner |
| 5,387,409 A | 2/1995 | Nunn |
| 5,474,756 A | 12/1995 | Tweedle |
| 5,608,110 A | 3/1997 | Ramalingam |
| 5,656,254 A | 8/1997 | Ramalingam |
| 5,662,885 A | 9/1997 | Pollak |
| 5,665,329 A | 9/1997 | Ramalingam |
| 5,688,487 A | 11/1997 | Linder |
| 5,720,934 A | 2/1998 | Dean |
| 5,780,006 A | 7/1998 | Pollak |
| 5,846,519 A | 12/1998 | Tweedle |
| 5,849,261 A | 12/1998 | Dean |
| 5,879,658 A | 3/1999 | Dean |
| 5,886,142 A | 3/1999 | Thakur |
| 5,976,495 A | 11/1999 | Pollak |
| 6,093,382 A | 7/2000 | Wedeking |
| 6,143,274 A | 11/2000 | Tweedle |
| 8,710,180 B2 * | 4/2014 | Pitram .................... A61P 35/00 530/300 |
| 8,841,083 B2 * | 9/2014 | Heath ............... G01N 33/57434 435/7.4 |
| 8,906,830 B2 * | 12/2014 | Agnew ................... A61P 43/00 506/9 |
| 9,188,584 B2 * | 11/2015 | Agnew ................ C07D 249/04 |
| 9,221,889 B2 * | 12/2015 | Pitram ................. G01N 33/574 |
| 9,913,875 B2 * | 3/2018 | Farrow .................... C07K 7/08 |
| 10,598,671 B2 * | 3/2020 | Heath ....................... C07K 7/64 |
| 11,007,245 B2 * | 5/2021 | Farrow ................ C07B 59/008 |
| 2010/0009896 A1 | 1/2010 | Agnew |

FOREIGN PATENT DOCUMENTS

| | | |
|---|---|---|
| WO | 1986006605 | 11/1986 |
| WO | 1991003200 | 3/1991 |
| WO | 1995003280 | 2/1995 |
| WO | 1995006633 | 3/1995 |
| WO | 1995028179 | 10/1995 |
| WO | 1995028967 | 11/1995 |
| WO | 1996003427 | 2/1996 |
| WO | 1996023526 | 8/1996 |
| WO | 1997036619 | 10/1997 |
| WO | 1998018496 | 5/1998 |
| WO | 1998018497 | 5/1998 |
| WO | 1998046612 | 10/1998 |
| WO | 9852618 | 11/1998 |

(Continued)

OTHER PUBLICATIONS

Fisher et al, RSC Adv., vol. 5, pp. 96194-96200 (Year: 2015).*
Agnew, et al., "Iterative In Situ Click Chemistry Creates Antibody☐like Protein☐Capture Agents", Angew. Chemie Int. Ed., 48(27):4944-4948 (2009).
Alexander, et al., "Intracranial black☐blood MR angiography with hi gh☐resolution 3D fast spin echo", Magn. Reson. Med., 40: 298-310 (1998).
Altschul, et al., "Gapped BLAST and PSI-BLAST: a new generation of protein database search programs", Nucleic Acids Res. 25:3389-402 (1997).

(Continued)

Primary Examiner — D. L. Jones
(74) Attorney, Agent, or Firm — Pabst Patent Group LLP

(57) ABSTRACT

Disclosed are compounds, compositions, and methods involving theranostic capture agent for a target where the capture agent is (a) a precursor that can be loaded with a detectable moiety, a therapeutic moiety, or both, (b) loaded with a detectable moiety, (c) loaded with a therapeutic moiety, or (d) loaded with both a detectable moiety and a therapeutic moiety. Also disclosed are stable peptide-based PSMA capture agents and methods of use as detection agents.

71 Claims, 9 Drawing Sheets
Specification includes a Sequence Listing.

(56) References Cited

FOREIGN PATENT DOCUMENTS

| WO | 1999017809 | 4/1999 |
|---|---|---|
| WO | 2009155420 | 12/2009 |
| WO | 2010135431 | 11/2010 |
| WO | 2012106671 | 8/2012 |
| WO | 2013009869 | 1/2013 |
| WO | 2013033561 | 3/2013 |
| WO | 2014074907 | 5/2014 |
| WO | 2017011769 | 1/2017 |
| WO | 2017176769 | 10/2017 |
| WO | 2018200551 | 11/2018 |

OTHER PUBLICATIONS

Benesova, et al., "Preclinical Evaluation of a Tailor-Made DOTA-Conjugated PSMA Inhibitor with Optimized Linker Moiety for Imaging and Endoradiotherapy of Prostate Cancer", JNM, 56(6):914-20 (2015).

Cardinale, et al., "Preclinical Evaluation of 18F-PSMA-1007, a New Prostate-Specific Membrane Antigen Ligand for Prostate Cancer Imaging", JNM, 58(3):425-431 (2017).

Cho, et al., "Biodistribution, Tumor Detection, and Radiation Dosimetry of 18F-DCFBC, a Low-Molecular-Weight Inhibitor of Prostate-Specific Membrane Antigen, in Patients with Metastatic Prostate Cancer", JNM, 53:1883-1891 (2012).

Claverie, et al., "Information enhancement methods for large scale sequence analysis", Claverie Comput. Chem. 17:191-201 (1993).

Das, et al., "A General Synthetic Approach for Designing Epitope Targeted Macrocyclic Peptide Ligands", Angew. Chemie Int. Ed., 54 (45), 13219-13224 (2015).

Edelman, et al., "Extracranial carotid arteries: evaluation with 'black blood' MR angiography", Radiology, 177: 45-50 (1990).

Eder, et al., "68Ga-Complex Lipophilicity and the Targeting Property of a Urea-Based PSMA Inhibitor for PET Imaging", Biconjugate Chem., 23(4):688-97 (2012).

Eiber, et al., "Prostate-Specific Membrane Antigen Ligands for Imaging and Therapy", The Journal of Nuclear Medicine, 58(9):67S-76S (2017).

Farrow, et al., "Epitope-Targeting of Tertiary Protein Structure Enables Target-Guided Synthesis of a Potent in Cell Inhibitor of Botulinum Neurotoxin", Angew. Chemie Int. Ed. , 54 (24), 7114-7119 (2015).

Giesel, et al., "F-18 labelled PSMA-1007: biodistribution, radiation dosimetry and histopathological validation of tumor lesions in prostate cancer patients", EJNMMI, 44(4):678-688 (2016).

Goodrich, et al., "A Quantitative Study of ramped Radio Frequency, Magnetization Transfer, and Slab Thickness in Three-Dimensional Time-of-Flight Magnetic Resonance Angiogrpahy in a Patient Population", Invest. Radia, 31: 323-32 (1996).

International Search Report for corresponding PCT application PCT/US2019/060571 dated Apr. 30, 2020.

Iwata, et al., "Anew, convenient method for the preparation of 4-[18F]fluorobenzyl halides", Appl Radia Isot, 52:87-92 (2000).

Kopka, et al., "Glu-Ureido-Based Inhibitors of Prostate-Specific Membrane Antigen: Lessons Learned During the Development of a Novel Class of Low-Molecular-Weight Theranostic Radiotracers", JNM, 58(Suppl 2): 17S-26S (2017).

Liu, et al., "99mTc-Labeled Small Peptides as Diagnostic Radiopharmaceuticals", Chem. Rev. 99:2235-2268 (1999).

Maurer, et al., "Current use of PSMA-PET in prostate cancer management", Nat. Rev. Urol., 12:226-235 (2016).

Myers, et al., "Optimal alignments in linear space", Computer Applic. Biol. Sci. 4(1):11-17 (1988).

Poethko, et al., "Two-step methodology for high-yield routine radiohalogenation of peptides: (18)F-labeled RGD and octreotide analogs", J Nucl Med, 45:892-902 (2004).

Schottelius, et al., "First (18)F-labeled tracer suitable for routine clinical imaging of sst receptor-expressing tumors using positron emission tomography", Clin Can Res, 10:3593-3606 (2004).

Szabo, at al., "Initial Evaluation of [18F]DCFPyL for Prostate Specific Membrane Antigen (PSMA)-Targeted PET Imaging of Prostate Cancer", Mol. Imaging Biol., 17(4):565-574 (2015).

Tao, et al., "Expression, purification and identification of an immunogenic fragment in the ectodomain of prostate-specific membrane antigen", Experimental and Therapeutic Medicine, 11:747-752 (2016).

Todorova, et al., "Biochemical nature and Mapping of PSMA Epitopes Recognized bu Human Antibodies Induced after Immunization with Gene-based Vaccines", Anticancer Research, 25:4727-4732 (2005).

Wang, et al., "Radioligand Therapy of Prostate Cancer with a Long-Lasting Prostate-Specific Membrane Antigen Targeting Agent Y-DOTA-EB-MCG", Bioconjug. Chem., 29(7):2309-2315 (2018).

Weineisen, et al., "68Ga- and 177Lu-Labeled PSMA I&T: Optimization of a PSMA-Targeted Theranostic Concept and First Proof-of-Concept Human Studies", JNM, 56(8):1169-76 (2015).

Wilson, et al., "Reductive amination of [18F]fluorobenzaldehydes: Radiosyntheses of [2□18F]□ and [4□18F]fluorodexetimides", J Labeled Compounds and Radiopharmaceuticals, 28(10):1189-99 (1990).

Wooton, et al., "Statistics of Local Complexity in Amino Acid Sequences and Sequence Databases", Comput. Chem. 17(2):149-63 (1993).

\* cited by examiner

THERANOSTIC CAPTURE AGENTS, COMPOSITIONS, AND METHODS OF USING AND MAKING

CROSS-REFERENCE TO RELATED APPLICATIONS

This application claims benefit of U.S. Provisional Application No. 62/757,706, filed Nov. 8, 2018. Application No. 62/757,706, filed Nov. 8, 2018, is hereby incorporated herein by reference in its entirety.

REFERENCE TO SEQUENCE LISTING

The Sequence Listing submitted Nov. 8, 2019, as a text file named "INDI_101_ST25.txt," created on Nov. 8, 2019, and having a size of 19,299 bytes is hereby incorporated by reference pursuant to 37 C.F.R. § 1.52(e)(5).

FIELD OF THE INVENTION

The disclosed invention is generally in the field of capture agents and specifically in the area of PSMA capture agents and methods of making and using such capture agents.

BACKGROUND OF THE INVENTION

Efforts to evaluate and discover diagnostic and therapeutic markers for prostate cancer led to the discovery of prostate-specific membrane antigen (PSMA), a transmembrane protein expressed in all types of prostatic tissue, remains a useful diagnostic and possibly therapeutic target. PSMA is a type II membrane protein originally characterized by the murine monoclonal antibody (mAb) 7E11-05.3 and is expressed in all forms of prostate tissue, including carcinoma. The PSMA protein has a unique 3-part structure: a 19-amino-acid internal portion, a 24-amino-acid transmembrane portion, and a 707-amino-acid external portion. The PSMA gene is located on the short arm of chromosome 11 in a region that is not commonly deleted in prostate cancer.

PSMA has known enzymatic activities and acts as a glutamate-preferring carboxypeptidase. The impact of these enzymatic functions on human prostate tissue and perhaps elsewhere, however, remains unclear. PSMA has an internalization signal that allows internalization of the protein on the cell surface into an endosomal compartment.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

BRIEF SUMMARY OF THE INVENTION

Disclosed are compounds, compositions, and methods involving theranostic capture agent for a target where the capture agent is (a) a precursor that can be loaded with a detectable moiety, a therapeutic moiety, or both, (b) loaded with a detectable moiety, (c) loaded with a therapeutic moiety, or (d) loaded with both a detectable moiety and a therapeutic moiety. Generally, the capture agent comprises two or more ligands covalently linked to each other, where the ligands specifically bind to one of two or more distinct epitopes of a target that are in different locations on the target. In some forms, the capture agent comprises two or more ligands covalently linked to each other, where the ligands specifically bind to one of two or more distinct epitopes of a target that are in different locations on the target, and a detectable moiety, a therapeutic moiety, or both.

Also disclosed are compositions and methods that involve capture agents that bind PSMA. For example, disclosed are methods of using the disclosed capture agents to detect PSMA. For example, the present disclosure relates to chemically synthesized capture agents (called protein-catalyzed capture agents, or PCC Agents) that are designed to bind to and/or detect prostate specific membrane antigen (PSMA), methods for making said capture agents using iterative in situ click chemistry, methods for using said capture agents to detect PSMA, and assays employing said methods.

Also disclosed are stable, synthetic capture agents that specifically binds PSMA, wherein the capture agent comprises a ligand having affinity for an epitope on PSMA.

In some forms, the epitope comprises the amino acid sequence RTEDFFKLERDMK (SEQ ID NO:2) or EYAYRRGIAEAVGLPSI (SEQ ID NO:1). In some forms, the epitope comprises the amino acid sequence RTEDFFKLERDMK (SEQ ID NO:2), EYAYRRGIAEAVGLPSI (SEQ ID NO:1), TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), or GSAPPDSSWRGSLKVPYNVGPGF (SEQ ID NO:15). In some forms, the epitope comprises the amino acid sequence TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), or GSAPPDSSWRGSLKVPYNVGPGF (SEQ ID NO:15).

In some forms, the first epitope comprises the amino acid sequence RTEDFFKLERDMK (SEQ ID NO:2) or EYAYRRGIAEAVGLPSI (SEQ ID NO:1). In some forms, the first epitope comprises the amino acid sequence RTEDFFKLERDMK (SEQ ID NO:2), EYAYRRGIAEAVGLPSI (SEQ ID NO:1), TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), or GSAPPDSSWRGSLKVPYNVGPGF (SEQ ID NO:15). In some forms, the first epitope comprises the amino acid sequence TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), or GSAPPDSSWRGSLKVPYNVGPGF (SEQ ID NO:15).

In some forms, the second epitope comprises the amino acid sequence RTEDFFKLERDMK (SEQ ID NO:2) or EYAYRRGIAEAVGLPSI (SEQ ID NO:1). In some forms, the second epitope comprises the amino acid sequence RTEDFFKLERDMK (SEQ ID NO:2), EYAYRRGIAEAVGLPSI (SEQ ID NO:1), TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), or GSAPPDSSWRGSLKVPYNVGPGF (SEQ ID NO:15). In some forms, the second epitope comprises the amino acid sequence TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), or GSAPPDSSWRGSLKVPYNVGPGF (SEQ ID NO:15).

In some forms, the second epitope comprises the amino acid sequence EYAYRRGIAEAVGLPSI (SEQ ID NO:1). In some forms, the second epitope comprises the amino acid sequence TKKSPSPEFSGMP (SEQ ID NO:11). In some forms, the second epitope comprises the amino acid sequence YTKNWETNKFSG (SEQ ID NO:13). In some forms, the second epitope comprises the amino acid sequence RTEDFFKLERDMK (SEQ ID NO:2). In some forms, the second epitope comprises the amino acid sequence TKKSPSPEFSGMPRISKLG (SEQ ID NO:12), PADYFAPGVKSYPDGWNLPG (SEQ ID NO:14), or GSAPPDSSWRGSLKVPYNVGPGF (SEQ ID NO:15). In some forms, the second epitope comprises the amino acid sequence TKKSPSPEFSGMPRISKLG (SEQ ID NO:12). In some forms, the second epitope comprises the amino acid sequence PADYFAPGVKSYPDGWNLPG (SEQ ID NO:14). In some forms, the second epitope comprises the amino acid sequence GSAPPDSSWRGSLKVPYNVGPGF (SEQ ID NO:15).

Peptide library screening can be performed with one or more different epitopes. When two or more different epitopes are used, some or all of the different epitopes can be used sequentially in the screening (referred to as sequential screening) (screening, for example, only the hit peptides from a prior screen using a different epitope in a subsequence screen), in combination (referred to as multi-ligand screening) (screening, for example, using two or more different epitopes in the same screen), or a combination of both sequential and combination screening. In some forms, the epitopes used can be two epitopes where each epitope is selected from the group consisting of amino acid sequences comprising RTEDFFKLERDMK (SEQ ID NO:2) and EYAYRRGIAEAVGLPSI (SEQ ID NO:1). In some forms, the epitopes used can be two or more epitopes where each epitope is selected from the group consisting of amino acid sequences comprising RTEDFFKLERDMK (SEQ ID NO:2), EYAYRRGIAEAVGLPSI (SEQ ID NO:1), TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15). In some forms, the epitopes used can be two or more epitopes where each epitope is selected from the group consisting of amino acid sequences comprising TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15).

In some forms, the epitopes used can be two or more epitopes where one or both of the epitopes is selected from the group consisting of amino acid sequences comprising RTEDFFKLERDMK (SEQ ID NO:2) and EYAYRRGIAEAVGLPSI (SEQ ID NO:1). In some forms, the epitopes used can be two or more epitopes where one or more of the epitopes is selected from the group consisting of amino acid sequences comprising RTEDFFKLERDMK (SEQ ID NO:2), EYAYRRGIAEAVGLPSI (SEQ ID NO:1), TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15). In some forms, the epitopes used can be two or more epitopes where one or more of the epitopes is selected from the group consisting of amino acid sequences comprising TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15).

In some forms, the screen uses two first epitopes where both of the first epitopes are selected from the group consisting of amino acid sequences comprising RTEDFFKLERDMK (SEQ ID NO:2) and EYAYRRGIAEAVGLPSI (SEQ ID NO:1). In some forms, the screen uses two or more first epitopes where each of the first epitopes comprises the amino acid sequence RTEDFFKLERDMK (SEQ ID NO:2), EYAYRRGIAEAVGLPSI (SEQ ID NO:1), TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15). In some forms, the screen uses two or more first epitopes where each of the first epitopes comprises the amino acid sequence TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15).

In some forms, the screen uses two second epitopes where both of the second epitopes are selected from the group consisting of amino acid sequences comprising RTEDFFKLERDMK (SEQ ID NO:2) and EYAYRRGIAEAVGLPSI (SEQ ID NO:1). In some forms, the screen uses two or more second epitopes where each of the second epitopes RTEDFFKLERDMK (SEQ ID NO:2), EYAYRRGIAEAVGLPSI (SEQ ID NO:1), TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15). In some forms, the screen uses two or more second epitopes where each of the second epitopes TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15).

In some forms, the screen uses two first epitopes where one or both of the first epitopes are selected from the group consisting of amino acid sequences comprising RTEDFFKLERDMK (SEQ ID NO:2) and EYAYRRGIAEAVGLPSI (SEQ ID NO:1). In some forms, the screen uses two or more first epitopes where one or more of the first epitopes comprises the amino acid sequence RTEDFFKLERDMK (SEQ ID NO:2), EYAYRRGIAEAVGLPSI (SEQ ID NO:1), TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15). In some forms, the screen uses two or more first epitopes where one or more of the first epitopes comprises the amino acid sequence TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15).

In some forms, the screen uses two second epitopes where one or both of the second epitopes are selected from the group consisting of amino acid sequences comprising RTEDFFKLERDMK (SEQ ID NO:2) and EYAYRRGIAEAVGLPSI (SEQ ID NO:1). In some forms, the screen uses two or more first epitopes where one or more of the first epitopes comprises the amino acid sequence RTEDFFKLERDMK (SEQ ID NO:2), EYAYRRGIAEAVGLPSI (SEQ ID NO:1), TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15). In some forms, the screen uses two or more first epitopes where one or more of the first epitopes comprises the amino acid sequence TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15).

In some forms, the ligand comprises an amino acid sequence 80-100% identical to an amino acid sequence selected from the group consisting of: ert, revry (SEQ ID NO:3), rdlhw (SEQ ID NO:4), drlhw (SEQ ID NO:5), lpwtr (SEQ ID NO:6), tfnkn (SEQ ID NO:7), wlsGk (SEQ ID NO:8), srdwp (SEQ ID NO:9), and hreww (SEQ ID NO:10).

In some forms, the ligand comprises an amino acid sequence 80-100% identical to an amino acid sequence selected from the group consisting of: revry (SEQ ID NO:3), hreww (SEQ ID NO:10), rdlhw (SEQ ID NO:4), drlhw (SEQ ID NO:5), ert, lpwtr (SEQ ID NO:6), tfnkn (SEQ ID NO:7), wlsGk (SEQ ID NO:8), srdwp (SEQ ID NO:9), lfkhh (SEQ ID NO:16), fGyvd (SEQ ID NO:17), ernta (SEQ ID NO:18), hnwlG (SEQ ID NO:19), wende (SEQ ID NO:20), lnhGt (SEQ ID NO:21), ehtye (SEQ ID NO:22), dwpve (SEQ ID NO:23), kwtsd (SEQ ID NO:24), svand (SEQ ID NO:25), and dntwp (SEQ ID NO:26).

In some forms, the ligand comprises an amino acid sequence 80-100% identical to an amino acid sequence selected from the group consisting of: lfkhh (SEQ ID NO:16), fGyvd (SEQ ID NO:17), ernta (SEQ ID NO:18), hnwlG (SEQ ID NO:19), wende (SEQ ID NO:20), lnhGt (SEQ ID NO:21), ehtye (SEQ ID NO:22), dwpve (SEQ ID NO:23), kwtsd (SEQ ID NO:24), svand (SEQ ID NO:25), and dntwp (SEQ ID NO:26).

In some forms, the ligand comprises an amino acid sequence 80-100% identical to an amino acid sequence selected from the group consisting of: pkvrd (SEQ ID NO:27), frvkd (SEQ ID NO:28), lynre (SEQ ID NO:29), Gydfp (SEQ ID NO:30), sfkyk (SEQ ID NO:31), dyksk (SEQ ID NO:32), wksl (SEQ ID NO:33), rkatp (SEQ ID NO:34), Grkpf (SEQ ID NO:35), kwndd (SEQ ID NO:36), eldd (SEQ ID NO:37), anGsw (SEQ ID NO:38), tkGne (SEQ ID NO:39), plntd (SEQ ID NO:40), kvetd (SEQ ID NO:41), neGfd (SEQ ID NO:42), ekfld (SEQ ID NO:43), dkkaw (SEQ ID NO:44), veyGn (SEQ ID NO:45), and eyprh (SEQ ID NO:46).

In some forms, the ligand comprises an amino acid sequence 80-100% identical to an amino acid sequence selected from the group consisting of: revry (SEQ ID NO:3), hreww (SEQ ID NO:10), rdlhw (SEQ ID NO:4), drlhw (SEQ ID NO:5), ert, lpwtr (SEQ ID NO:6), tfnkn (SEQ ID NO:7), wlsGk (SEQ ID NO:8), srdwp (SEQ ID NO:9), lfkhh (SEQ ID NO:16), fGyvd (SEQ ID NO:17), ernta (SEQ ID NO:18), hnwlG (SEQ ID NO:19), wende (SEQ ID NO:20), lnhGt (SEQ ID NO:21), ehtye (SEQ ID NO:22), dwpve (SEQ ID NO:23), kwtsd (SEQ ID NO:24), svand (SEQ ID NO:25), dntwp (SEQ ID NO:26), pkvrd (SEQ ID NO:27), frvkd (SEQ ID NO:28), lynre (SEQ ID NO:29), Gydfp (SEQ ID NO:30), sfkyk (SEQ ID NO:31), dyksk (SEQ ID NO:32), wksl (SEQ ID NO:33), rkatp (SEQ ID NO:34), Grkpf (SEQ ID NO:35), kwndd (SEQ ID NO:36), eldd (SEQ ID NO:37), anGsw (SEQ ID NO:38), tkGne (SEQ ID NO:39), plntd (SEQ ID NO:40), kvetd (SEQ ID NO:41), neGfd (SEQ ID NO:42), ekfld (SEQ ID NO:43), dkkaw (SEQ ID NO:44), veyGn (SEQ ID NO:45), and eyprh (SEQ ID NO:46).

In some forms, the ligand comprises an amino acid sequence selected from the group consisting of: revry (SEQ ID NO:3), hreww (SEQ ID NO:10), rdlhw (SEQ ID NO:4), drlhw (SEQ ID NO:5), ert, lpwtr (SEQ ID NO:6), tfnkn (SEQ ID NO:7), wlsGk (SEQ ID NO:8), srdwp (SEQ ID NO:9), lfkhh (SEQ ID NO:16), fGyvd (SEQ ID NO:17), ernta (SEQ ID NO:18), hnwlG (SEQ ID NO:19), wende (SEQ ID NO:20), lnhGt (SEQ ID NO:21), ehtye (SEQ ID NO:22), dwpve (SEQ ID NO:23), kwtsd (SEQ ID NO:24), svand (SEQ ID NO:25), and dntwp (SEQ ID NO:26).

In some forms, the ligand comprises an amino acid sequence selected from the group consisting of: lfkhh (SEQ ID NO:16), fGyvd (SEQ ID NO:17), ernta (SEQ ID NO:18), hnwlG (SEQ ID NO:19), wende (SEQ ID NO:20), lnhGt (SEQ ID NO:21), ehtye (SEQ ID NO:22), dwpve (SEQ ID NO:23), kwtsd (SEQ ID NO:24), svand (SEQ ID NO:25), and dntwp (SEQ ID NO:26).

In some forms, the ligand comprises an amino acid sequence selected from the group consisting of: pkvrd (SEQ ID NO:27), frvkd (SEQ ID NO:28), lynre (SEQ ID NO:29), Gydfp (SEQ ID NO:30), sfkyk (SEQ ID NO:31), dyksk (SEQ ID NO:32), wksl (SEQ ID NO:33), rkatp (SEQ ID NO:34), Grkpf (SEQ ID NO:35), kwndd (SEQ ID NO:36), eldd (SEQ ID NO:37), anGsw (SEQ ID NO:38), tkGne (SEQ ID NO:39), plntd (SEQ ID NO:40), kvetd (SEQ ID NO:41), neGfd (SEQ ID NO:42), ekfld (SEQ ID NO:43), dkkaw (SEQ ID NO:44), veyGn (SEQ ID NO:45), and eyprh (SEQ ID NO:46).

In some forms, the ligand comprises an amino acid sequence selected from the group consisting of: revry (SEQ ID NO:3), hreww (SEQ ID NO:10), rdlhw (SEQ ID NO:4), drlhw (SEQ ID NO:5), ert, lpwtr (SEQ ID NO:6), tfnkn (SEQ ID NO:7), wlsGk (SEQ ID NO:8), srdwp (SEQ ID NO:9), lfkhh (SEQ ID NO:16), fGyvd (SEQ ID NO:17), ernta (SEQ ID NO:18), hnwlG (SEQ ID NO:19), wende (SEQ ID NO:20), lnhGt (SEQ ID NO:21), ehtye (SEQ ID NO:22), dwpve (SEQ ID NO:23), kwtsd (SEQ ID NO:24), svand (SEQ ID NO:25), dntwp (SEQ ID NO:26), pkvrd (SEQ ID NO:27), frvkd (SEQ ID NO:28), lynre (SEQ ID NO:29), Gydfp (SEQ ID NO:30), sfkyk (SEQ ID NO:31), dyksk (SEQ ID NO:32), wksl (SEQ ID NO:33), rkatp (SEQ ID NO:34), Grkpf (SEQ ID NO:35), kwndd (SEQ ID NO:36), eldd (SEQ ID NO:37), anGsw (SEQ ID NO:38), tkGne (SEQ ID NO:39), plntd (SEQ ID NO:40), kvetd (SEQ ID NO:41), neGfd (SEQ ID NO:42), ekfld (SEQ ID NO:43), dkkaw (SEQ ID NO:44), veyGn (SEQ ID NO:45), and eyprh (SEQ ID NO:46).

In some forms, the first ligand comprises an amino acid sequence 80-100% identical to an amino acid sequence selected from the group consisting of lpwtr (SEQ ID NO:6), hnwlG (SEQ ID NO:19), wende (SEQ ID NO:20), and lnhGt (SEQ ID NO:21). In some forms, the first ligand comprises an amino acid sequence selected from the group consisting of lpwtr (SEQ ID NO:6), hnwlG (SEQ ID NO:19), wende (SEQ ID NO:20), and lnhGt (SEQ ID NO:21). In some forms, the first ligand comprises an amino acid sequence 80-100% identical to an amino acid sequence selected from the group consisting of revry (SEQ ID NO:3), rdlhw (SEQ ID NO:4), drlhw (SEQ ID NO:5), and ert. In some forms, the first ligand comprises an amino acid sequence selected from the group consisting of revry (SEQ ID NO:3), rdlhw (SEQ ID NO:4), drlhw (SEQ ID NO:5), and ert. In some forms, the first ligand comprises an amino acid sequence 80-100% identical to an amino acid sequence selected from the group consisting of lfkhh (SEQ ID NO:16), fGyvd (SEQ ID NO:17), and ernta (SEQ ID NO:18). In some forms, the first ligand comprises an amino acid sequence selected from the group consisting of lfkhh (SEQ ID NO:16), fGyvd (SEQ ID NO:17), and ernta (SEQ ID NO:18). In some forms, the first ligand comprises an amino acid sequence 80-100% identical to an amino acid sequence selected from the group consisting of hreww (SEQ ID NO:10), tfnkn (SEQ ID NO:7), wlsGk (SEQ ID NO:8), and srdwp (SEQ ID NO:9). In some forms, the first ligand comprises an amino acid sequence selected from the group consisting of hreww (SEQ ID NO:10), tfnkn (SEQ ID NO:7), wlsGk (SEQ ID NO:8), and srdwp (SEQ ID NO:9). In some forms, the first ligand comprises an amino acid sequence 80-100% identical to an amino acid sequence selected from the group consisting of ehtye (SEQ ID NO:22), dwpve (SEQ ID NO:23), kwtsd (SEQ ID NO:24), svand (SEQ ID NO:25), and dntwp (SEQ ID NO:26). In some forms, the first ligand comprises an amino acid sequence selected from the group consisting of ehtye (SEQ ID NO:22), dwpve (SEQ ID NO:23), kwtsd (SEQ ID NO:24), svand (SEQ ID NO:25), and dntwp (SEQ ID NO:26).

In some forms, the second ligand comprises an amino acid sequence 80-100% identical to an amino acid sequence selected from the group consisting of lpwtr (SEQ ID NO:6), hnwlG (SEQ ID NO:19), wende (SEQ ID NO:20), and lnhGt (SEQ ID NO:21). In some forms, the second ligand comprises an amino acid sequence selected from the group consisting of lpwtr (SEQ ID NO:6), hnwlG (SEQ ID NO:19), wende (SEQ ID NO:20), and lnhGt (SEQ ID NO:21). In some forms, the second ligand comprises an amino acid sequence 80-100% identical to an amino acid sequence selected from the group consisting of revry (SEQ ID NO:3), rdlhw (SEQ ID NO:4), drlhw (SEQ ID NO:5), and ert. In some forms, the second ligand comprises an amino acid sequence selected from the group consisting of revry (SEQ ID NO:3), rdlhw (SEQ ID NO:4), drlhw (SEQ ID NO:5), and ert. In some forms, the second ligand comprises an amino acid sequence 80-100% identical to an amino acid sequence selected from the group consisting of lfkhh (SEQ ID NO:16), fGyvd (SEQ ID NO:17), and ernta (SEQ ID NO:18). In some forms, the second ligand comprises an amino acid sequence selected from the group consisting of lfkhh (SEQ ID NO:16), fGyvd (SEQ ID NO:17), and ernta (SEQ ID NO:18). In some forms, the second ligand comprises an amino acid sequence 80-100% identical to an amino acid sequence selected from the group consisting of hreww (SEQ ID NO:10), tfnkn (SEQ ID NO:7), wlsGk (SEQ ID NO:8), and srdwp (SEQ ID NO:9). In some forms, the second ligand comprises an amino acid sequence selected from the group consisting of hreww (SEQ ID NO:10), tfnkn (SEQ ID NO:7), wlsGk (SEQ ID NO:8), and srdwp (SEQ ID NO:9). In some forms, the second ligand comprises an amino acid sequence 80-100% identical to an amino acid sequence selected from the group consisting of ehtye (SEQ ID NO:22), dwpve (SEQ ID NO:23), kwtsd (SEQ ID NO:24), svand (SEQ ID NO:25), and dntwp (SEQ ID NO:26). In some forms, the second ligand comprises an amino acid sequence selected from the group consisting of ehtye (SEQ ID NO:22), dwpve (SEQ ID NO:23), kwtsd (SEQ ID NO:24), svand (SEQ ID NO:25), and dntwp (SEQ ID NO:26).

In some forms, the ligand is cyclic. In some forms the ligand comprises a 1,4-substituted-1,2,3-triazole residue (Tz4) or a 1,5-substituted-1,2,3-triazole residue (Tz5). In some forms, the triazole residue is a 1,4-substituted-1,2,3-triazole (Tz4) residue.

In some forms, the capture agent is labeled with a detectable moiety. In some forms, the detectable moiety is selected from the group consisting of biotin, copper-DOTA, biotin-PEG3, aminooxyacetate, $^{19}$FB, $^{18}$FB and FITC-PEG$_3$. In some forms, the detectable moiety is selected from the group consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{86}$Y, $^{94m}$Tc, $^{110m}$In, $^{11}$C and $^{76}$Br.

In some forms, the capture agent comprises the structure

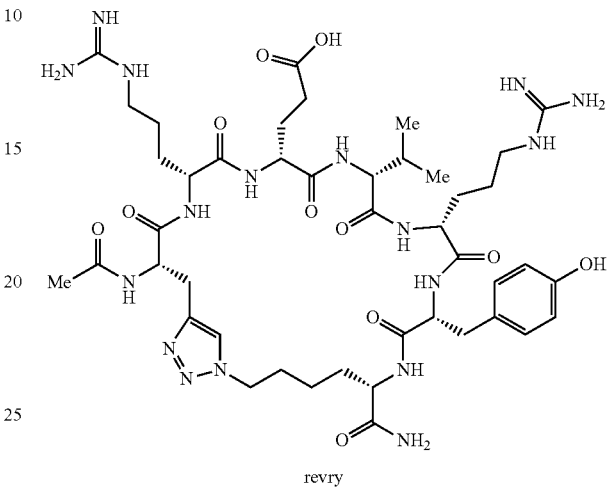

revry

In some forms, the capture agent comprises the structure

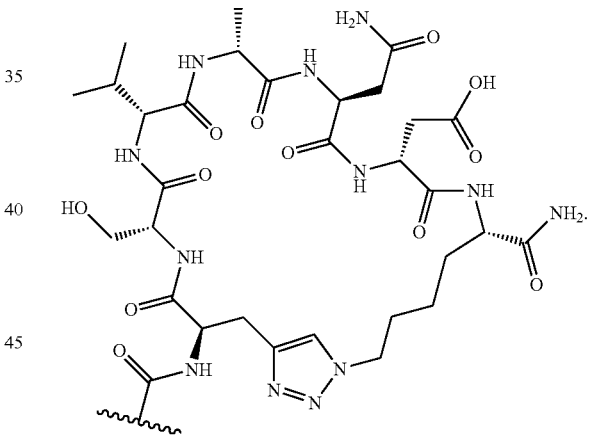

Also disclosed are methods for detecting PSMA in a biological sample, comprising the step of contacting the biological sample with one or more of the PSMA capture agents described herein. In some forms, the method further comprises the steps of binding PSMA to the one or more capture agents, and detecting the detectable moiety linked to the one or more capture agents.

Also disclosed are stable, synthetic capture agents that specifically binds PSMA, wherein the capture agent comprises a first ligand having affinity for a first epitope on PSMA, a second ligand having affinity for a second epitope on PSMA, and a linker covalently connecting the first ligand to the second ligand.

In some forms, the first epitope comprises the amino acid sequence RTEDFFKLERDMK (SEQ ID NO:2). In some forms, the second epitope comprises the amino acid sequence EYAYRRGIAEAVGLPSI (SEQ ID NO:1).

In some forms, the first ligand comprises an amino acid sequence 80-100% identical to an amino acid sequence selected from the group consisting of revry (SEQ ID NO:3), hreww (SEQ ID NO:10), rdlhw (SEQ ID NO:4), drlhw (SEQ ID NO:5), ert, lpwtr (SEQ ID NO:6), tfnkn (SEQ ID NO:7), wlsGk (SEQ ID NO:8), and srdwp (SEQ ID NO:9).

In some forms, the first ligand is cyclic. In some forms, the first ligand comprises a 1,4-substituted-1,2,3-triazole residue (Tz4) or a 1,5-substituted-1,2,3-triazole residue (Tz5). In some forms, the triazole residue is a 1,4-substituted-1,2,3-triazole (Tz4) residue.

In some forms, the linker is divalent. In some forms, the length of the linker corresponds to distance between the first epitope and the second epitope. In some forms, the length of the linker is from ~4.4 Å to ~26.4 Å, from ~8.8 Å to ~26.4 Å or from ~7 Å to ~15 Å. In some forms, the length of the linker is ~15 Å. In some forms, the linker comprises one or more repeat units of ethylene glycol. In some forms, the linker comprises a peptide. In some forms, the linker is glycine. In some forms, the linker is $PEG_1$. In some forms, the linker is $PEG_2$. In some forms, the linker is $PEG_3$. In some forms, the linker is $PEG_4$. In some forms, the linker is $PEG_5$.

In some forms, the capture agent is labeled with a detectable moiety. In some forms, the detectable moiety is selected from the group consisting of biotin, copper-DOTA, biotin-PEG3, aminooxyacetate, $^{19}$FB, $^{18}$FB and FITC-PEG$_3$. In some forms, the detectable moiety is selected from the group consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{86}$Y, $^{94m}$Tc, $^{110m}$In, $^{11}$C and $^{76}$Br.

Also disclosed are methods for detecting PSMA in a biological sample, comprising the step of contacting the biological sample with one or more of the capture agents. In some forms, the capture agent is labeled with a detectable moiety.

In some forms, the method further comprises binding PSMA to the one or more capture agents, and detecting the detectable moiety linked to the one or more capture agents.

Also disclosed are stable, synthetic capture agents that specifically binds PSMA, wherein the capture agent comprises a first ligand having affinity for a first epitope on PSMA, a second ligand having affinity for a second epitope on PSMA, and a linker covalently connecting the first ligand to the second ligand, wherein at least two amino acids of each of the first and the second ligands are D-amino acids.

In some forms, the D-amino acids are D-arginine and D-lysine.

Also disclosed are methods for detecting PSMA in a biological sample. In some forms, the method comprises the step of contacting the biological sample with one or more of the disclosed capture agents.

In some forms, at least one of the capture agents specifically binds PSMA. In some forms, PSMA is detected. In some forms, at least one of the capture agents specifically binds PSMA. In some forms, PSMA is detected. In some forms, at least one of the capture agents specifically binds PSMA. In some forms, PSMA is detected. In some forms, one or more of the capture agents are labeled with a detectable moiety.

In some forms, the method further comprises the steps of binding PSMA to the one or more capture agents, and detecting the detectable moiety linked to the one or more capture agents. In some forms, the method further comprises the steps of binding PSMA to the one or more capture agents, and detecting the detectable moiety linked to the one or more capture agents.

Also disclosed are methods for using the disclosed capture agents. For example, disclosed are methods for detecting PSMA in a biological sample, comprising the step of contacting the biological sample with one or more of the disclosed capture agents. In some forms, the capture agent is labeled with a detectable moiety. In some forms, the method further comprises the steps of binding PSMA to the one or more capture agents, and detecting the detectable moiety linked to the one or more capture agents.

Also disclosed are stable, synthetic capture agents that specifically binds PSMA, where the capture agent comprises a first ligand having affinity for a first epitope on PSMA, a second ligand having affinity for a second epitope on PSMA, and a linker covalently connecting the first ligand to the second ligand. In some forms, the first epitope comprises the amino acid sequence RTEDFFKLERDMK (SEQ ID NO:2). In some forms, the second epitope comprises the amino acid sequence EYAYRRGIAEAVGLPSI (SEQ ID NO:1).

Also disclosed are methods for detecting PSMA in a subject, the method comprising the step of administering one or more capture agents to the subject. In some forms, at least one of the capture agents specifically binds PSMA. In some forms, PSMA is detected. In some forms, one or more of the capture agents are loaded with a detectable moiety. In some forms, the method further comprises the steps of binding PSMA to the one or more capture agents, and detecting the detectable moiety linked to the one or more capture agents. In some forms, the method further comprises the steps of binding PSMA to the one or more capture agents, and detecting the detectable moiety linked to the one or more capture agents.

Also disclosed are methods for treating a subject in need thereof, the method comprising the step of administering one or more capture agents to the subject, where the subject has a disease or condition that can be targeted via PSMA. In some forms, the disease of condition is cancer. In some forms, at least one of the capture agents specifically binds PSMA. In some forms, one or more of the capture agents are loaded with a therapeutic moiety. In some forms, one or more of the one or more capture agents are loaded with a detectable moiety. In some forms, one or more of the one or more capture agents loaded with the therapeutic moiety are also loaded with a detectable moiety. In some forms, the method further comprises administering one or more additional capture agents to the subject, wherein one or more of the one or more additional capture agents are loaded with a detectable moiety. In some forms, one or more of the one or more additional capture agents are administered at or near the same time as, or together with, one or more of the capture agents are administered. In some forms, one or more of the one or more additional capture agents are administered at a different time than one or more of the capture agents are administered.

Additional advantages of the disclosed method and compositions will be set forth in part in the description which follows, and in part will be understood from the description, or can be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several forms and embodiments of the disclosed method and compositions and together with the description, serve to explain the principles of the disclosed method and compositions.

FIG. 11A shows the first screening using ImmPACT Vector Red. FIG. 11B shows the second and third screenings using BCIP/NBT and LNCaP cells, respectively.

DETAILED DESCRIPTION OF THE INVENTION

Figure 1:
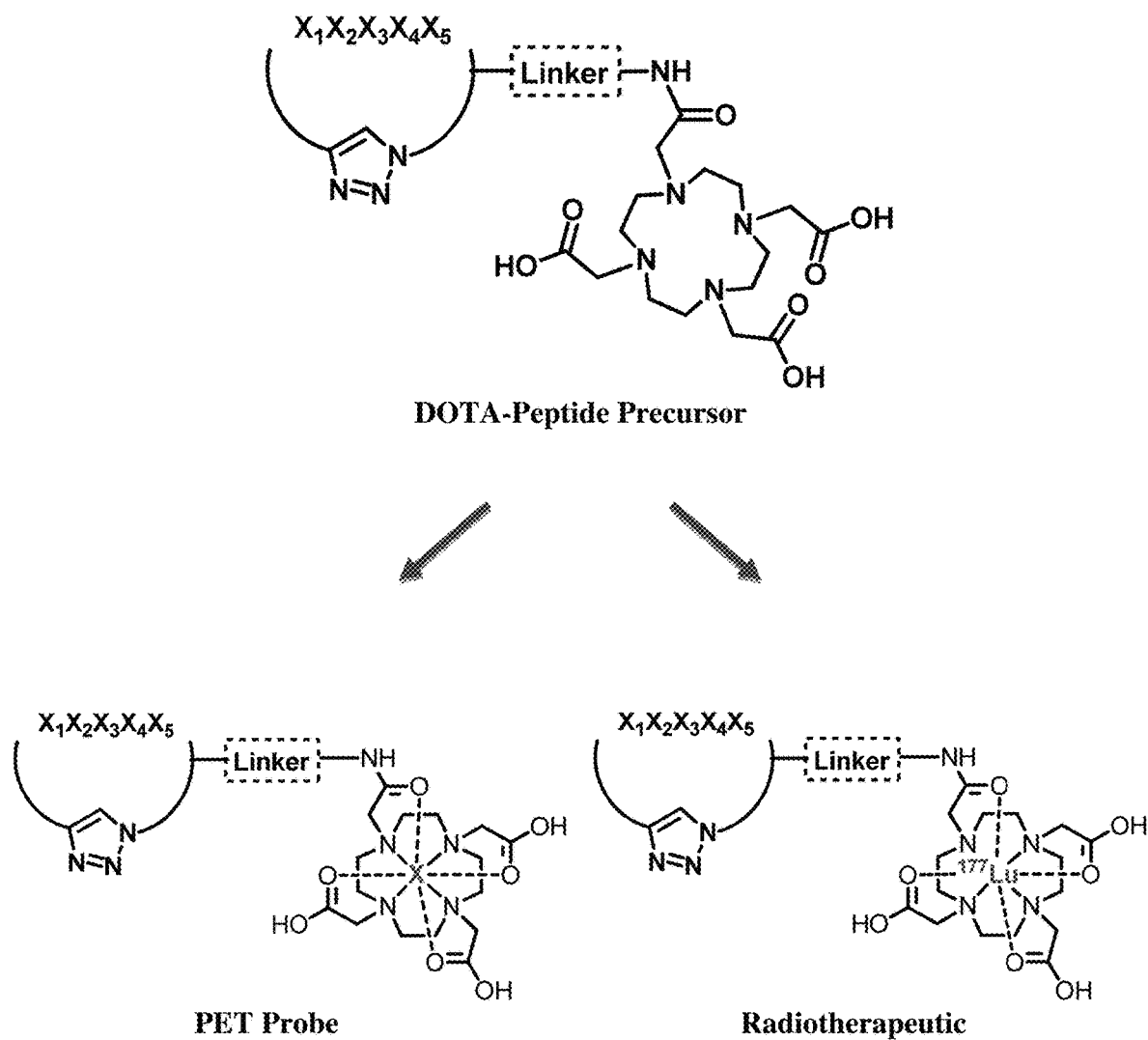
FIG. 1 shows the generic structure of an example of a single peptide theranostic capture agent. The precursor (top structure; shown with an unloaded DOTA chelator) is available for loading with ligand atom. By loading the chelator with a detectable radioisotope, the capture agent can be used for detection and imaging (bottom left structure). X=detectable radioisotope, such as $Al^{18}F$ or $^{68}Ga$. By loading the chelator with an ablating radioisotope, the capture agent can be used for therapy (bottom right structure; shown with $^{177}Lu$ as the radioisotope). $X_1X_2X_3X_4X_5$=amino acids of the capture agent.
Figure 2:
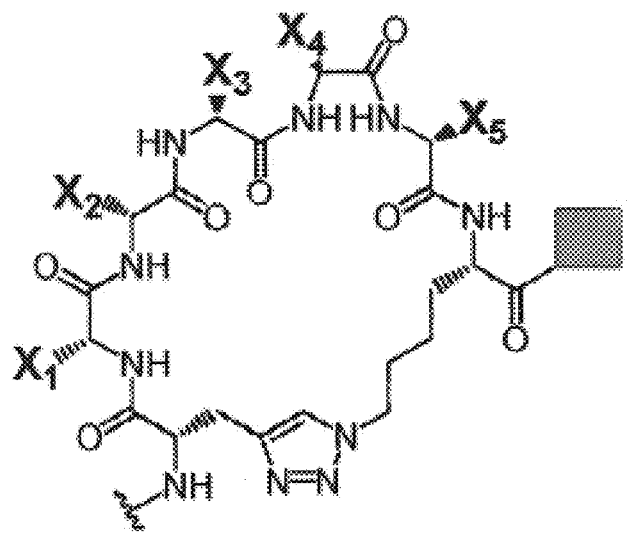
FIG. 2 shows the generic structure of an example of a single peptide theranostic capture agent. X=amino acid side chain, small molecule, or radioisotope/chelator. The shaded box represents the C-terminus of the peptide or a radioisotope/chelator.
Figure 3:
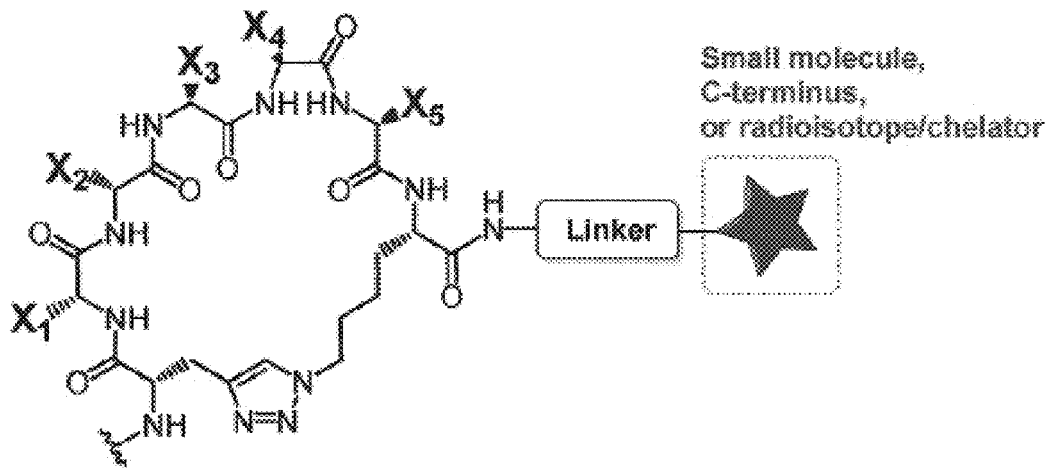
FIG. 3 shows the generic structure of an example of a single peptide theranostic capture agent coupled to a small molecule (a heterobiligand). X=amino acid side chain, small molecule, or radioisotope/chelator. The star represents the C-terminus of the peptide, a small molecule, or a radioisotope/chelator.
Figure 4:
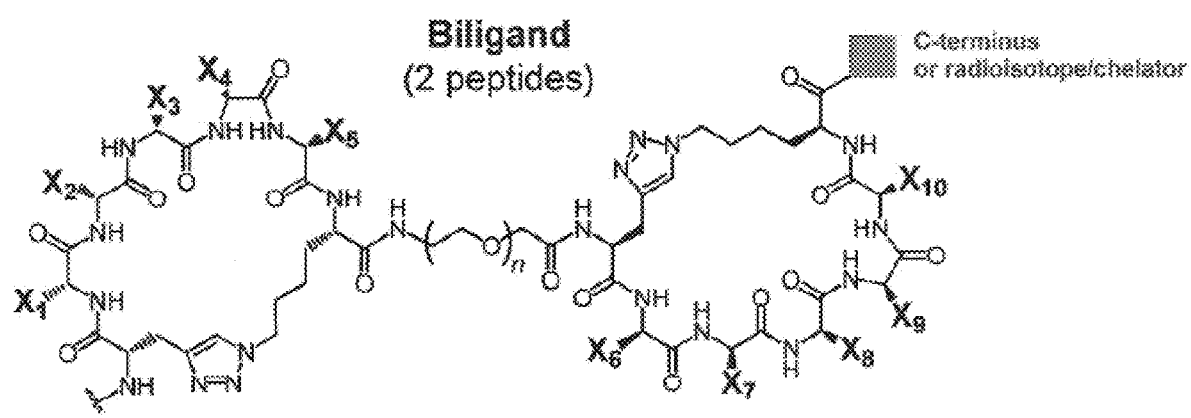
FIG. 4 shows the generic structure of an example of a dual peptide theranostic capture agent (biligand). X=amino acid side chain, small molecule, or radioisotope/chelator. The shaded box represents the C-terminus of the peptide or a radioisotope/chelator. n=1, 2, 3, 4, 5, or more (length determined by distance between target ligands of the two peptides).
Figure 5:
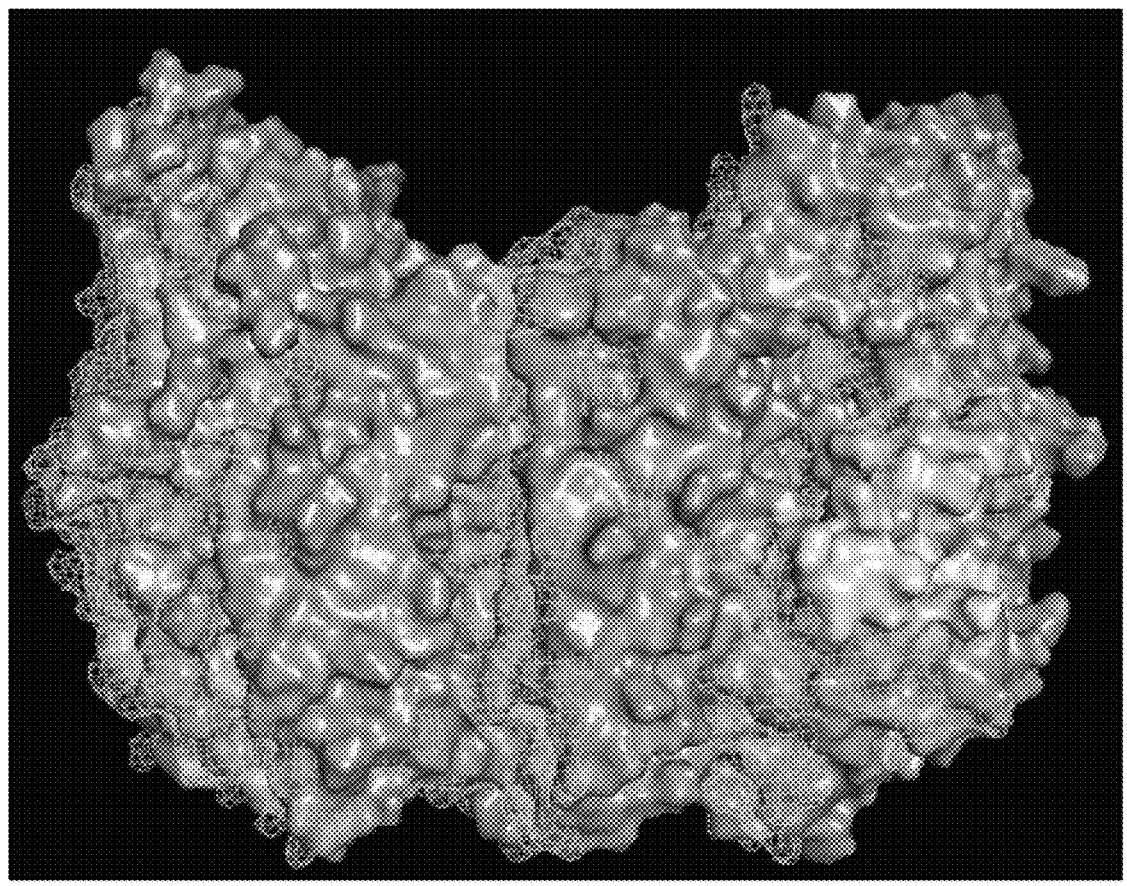
FIG. 5 shows the minimized and equilibrated structure of PSMA. Epitopes 2 and 3 have subtly different shading.
Figure 6:
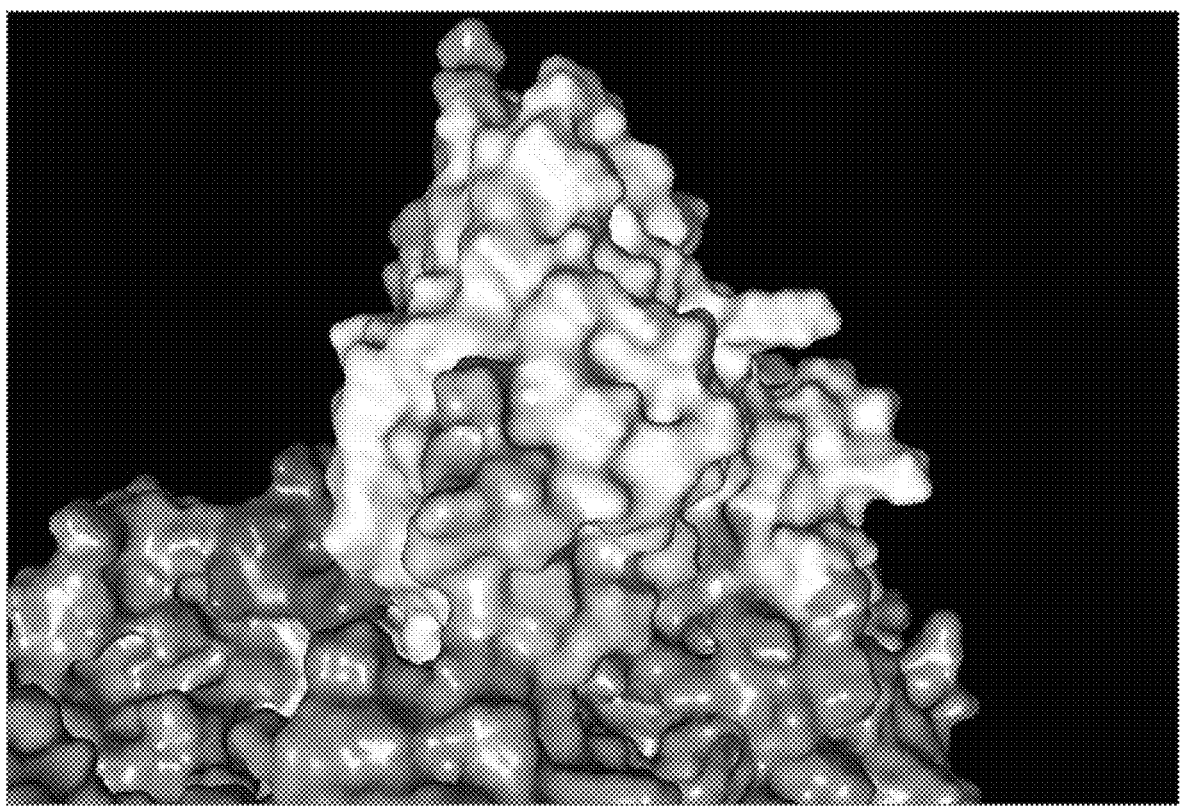
FIG. 6 shows a portion of the minimized and equilibrated structure of PSMA. Epitopes 4, 5, and J591 have subtly different shading.
Figure 7A:
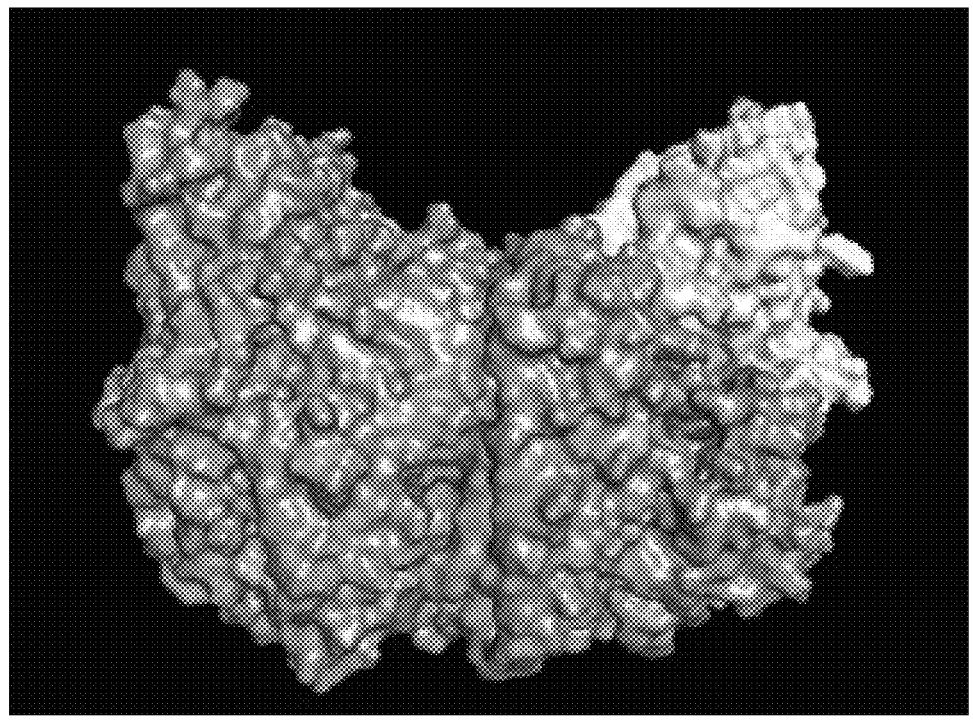
FIGS. 7A and 7B shows the minimized and equilibrated structure of PSMA from each side. Epitopes 2 and 3 have subtly different shading.
Figure 7B:
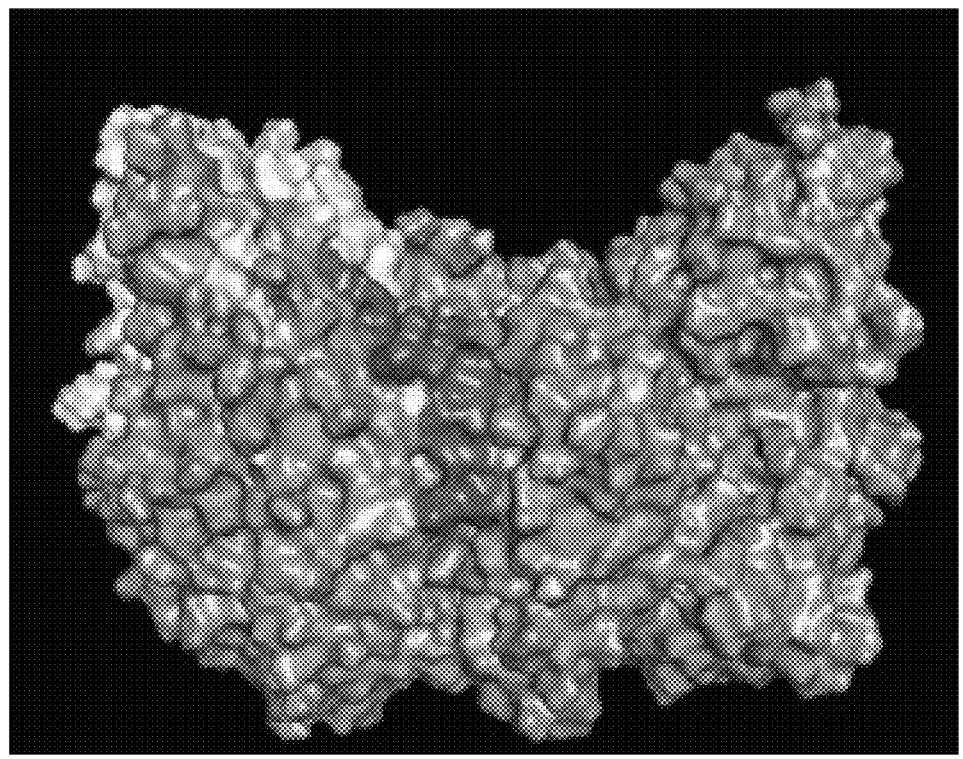
Figure 8:
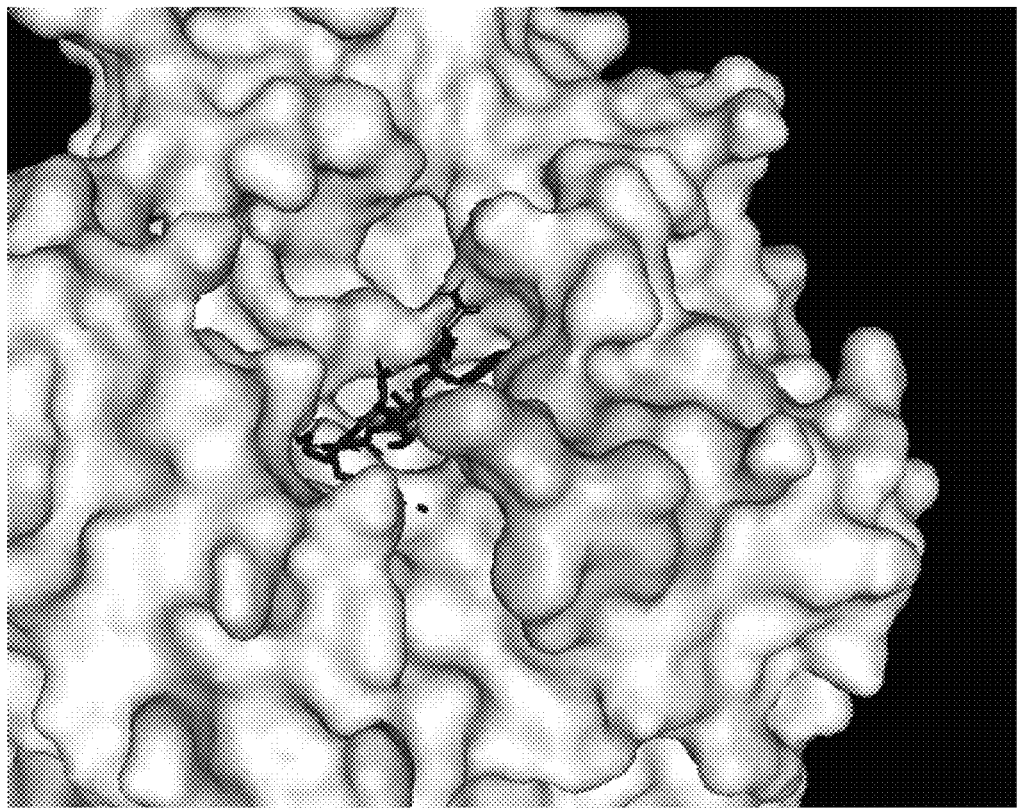
FIG. 8 shows a portion of the minimized and equilibrated structure of PSMA. Epitope 2 has subtly different shading. Ligand revry (SEQ ID NO:3) is the wire structure next to epitope 2.

The disclosed method and compositions can be understood more readily by reference to the following detailed description of particular forms and embodiments and the Examples included therein and to the Figures and their previous and following description.

The following description of the invention is merely intended to illustrate various forms and embodiments of the invention. As such, the specific modifications discussed are not to be construed as limitations on the scope of the invention. It will be apparent to one skilled in the art that various equivalents, changes, and modifications can be made without departing from the scope of the invention, and it is understood that such equivalent forms and embodiments are to be included herein.

It has been discovered that capture agents identified using the PCC platform can be modified to be used for both diagnosis and therapy (theranostic) when labeled with suitable diagnostic or therapeutic radionuclide, respectively. In PCC, macrocyclic peptides are selected against specific epitopes of a cell surface target by screening one-bead-one-compound (OBOC) libraries. This approach can be generally applied, for example, to targets that are highly expressed on cancer cells, and that have low expression on normal cells. During the screen, hit peptides that bind to the epitope in a preferred orientation template a click reaction resulting in a covalently bound product and strong binding homology. The OBOC peptide library can include canonical and non-canonical (unnatural) amino acids, including D-amino acids to impart stability. Hit peptides can then sequenced and synthesized in order to characterize the binding to purified target protein and/or target in a cellular context. Hits can be further developed into a heterobiligand by attaching a small molecule or biligand by attaching a second peptide using a chemical linker. The biligand can comprise, for example, two different peptide sequences or two peptides of the same sequence. These peptides are amenable to medicinal chemistry and are therefore highly modular, resulting in short and adjustable pharmacokinetics that are attractive for theranostic applications. These peptides may be efficiently and site-specifically labeled with radioisotopes for theranostic applications. Bifunctional chelating agents can bind radiometals and still append a chemically reactive functional group for covalent attachment to the peptide. For incorporation of PET imaging diagnostics radionuclides such as $Al^{18}F$ and $^{68}Ga$, the macrocyclic NOTA or DOTA chelator can be used, forming kinetically and thermodynamically stable complexes. For incorporation of therapeutic radionuclides such as $^{177}Lu$ and $^{225}Ac$, the macrocyclic DOTA chelator can also be used. The common chelation chemistry thus achieves targeted PET imaging of tumors and targeted delivery of therapeutic radionuclide to tumors using the same peptide.

PCCs can play a central role in theranostic applications given their ability to be deployed as both a precision in vivo PET diagnostic and a targeted therapeutic. This dual role is accomplished by changing the radionuclide that is captured within the common payload chemistry applicable to all PCC capture agents. Thus, a single capture agent-chelator serves as a common precursor of both a diagnostic capture agent and a therapeutic capture agent. PCCs routinely demonstrate single amino acid specificity and sub nanomolar affinities with pharmacological properties of small molecules that are easily modified using conventional medicinal chemistry.

The disclosed theranostic capture agents have several advantages. First, the capture agent binds the same target allowing both imaging and therapeutic delivery to the same target, so there is no difference between where the target is detected and where the therapeutic is targeted. Second, the precursor capture agent accepts either a detectable moiety or a therapeutic moiety without modification, thus making it versatile. Third, the PCC system for developing capture agents has a common preclinical development pathway irrespective of the cellular target and helps reduce development time.

The disclosed theranostic capture agents are particularly useful for theranostic treatment of ovarian, pancreatic and other difficult to diagnose and treat cancers. In the case of pancreatic and ovarian cancers, the lack of effective treatment and the dilemma of predominantly late-stage disease discovery creates significant market opportunity with: 13,920 ovarian and 41,615 pancreatic cancers of all stages discovered annually in the US. Since surgery is generally not an effective first-line Rx given the typically advanced clinical stage of discovery of both cancers, a PCC-based theranostic can be used in the majority of new cases. Treatment could be further enhanced by treating the patient with check point inhibitors after the post theranostic treatment to enable the patient's immune system to attack residual disease that may remain post theranostic treatment.

As an example, theranostic peptides that are targeted against prostate specific membrane antigen (PSMA) are described. Capture agents can be developed using an OBOC peptide library on TentaGel S NH$_2$ resin with a 5-residue variable region, cyclization of the flanking alkyne and azide-modified amino acid side chains by copper-catalyzed azide-alkyne cycloaddition (CuAAC), and an N-terminal alkyne-modified amino acid as a click handle for screening. This library is screen against four synthetic PSMA epitopes with a biotin detection label and a strategically substituted azide-presenting amino acid. Five epitopes on PSMA have been identified and assessing epitopes as target ligands for capture agents. An in silico method was used to increase the likelihood of generating quality hits against the target protein. Examples of the attributes identified as leading to a quality hit include the flexibility or rigidity of the epitope (within the context of the entire protein), solvent exposed surface area, overall charge, post-translational modification, and volume of the surrounding surface.

Epitopes 2 and 3 were selected due to their close proximity to the PSMA active site. The distance between these epitopes should allow for the synthesis of short-linker biligands. Epitopes 2A/2B are in close proximity to the PSMA active site. Epitopes 4 and 5 are sequences contained within the putative binding site of the J591 antibody.

Epitope 4 is EYAYRRGIAEAVGLPSI (SEQ ID NO:1). Epitope 5 is RTEDFFKLERDMK (SEQ ID NO:2). Epitopes 4 and 5 are sequences contained within the putative binding location of J591, the clinical PSMA antibody. Epitope 4 is located on the opposite face of the active site of PSMA. Epitope 5 is positioned directly above the active site, and is close enough to allow for biligand conjugation (~20 Å away from Epitope 3).

|  | Epitope 4 | Epitope 5 |
|---|---|---|
| Sequence | [E276-I292] EYAYRRGIAEAVGLPSI (SEQ ID NO: 1) | [R181-K193] RTEDFFKLERDMK (SEQ ID NO: 2) |
| Total Surface Area | 1926.545 Å$^2$ | 1937.435 |
| Solvent Accessible Surface Area | 1108.787 Å$^2$ | 1017.91 |
| Net Charge | 0 | 0 |
| Average Backbone RMSD | 1.984 Å (0.489) | 3.924 Å (0.722) |
| Average RMSD (includes side chains) | 2.45 Å (0.499) | 4.723 Å (0.781) |

Ligands identified for epitope 2 include ert, revry (SEQ ID NO:3), rdlhw (SEQ ID NO:4), and drlhw (SEQ ID NO:5). Ligands identified for epitope 4 include lpwtr (SEQ ID NO:6). Ligands identified for epitope 5 include tfnkn (SEQ ID NO:7), wlsGk (SEQ ID NO:8), srdwp (SEQ ID NO:9), and hreww (SEQ ID NO:10).

Testing of biotin-PEG10-PEG10-peptide ligands for epitope 5 against His-PSMA (Sino Biological) and PSMA-Myc-Flag (Origene) identified hreww (SEQ ID NO:10) has nanomolar binding affinity to both PSMA proteins.

The epitope 2 peptide ligand revry (SEQ ID NO:3) was docked against the equilibrated PSMA structure. The lowest energy binding mode shows that revry (SEQ ID NO:3) binds to epitope 2 just outside of the active site of PSMA. The close proximity to the active site allows revry (SEQ ID NO:3) to be used in a heterobiligand, with a zinc binder being the other ligand.

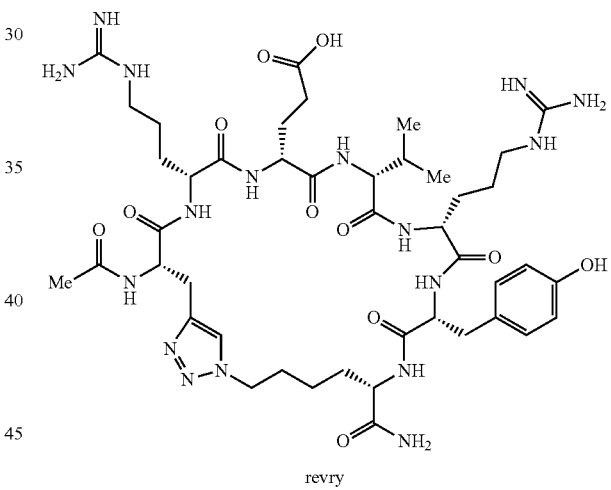

revry

Examples of zinc binders include

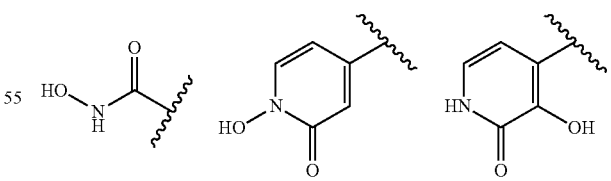

A. Definitions

"Amino" refers to the —NH$_2$ radical.
"Cyano" refers to the —CN radical.
"Hydroxy" or "hydroxyl" refers to the —OH radical.
"Imino" refers to the =NH substituent.
"Nitro" refers to the —NO$_2$ radical.

"Oxo" refers to the =O substituent.

"Thioxo" refers to the =S substituent.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n propyl, 1 methylethyl (isopropyl), n-butyl, n-pentyl, 1,1 dimethylethyl (t-butyl), 3 methylhexyl, 2 methylhexyl, ethenyl, prop-1-enyl, but-1-enyl, pent-1-enyl, penta 1,4 dienyl, ethynyl, propynyl, butynyl, pentynyl, hexynyl, and the like. Unless stated otherwise specifically in the specification, an alkyl group can be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain can be optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group can be optionally substituted.

"Aminocarbonyl" refers to a radical of the formula —C(=O)$NR_aR_a$, where each $R_a$ is independently H, alkyl or a linker moiety.

"α-amino carbonyl" refers to a radical of the formula —C(=O)$CR_b$($NR_aR_a$), where each $R_a$ is independently H, alkyl or a linker moiety and $R_b$ is H or alkyl. In some forms, an alpha amino carbonyl is part of a cyclic moiety (e.g., peptide) where the carbonyl is within the ring and the amino ($NR_aR_a$) is exocyclic. For example, in some forms an alpha aminocarbonyl is useful for Edman degradation of cyclic peptides.

α-amido carbonyl" refers to a radical of the formula —C(=O)$CR_b$(N(C=O)$R_aR_a$), where each $R_a$ is independently H, alkyl or a linker moiety and $R_b$ is H or alkyl. In some forms, an alpha amido carbonyl is part of a cyclic moiety (e.g., peptide) where the carbonyl is within the ring and the amido (N(C=O)$R_aR_a$) is exocyclic.

"Alkylamino" refers to a radical of the formula —$NHR_a$ or —$NR_aR_a$ where each $R_a$ is, independently, an alkyl radical as defined above containing one to twelve carbon atoms. Unless stated otherwise specifically in the specification, an alkylamino group can be optionally substituted.

"Thioalkyl" refers to a radical of the formula —$SR_a$ where $R_a$ is an alkyl radical as defined above containing one to twelve carbon atoms. Unless stated otherwise specifically in the specification, a thioalkyl group can be optionally substituted.

"Aryl" refers to a hydrocarbon ring system radical comprising hydrogen, 6 to 18 carbon atoms and at least one aromatic ring. For present purposes, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. Unless stated otherwise specifically in the specification, an aralkyl group can be optionally substituted.

"Cycloalkyl" or "carbocyclic ring" refers to a stable non aromatic monocyclic or polycyclic hydrocarbon radical consisting solely of carbon and hydrogen atoms, which can include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7 dimethyl bicyclo[2.2.1]heptanyl, and the like. Unless otherwise stated specifically in the specification, a cycloalkyl group can be optionally substituted.

"Cycloalkylalkyl" refers to a radical of the formula —$R_bR_d$ where $R_b$ is an alkylene chain as defined above and $R_d$ is a cycloalkyl radical as defined above. Unless stated otherwise specifically in the specification, a cycloalkylalkyl group can be optionally substituted.

"Fused" refers to any ring structure described herein which is fused to an existing ring structure in the disclosed compounds. When the fused ring is a heterocyclyl ring or a heteroaryl ring, any carbon atom on the existing ring structure which becomes part of the fused heterocyclyl ring or the fused heteroaryl ring can be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2 trifluoroethyl, 1,2 difluoroethyl, 3 bromo 2 fluoropropyl, 1,2 dibromoethyl, and the like. Unless stated otherwise specifically in the specification, a haloalkyl group can be optionally substituted.

"Heterocyclyl" or "heterocyclic ring" refers to a stable 3 to 18 membered non aromatic ring radical which consists of two to twelve carbon atoms and from one to six heteroatoms selected from the group consisting of nitrogen, oxygen and sulfur. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2 oxopiperazinyl, 2 oxopiperidinyl, 2 oxopyrrolidinyl, oxazolidinyl, piperidinyl, piperazinyl, 4 piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1 oxo thiomorpholinyl, and 1,1 dioxo thiomorpholinyl. Unless stated otherwise specifically in the specification, a heterocyclyl group can be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, an N-heterocyclyl group can be optionally substituted.

"Heterocyclylalkyl" refers to a radical of the formula —RbRe where Rb is an alkylene chain as defined above and Re is a heterocyclyl radical as defined above, and if the heterocyclyl is a nitrogen containing heterocyclyl, the heterocyclyl can be attached to the alkyl radical at the nitrogen atom. Unless stated otherwise specifically in the specification, a heterocyclylalkyl group can be optionally substituted.

"Heteroaryl" refers to a 5 to 14 membered ring system radical comprising hydrogen atoms, one to thirteen carbon atoms, one to six heteroatoms selected from the group consisting of nitrogen, oxygen and sulfur, and at least one aromatic ring. For present purposes, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4 benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2 a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2 oxoazepinyl, oxazolyl, oxiranyl, 1-oxidopyridinyl, 1 oxidopyrimidinyl, 1-oxidopyrazinyl, 1-oxidopyridazinyl, 1 phenyl 1H pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group can be optionally substituted.

"Heteroarylalkyl" refers to a radical of the formula —$R_bR_f$ where $R_b$ is an alkylene chain as defined above and Rf is a heteroaryl radical as defined above. Unless stated otherwise specifically in the specification, a heteroarylalkyl group can be optionally substituted.

The term "substituted" used herein means any of the above groups (e.g., alkyl, alkylene, alkoxy, alkylamino, aminocarbonyl, α-aminocarbonyl, α-amidocarbonyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

"Prodrug" is meant to indicate a compound that can be converted under physiological conditions or by solvolysis to a biologically active compound (e.g., a disclosed capture agent). Thus, the term "prodrug" refers to a metabolic precursor of a compound that is pharmaceutically acceptable. A prodrug can be inactive when administered to a subject in need thereof, but is converted in vivo to an active compound. Prodrugs are typically rapidly transformed in vivo to yield the parent compound, for example, by hydrolysis in blood. The prodrug compound often offers advantages of solubility, tissue compatibility or delayed release in a mammalian organism (see, Bundgard, H., Design of Prodrugs (1985), pp. 7 9, 21 24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of a compound can be prepared by modifying functional groups present in the compound in such a way that the modifications are cleaved, either in routine manipulation or in vivo, to the parent compound. Prodrugs include compounds wherein a hydroxy, amino or mercapto group is bonded to any group that, when the prodrug of the compound is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds and the like.

The disclosed capture agents can also be isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to pharmacologically important site of action. Certain isotopically-labeled disclosed capture agents, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, can afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled capture agents can generally be prepared by conventional techniques known to those skilled in the art or by processes analogous to those described in the Preparations and Examples as set out below using an appropriate isotopically-labeled reagent in place of the non-labeled reagent previously employed.

Also disclosed are the in vivo metabolic products of the disclosed capture agents. Such products can result from, for example, the oxidation, reduction, hydrolysis, amidation, esterification, and the like of the administered compound, primarily due to enzymatic processes. Accordingly, disclosed are compounds produced by a process comprising administering a disclosed compound (e.g., capture agent) to a mammal for a period of time sufficient to yield a metabolic product thereof. Such products can typically be identified by administering a radiolabeled compound in a detectable dose to an animal, such as rat, mouse, guinea pig, monkey, or to human, allowing sufficient time for metabolism to occur, and isolating its conversion products from the urine, blood or other biological samples.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2 dimethylaminoethanol, 2 diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N ethylpiperidine, polyamine resins and the like. Particularly preferred organic bases are isopropylamine, diethylamine, ethanolamine, trimethylamine, dicyclohexylamine, choline and caffeine.

The disclosed compounds (e.g., capture agents), or their pharmaceutically acceptable salts, may contain one or more asymmetric centers and may thus give rise to enantiomers, diastereomers, and other stereoisomeric forms that can be defined, in terms of absolute stereochemistry, as (R) or (S) or, as (D) or (L) for amino acids. All such possible isomers, as well as their racemic and optically pure forms, are included in the scope of the compounds. Optically active (+) and ( ) (R) and (S), or (D) and (L) isomers can be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. (D)-amino acids (also referred to as D-amino acids) are referred to herein in lower case letters (e.g. D-valine is referred to as "v"), while (L)-amino acids (also referred to herein as L-amino acids) are referred to in upper case letters (e.g. L-valine or valine is referred to as "V"). Glycine is non-chiral and is referred to as "G".

A "stereoisomer" refers to a compound made up of the same atoms bonded by the same bonds but having different three-dimensional structures, which are not interchangeable. Various stereoisomers and mixtures thereof are contemplated herein, including "enantiomers," which refers to two stereoisomers whose molecules are nonsuperimposeable mirror images of one another.

A "tautomer" refers to a proton shift from one atom of a molecule to another atom of the same molecule. The disclosed compounds (e.g., capture agents) include tautomers of any of the compounds.

Often crystallizations produce a solvate of the compound (e.g., capture agent). As used herein, the term "solvate" refers to an aggregate that comprises one or more molecules of a compound with one or more molecules of solvent. The solvent can be water, in which case the solvate can be a hydrate. Alternatively, the solvent can be an organic solvent. Thus, the disclosed compounds can exist as a hydrate, including a monohydrate, dihydrate, hemihydrate, sesquihydrate, trihydrate, tetrahydrate and the like, as well as the corresponding solvated forms. The disclosed compounds may be true solvates, while in other cases, the disclosed compounds may merely retain adventitious water or be a mixture of water plus some adventitious solvent.

The term "capture agent" as used herein refers to a composition that comprises two or more target-binding moieties and which specifically binds to a target protein via those target-binding moieties. Each target-binding moiety exhibits binding affinity for the target protein, either individually or in combination with other target-binding moieties. In some forms, each target-binding moiety binds to the target protein via one or more non-covalent interactions, including for example hydrogen bonds, hydrophobic interactions, and van der Waals interactions. A capture agent can comprise one or more organic molecules, including for example polypeptides, peptides, polynucleotides, and other non-polymeric molecules. In some aspects a capture agent is a protein catalyzed capture agent (PCC).

The term "epitope" as used herein refers to a distinct molecular surface of a protein (e.g., PSMA). Typically, the epitope is a polypeptide and it can act on its own as a finite sequence of 10-40 amino acids.

The terms "polypeptide," "peptide," and "protein" are used interchangeably herein to refer to an amino acid sequence comprising a polymer of amino acid residues. The terms apply to amino acid polymers in which one or more amino acid residues is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids, and isomers thereof. Naturally occurring amino acids are those encoded by the genetic code, as well as those amino acids that are later modified, e.g., hydroxyproline, carboxyglutamate, 0-phosphoserine, and isomers thereof. The term "amino acid analogs" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The term "amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

The term "non-natural amino acid" as used herein refers to an amino acid that is different from the twenty naturally occurring amino acids (alanine, arginine, glycine, asparagine, aspartic acid, cysteine, glutamine, glutamic acid, serine, threonine, histidine, lysine, methionine, proline, valine, isoleucine, leucine, tyrosine, tryptophan, phenylalanine) in its side chain functionality. The non-natural amino acid can be a close analog of one of the twenty natural amino acids, or it can introduce a completely new functionality and chemistry, as long as the hydrophobicity of the non-natural amino acid is either equivalent to or greater than that of the natural amino acid. The non-natural amino acid can either replace an existing amino acid in a protein (substitution), or be an addition to the wild type sequence (insertion). The incorporation of non-natural amino acids can be accomplished by known chemical methods including solid-phase peptide synthesis or native chemical ligation, or by biological methods.

The terms "specific binding," "selective binding," "selectively binds," or "specifically binds" as used herein refer to capture agent binding to an epitope on a predetermined antigen. Typically, the capture agent binds with an affinity ($K_D$) of approximately less than $10^{-7}$ M, such as approximately less than $10^{-8}$ M, $10^{-9}$ M or $10^{-10}$ M or even lower.

The term "$K_D$" as used herein refers to the dissociation equilibrium constant of a particular capture agent-antigen interaction. Typically, the disclosed capture agents bind to PSMA with a dissociation equilibrium constant ($K_D$) of less than approximately $10^{-6}$ M, $10^{-7}$ M, such as less than approximately $10^{-8}$ M, $10^{-9}$ M or $10^{-10}$ M or even lower, for example, as determined using surface plasmon resonance (SPR) technology in a Biacore instrument using the antigen as the ligand and the capture agent as the analyte, and binds to the predetermined antigen with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the capture agent, so that when the $K_D$ of the capture agent is very low (that is, the capture agent is highly specific), then the amount with which the affinity for the antigen is lower than the affinity for a non-specific antigen can be at least 10,000 fold.

The term "$k_d$" ($sec^{-1}$) as used herein refers to the dissociation rate constant of a particular capture agent-antigen interaction. Said value is also referred to as the $k_{off}$ value.

The term "$k_a$" ($M^{-1} \times sec^{-1}$) as used herein refers to the association rate constant of a particular capture agent-antigen interaction.

The term "$K_D$" (M) as used herein refers to the dissociation equilibrium constant of a particular capture agent-antigen interaction.

The term "$K_A$" ($M^{-1}$) as used herein refers to the association equilibrium constant of a particular capture agent-antigen interaction and is obtained by dividing the $k_a$ by the $k_d$.

A "pharmaceutical composition" refers to a formulation of a compound (e.g., capture agent) and a medium generally accepted in the art for the delivery of the biologically active compound to mammals, e.g., humans. Such a medium includes all pharmaceutically acceptable carriers, diluents or excipients therefor.

The term "condition" as used herein refers generally to a disease, event, or a change in health status. A change in health status may be associated with a particular disease or event, in which case the change may occur simultaneously with or in advance of the disease or event. In those cases where the change in health status occurs in advance of a disease or event, the change in health status can serve as a predictor of the disease or event. For example, a change in health status may be an alteration in the expression level of a particular gene associated with a disease or event. Alternatively, a change in health status may not be associated with a particular disease or event.

The terms "treat," "treating," or "treatment" as used herein generally refer to preventing a condition or event, slowing the onset or rate of development of a condition or delaying the occurrence of an event, reducing the risk of developing a condition or experiencing an event, preventing or delaying the development of symptoms associated with a condition or event, reducing or ending symptoms associated with a condition or event, generating a complete or partial regression of a condition, lessening the severity of a condition or event, or some combination thereof.

An "effective amount" or "therapeutically effective amount" as used herein refers to an amount effective, at dosages and for periods of time necessary, to achieve a desired therapeutic result. A therapeutically effective amount of a disclosed capture agent may vary according to factors such as the disease state, age, sex, and weight of the individual, and the ability of the capture agent to elicit a desired response in the individual.

The term "stable" as used herein with regard to a capture agent protein catalyzed capture agent or pharmaceutical formulation thereof refers to the agent or formulation retaining structural and functional integrity for a sufficient period of time to be utilized in the methods described herein.

The term "synthetic" as used herein with regard to a protein catalyzed capture agent or capture agent refers to the capture agent has been generated by chemical rather than biological means.

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions can be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (Claverie and States, (1993) Comput. Chem. 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity can be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) Computer Applic. Biol. Sci. 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "substantially identical" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

In some forms, the term "PSMA" as used herein refers to human PSMA. In some forms, PSMA comprises the following amino acid sequence or an amino acid sequence substantially identical to it.

```
                                            (SEQ ID NO: 51)
         10         20         30         40
MWNLLHETDS AVATARRPRW LCAGALVLAG GFFLLGFLFG 50         60         70         80
WFIKSSNEAT NITPKHNMKA FLDELKAENI KKFLYNFTQI 90        100        110        120
PHLAGTEQNF QLAKQIQSQW KEFGLDSVEL AHYDVLLSYP 130        140        150        160
NKTHPNYISI INEDGNEIFN TSLFEPPPPG YENVSDIVPP 170        180        190        200
FSAFSPQGMP EGDLVYVNYA RTEDFFKLER DMKINCSGKI 210        220        230        240
VIARYGKVFR GNKVKNAQLA GAKGVILYSD PADYFAPGVK 250        260        270        280
SYPDGWNLPG GGVQRGNILN LNGAGDPLTP GYPANEYAYR 290        300        310        320
RGIAEAVGLP SIPVHPIGYY DAQKLLEKMG GSAPPDSSWR 330        340        350        360
GSLKVPYNVG PGFTGNFSTQ KVKMHIHSTN EVTRIYNVIG 370        380        390        400
TLRGAVEPDR YVILGGHRDS WVFGGIDPQS GAAVVHEIVR 410        420        430        440
SFGTLKKEGW RPRRTILFAS WDAEEFGLLG STEWAEENSR 450        460        470        480
LLQERGVAYI NADSSIEGNY TLRVDCTPLM YSLVHNLTKE 490        500        510        520
LKSPDEGFEG KSLYESWTKK SPSPEFSGMP RISKLGSGND 530        540        550        560
FEVFFQRLGI ASGRARYTKN WETNKFSGYP LYHSVYETYE 570        580        590        600
LVEKFYDPMF KYHLTVAQVR GGMVFELANS IVLPFDCRDY 610        620        630        640
AVVLRKYADK IYSISMKHPQ EMKTYSVSFD SLFSAVKNFT 650        660        670        680
EIASKFSERL QDFDKSNPIV LRMMNDQLMF LERAFIDPLG 690        700        710        720
LPDRPFYRHV IYAPSSHNKY AGESFPGIYD ALFDIESKVD 730        740        750
PSKAWGEVKR QIYVAAFTVQ AAAETLSEVA
```

In other forms, PSMA is a protein encoded by the gene represented by Entrez Gene ID Number 2346.

B. Development of PSMA Capture Agents

Antibodies are currently the default detection agent for use in diagnostic platforms. However, antibodies possess several disadvantages, including high cost, poor stability, and, in many cases, lack of proper characterization and high specificity. The ideal replacement for use in diagnostic assays should be synthetic, stable to a range of thermal and chemical conditions, and display high affinity and specificity for the target of interest.

A high quality monoclonal antibody possesses low-nanomolar affinity and high target specificity. Interestingly, structural and genetic analyses of the antigen recognition surface have shown that the majority of the molecular diversity of the variable loops is contained in a single highly variable loop (CDR-H3). In humans, this loop ranges in size from 1-35 residues (15 on average), can adopt a wide range of structural conformations, and is responsible for most of the interactions with the antigen. The other five loops are significantly less diverse and adopt only a handful of conformations. This suggests that a carefully selected "anchor" peptide can dominate the mode and strength of the interaction between a capture agent and its target protein. It also suggests that other peptide components, while providing only modest contributions to the total interaction energy, can supply important scaffolding features and specificity elements.

In situ click chemistry is a technique in which a small molecule enzymatic inhibitor is separated into two moieties, each of which is then expanded into a small library—one containing acetylene functionalities, and the other containing azide groups. The enzyme itself then assembles the 'best fit' inhibitor from these library components by selectively promoting 1,3-dipolar cycloaddition between the acetylene and azide groups to form a triazole linkage (the 'click' reaction). The protein effectively plays the role of an extremely selective variant of the Cu(I) catalyst that is commonly used for such couplings. The enzyme promotes the click reaction only between those library components that bind to the protein in the right orientation. The resultant inhibitor can exhibit far superior affinity characteristics relative to the initial inhibitor that formed the basis of the two libraries.

Sequential in situ click chemistry extends the in situ click chemistry concept to enable the discovery of multiligand capture agents (see: U.S. Application Publication No. 20100009896, incorporated herein by reference). This process was used previously to produce a triligand capture agent against the model protein carbonic anhydrase II (CAII). Sequential in situ click chemistry has several advantages. First, structural information about the protein target is replaced by the ability to sample a very large chemical space to identify the ligand components of the capture agent. For example, an initial ligand can be identified by screening the protein against a large (>106 element) one-bead-one-compound (OBOC) peptide library, where the peptides themselves can be comprised of natural, non-natural, and/or artificial amino acids. The resultant anchor ligand is then utilized in an in situ click screen, again using a large OBOC library, to identify a biligand binder. A second advantage is that the process can be repeated, so that the biligand is used as an anchor to identify a triligand, and so forth. The final capture agent can then be scaled up using relatively simple and largely automated chemistries, and it can be developed with a label, such as a biotin group, as an intrinsic part of its structure. This approach permits the exploration of branched, cyclic, and linear capture agent architectures. While many strategies for protein-directed multiligand assembly have been described, most require detailed structural information on the target to guide the screening strategy, and most (such as the original in situ click approach), are optimized for low-diversity small molecule libraries.

The disclosed compounds and methods further generalize the in situ click application to naively find an anchor ligand using in situ click. In previous approaches, a known binder was necessary to begin the ligand. This method provides a mechanism to find an anchor ligand de novo.

As described herein, an iterative in situ click chemistry approach was utilized to synthesize a biligand capture agent that specifically binds PSMA. This in situ click chemistry approach comprised two steps. First, two "anchor" ligands were found that bound PSMA at distinct but relatively close sites. Second, a linker of an appropriate size was found that bound the two ligands producing a capture agent with higher affinity for PSMA.

The capture agents generated by the methods disclosed herein were found to display binding affinity for PSMA. The capture agents were shown to function as both capture and detection agents in ELISA assays and efficiently immunoprecipitate PSMA.

1. Anchor Ligand

In some forms of the capture agent, the capture agent comprises two ligands that specifically bind PSMA at two distinct epitopes. These anchor ligands (sometimes referred to herein as simply "ligands") can then be bound to each other by a linker that provides increased affinity for PSMA. In some forms, there is a first ligand and a second ligand that bind to a first epitope and a second epitope, respectively.

According to some forms, the first epitope comprises the amino acid sequence of RTEDFFKLERDMK (SEQ ID NO:2). In some forms, the first epitope is between 5 and 20 amino acids long. In some forms, the first epitope is between 7 and 13 amino acids long. In some forms, the first epitope is at most, 5, 6, 7, 8, 9, 10, 11, 12, 13, 14, 15, 16, 17, 18, 19 or 20 amino acids long. In some forms, the second epitope comprises the amino acid sequence EYAYRRGIAEAVGLPSI (SEQ ID NO:1). In some forms, the second epitope is between 5 and 20 amino acids long. In some forms, the second epitope is between 7 and 13 amino acids long. In some forms, the second epitope is at most, 5, 6, 7, 8, 9, 10, 11, 12, 13, 14, 15, 16, 17, 18, 19 or 20 amino acids long.

According to some forms, the first epitope comprises the amino acid sequence of RTEDFFKLERDMK (SEQ ID NO:2). In some forms, the first epitope is between 5 and 20 amino acids long. In some forms, the first epitope is between 7 and 10 amino acids long. In some forms, the first epitope is at most, 5, 6, 7, 8, 9, 10, 11, 12, 13, 14, 15, 16, 17, 18, 19 or 20 amino acids long. In some forms, the second epitope comprises the amino acid sequence EYAYRRGIAEAVGLPSI (SEQ ID NO:1). In some forms, the second epitope is between 5 and 20 amino acids long. In some forms, the second epitope is between 7 and 10 amino acids long. In some forms, the second epitope is at most, 5, 6, 7, 8, 9, 10, 11, 12, 13, 14, 15, 16, 17, 18, 19 or 20 amino acids long.

In some forms, the first ligand is cyclic. In some forms, the first ligand comprises a 1,4-substituted-1,2,3-triazole residue (Tz4) or a 1,5-substituted-1,2,3-triazole residue (Tz5). In some forms, the second ligand is cyclic. In some forms, the second ligand comprises a 1,4-substituted-1,2,3-triazole residue (Tz4) or a 1,5-substituted-1,2,3-triazole residue (Tz5). In some forms, the first and second ligands are cyclic and comprise a Tz4 residue.

In some forms, the epitope comprises the amino acid sequence RTEDFFKLERDMK (SEQ ID NO:2), EYAYRRGIAEAVGLPSI (SEQ ID NO:1), TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), or GSAPPDSSWRGSLKVPYNVGPGF (SEQ ID NO:15). In some forms, the epitope comprises the amino acid sequence TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), or GSAPPDSSWRGSLKVPYNVGPGF (SEQ ID NO:15).

In some forms, the first epitope comprises the amino acid sequence RTEDFFKLERDMK (SEQ ID NO:2) or EYAYRRGIAEAVGLPSI (SEQ ID NO:1). In some forms, the first epitope comprises the amino acid sequence RTEDFFKLERDMK (SEQ ID NO:2), EYAYRRGIAEAVGLPSI (SEQ ID NO:1), TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), or GSAPPDSSWRGSLKVPYNVGPGF (SEQ ID NO:15). In some forms, the first epitope comprises the amino acid sequence TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), or GSAPPDSSWRGSLKVPYNVGPGF (SEQ ID NO:15).

In some forms, the ligand comprises an amino acid sequence 80-100% identical to an amino acid sequence selected from the group consisting of: ert, revry (SEQ ID NO:3), rdlhw (SEQ ID NO:4), drlhw (SEQ ID NO:5), lpwtr (SEQ ID NO:6), tfnkn (SEQ ID NO:7), wlsGk (SEQ ID NO:8), srdwp (SEQ ID NO:9), and hreww (SEQ ID NO:10).

In some forms, the ligand comprises an amino acid sequence 80-100% identical to an amino acid sequence selected from the group consisting of: revry (SEQ ID NO:3), hreww (SEQ ID NO:10), rdlhw (SEQ ID NO:4), drlhw (SEQ ID NO:5), ert, lpwtr (SEQ ID NO:6), tfnkn (SEQ ID NO:7), wlsGk (SEQ ID NO:8), srdwp (SEQ ID NO:9), lfkhh (SEQ ID NO:16), fGyvd (SEQ ID NO:17), ernta (SEQ ID NO:18), hnwlG (SEQ ID NO:19), wende (SEQ ID NO:20), lnhGt (SEQ ID NO:21), ehtye (SEQ ID NO:22), dwpve (SEQ ID NO:23), kwtsd (SEQ ID NO:24), svand (SEQ ID NO:25), and dntwp (SEQ ID NO:26).

In some forms, the ligand comprises an amino acid sequence 80-100% identical to an amino acid sequence selected from the group consisting of: lfkhh (SEQ ID NO:16), fGyvd (SEQ ID NO:17), ernta (SEQ ID NO:18), hnwlG (SEQ ID NO:19), wende (SEQ ID NO:20), lnhGt (SEQ ID NO:21), ehtye (SEQ ID NO:22), dwpve (SEQ ID NO:23), kwtsd (SEQ ID NO:24), svand (SEQ ID NO:25), and dntwp (SEQ ID NO:26).

In some forms, the ligand comprises an amino acid sequence 80-100% identical to an amino acid sequence selected from the group consisting of: pkvrd (SEQ ID NO:27), frvkd (SEQ ID NO:28), lynre (SEQ ID NO:29), Gydfp (SEQ ID NO:30), sfkyk (SEQ ID NO:31), dyksk (SEQ ID NO:32), wksl (SEQ ID NO:33), rkatp (SEQ ID NO:34), Grkpf (SEQ ID NO:35), kwndd (SEQ ID NO:36), eldd (SEQ ID NO:37), anGsw (SEQ ID NO:38), tkGne (SEQ ID NO:39), plntd (SEQ ID NO:40), kvetd (SEQ ID NO:41), neGfd (SEQ ID NO:42), ekfld (SEQ ID NO:43), dkkaw (SEQ ID NO:44), veyGn (SEQ ID NO:45), and eyprh (SEQ ID NO:46).

In some forms, the ligand comprises an amino acid sequence 80-100% identical to an amino acid sequence selected from the group consisting of: revry (SEQ ID NO:3), hreww (SEQ ID NO:10), rdlhw (SEQ ID NO:4), drlhw (SEQ ID NO:5), ert, lpwtr (SEQ ID NO:6), tfnkn (SEQ ID NO:7), wlsGk (SEQ ID NO:8), srdwp (SEQ ID NO:9), lfkhh (SEQ ID NO:16), fGyvd (SEQ ID NO:17), ernta (SEQ ID NO:18), hnwlG (SEQ ID NO:19), wende (SEQ ID NO:20), lnhGt (SEQ ID NO:21), ehtye (SEQ ID NO:22), dwpve (SEQ ID NO:23), kwtsd (SEQ ID NO:24), svand (SEQ ID NO:25), dntwp (SEQ ID NO:26), pkvrd (SEQ ID NO:27), frvkd (SEQ ID NO:28), lynre (SEQ ID NO:29), Gydfp (SEQ ID NO:30), sfkyk (SEQ ID NO:31), dyksk (SEQ ID NO:32), wksl (SEQ ID NO:33), rkatp (SEQ ID NO:34), Grkpf (SEQ ID NO:35), kwndd (SEQ ID NO:36), eldd (SEQ ID NO:37), anGsw (SEQ ID NO:38), tkGne (SEQ ID NO:39), plntd (SEQ ID NO:40), kvetd (SEQ ID NO:41), neGfd (SEQ ID NO:42), ekfld (SEQ ID NO:43), dkkaw (SEQ ID NO:44), veyGn (SEQ ID NO:45), and eyprh (SEQ ID NO:46).

In some forms, the ligand comprises an amino acid sequence selected from the group consisting of: revry (SEQ ID NO:3), hreww (SEQ ID NO:10), rdlhw (SEQ ID NO:4), drlhw (SEQ ID NO:5), ert, lpwtr (SEQ ID NO:6), tfnkn (SEQ ID NO:7), wlsGk (SEQ ID NO:8), srdwp (SEQ ID NO:9), lfkhh (SEQ ID NO:16), fGyvd (SEQ ID NO:17), ernta (SEQ ID NO:18), hnwlG (SEQ ID NO:19), wende (SEQ ID NO:20), lnhGt (SEQ ID NO:21), ehtye (SEQ ID NO:22), dwpve (SEQ ID NO:23), kwtsd (SEQ ID NO:24), svand (SEQ ID NO:25), and dntwp (SEQ ID NO:26).

In some forms, the ligand comprises an amino acid sequence selected from the group consisting of: lfkhh (SEQ ID NO:16), fGyvd (SEQ ID NO:17), ernta (SEQ ID NO:18), hnwlG (SEQ ID NO:19), wende (SEQ ID NO:20), lnhGt (SEQ ID NO:21), ehtye (SEQ ID NO:22), dwpve (SEQ ID NO:23), kwtsd (SEQ ID NO:24), svand (SEQ ID NO:25), and dntwp (SEQ ID NO:26).

In some forms, the ligand comprises an amino acid sequence selected from the group consisting of: pkvrd (SEQ ID NO:27), frvkd (SEQ ID NO:28), lynre (SEQ ID NO:29), Gydfp (SEQ ID NO:30), sfkyk (SEQ ID NO:31), dyksk (SEQ ID NO:32), wksl (SEQ ID NO:33), rkatp (SEQ ID NO:34), Grkpf (SEQ ID NO:35), kwndd (SEQ ID NO:36), eldd (SEQ ID NO:37), anGsw (SEQ ID NO:38), tkGne (SEQ ID NO:39), plntd (SEQ ID NO:40), kvetd (SEQ ID NO:41), neGfd (SEQ ID NO:42), ekfld (SEQ ID NO:43), dkkaw (SEQ ID NO:44), veyGn (SEQ ID NO:45), and eyprh (SEQ ID NO:46).

In some forms, the ligand comprises an amino acid sequence selected from the group consisting of: revry (SEQ ID NO:3), hreww (SEQ ID NO:10), rdlhw (SEQ ID NO:4), drlhw (SEQ ID NO:5), ert, lpwtr (SEQ ID NO:6), tfnkn (SEQ ID NO:7), wlsGk (SEQ ID NO:8), srdwp (SEQ ID NO:9), lfkhh (SEQ ID NO:16), fGyvd (SEQ ID NO:17), ernta (SEQ ID NO:18), hnwlG (SEQ ID NO:19), wende (SEQ ID NO:20), lnhGt (SEQ ID NO:21), ehtye (SEQ ID NO:22), dwpve (SEQ ID NO:23), kwtsd (SEQ ID NO:24), svand (SEQ ID NO:25), dntwp (SEQ ID NO:26), pkvrd (SEQ ID NO:27), frvkd (SEQ ID NO:28), lynre (SEQ ID NO:29), Gydfp (SEQ ID NO:30), sfkyk (SEQ ID NO:31), dyksk (SEQ ID NO:32), wksl (SEQ ID NO:33), rkatp (SEQ ID NO:34), Grkpf (SEQ ID NO:35), kwndd (SEQ ID NO:36), eldd (SEQ ID NO:37), anGsw (SEQ ID NO:38), tkGne (SEQ ID NO:39), plntd (SEQ ID NO:40), kvetd (SEQ ID NO:41), neGfd (SEQ ID NO:42), ekfld (SEQ ID NO:43), dkkaw (SEQ ID NO:44), veyGn (SEQ ID NO:45), and eyprh (SEQ ID NO:46).

In some forms, the first ligand comprises an amino acid sequence 80-100% identical to an amino acid sequence selected from the group consisting of lpwtr (SEQ ID NO:6), hnwlG (SEQ ID NO:19), wende (SEQ ID NO:20), and lnhGt (SEQ ID NO:21). In some forms, the first ligand comprises an amino acid sequence selected from the group consisting of lpwtr (SEQ ID NO:6), hnwlG (SEQ ID NO:19), wende (SEQ ID NO:20), and lnhGt (SEQ ID NO:21). In some forms, the first ligand comprises an amino acid sequence 80-100% identical to an amino acid sequence selected from the group consisting of revry (SEQ ID NO:3), rdlhw (SEQ ID NO:4), drlhw (SEQ ID NO:5), and ert. In some forms, the first ligand comprises an amino acid sequence selected from the group consisting of revry (SEQ ID NO:3), rdlhw (SEQ ID NO:4), drlhw (SEQ ID NO:5), and ert. In some forms, the first ligand comprises an amino acid sequence 80-100% identical to an amino acid sequence selected from the group consisting of lfkhh (SEQ ID NO:16), fGyvd (SEQ ID NO:17), and ernta (SEQ ID NO:18). In some forms, the first ligand comprises an amino acid sequence selected from the group consisting of lfkhh (SEQ ID NO:16), fGyvd (SEQ ID NO:17), and ernta (SEQ ID NO:18). In some forms, the first ligand comprises an amino acid sequence 80-100% identical to an amino acid sequence selected from the group consisting of hreww (SEQ ID NO:10), tfnkn (SEQ ID NO:7), wlsGk (SEQ ID NO:8), and srdwp (SEQ ID NO:9). In some forms, the first ligand comprises an amino acid sequence selected from the group consisting of hreww (SEQ ID NO:10), tfnkn (SEQ ID NO:7), wlsGk (SEQ ID NO:8), and srdwp (SEQ ID NO:9). In some forms, the first ligand comprises an amino acid sequence 80-100% identical to an amino acid sequence selected from the group consisting of ehtye (SEQ ID NO:22), dwpve (SEQ ID NO:23), kwtsd (SEQ ID NO:24), svand (SEQ ID NO:25), and dntwp (SEQ ID NO:26). In some forms, the first ligand comprises an amino acid sequence selected from the group consisting of ehtye (SEQ ID NO:22), dwpve (SEQ ID NO:23), kwtsd (SEQ ID NO:24), svand (SEQ ID NO:25), and dntwp (SEQ ID NO:26).

2. Linker

According to some forms, the capture agent further comprises a linker that binds both the first and second ligand. According to some forms, the length of the linker corresponds to distance between the first epitope and the second epitope. The length of the linker must be at least the distance between the first and second epitopes. In some forms, the linker is longer than the distance between the first and second epitopes. According to some forms, the linker is 1, 2, 3, 4, 5, 6, 7, 8, 9, 10, 20, 30, 40, 50, 60, 70, 80, 90 or 100% longer than the distance between the first and second epitopes.

According to some forms, the linker is ~4.4 Å to ~26.4 Å, ~8.8 Å to ~26.4 Å or ~7 Å to ~15 Å in length. In some forms, the length of the linker is ~15 Å.

In some forms, the linker comprises one or more repeat units of ethylene glycol. In some forms, the linker is $PEG_1$, $PEG_2$, $PEG_3$, $PEG_4$, or $PEG_5$. In some forms, the linker comprises a peptide. In some forms, the linker comprises an amino acid. In some forms, the linker is glycine. In some forms, the linker comprises an alkylene moiety, wherein the alkylene moiety is optionally substituted with one or more moieties provided herein.

3. Triazole Linkage

In some forms of the capture agent, the anchor ligand and secondary ligand are linked together via a 1,4-substituted-1,2,3-triazole residue (Tz4). In some forms, the secondary ligand and the tertiary ligand are linked together via a 1,4-substituted-1,2,3-triazole residue (Tz4). In yet some forms, the tertiary ligand and the quaternary ligand are linked together via a 1,4-substituted-1,2,3-triazole residue (Tz4). In yet some forms, the anchor ligand and secondary ligand are linked together via a 1,4-substituted-1,2,3-triazole residue, and the secondary ligand and the tertiary ligand are linked together via a 1,4-substituted-1,2,3-triazole residue. In yet some forms, the anchor ligand and secondary ligand are linked together via a 1,4-substituted-1,2,3-triazole residue, the secondary ligand and the tertiary ligand are linked together via a 1,4-substituted-1,2,3-triazole residue and the tertiary ligand and the quaternary ligand are linked together via a 1,4-substituted-1,2,3-triazole residue.

4. Second Ligands

In some forms, the second epitope comprises the amino acid sequence RTEDFFKLERDMK (SEQ ID NO:2) or EYAYRRGIAEAVGLPSI (SEQ ID NO:1). In some forms, the second epitope comprises the amino acid sequence RTEDFFKLERDMK (SEQ ID NO:2), EYAYRRGIAEAVGLPSI (SEQ ID NO:1), TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), or GSAPPDSSWRGSLKVPYNVGPGF (SEQ ID NO:15). In some forms, the second epitope comprises the amino acid sequence TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), or GSAPPDSSWRGSLKVPYNVGPGF (SEQ ID NO:15).

In some forms, the second epitope comprises the amino acid sequence EYAYRRGIAEAVGLPSI (SEQ ID NO:1). In some forms, the second epitope comprises the amino acid sequence TKKSPSPEFSGMP (SEQ ID NO:11). In some forms, the second epitope comprises the amino acid sequence YTKNWETNKFSG (SEQ ID NO:13). In some forms, the second epitope comprises the amino acid sequence RTEDFFKLERDMK (SEQ ID NO:2). In some forms, the second epitope comprises the amino acid sequence TKKSPSPEFSGMPRISKLG (SEQ ID NO:12), PADYFAPGVKSYPDGWNLPG (SEQ ID NO:14), or GSAPPDSSWRGSLKVPYNVGPGF (SEQ ID NO:15). In some forms, the second epitope comprises the amino acid sequence TKKSPSPEFSGMPRISKLG (SEQ ID NO:12). In some forms, the second epitope comprises the amino acid sequence PADYFAPGVKSYPDGWNLPG (SEQ ID NO:14). In some forms, the second epitope comprises the amino acid sequence GSAPPDSSWRGSLKVPYNVGPGF (SEQ ID NO:15).

In some forms, the second ligand comprises an amino acid sequence 80-100% identical to an amino acid sequence selected from the group consisting of lpwtr (SEQ ID NO:6), hnwlG (SEQ ID NO:19), wende (SEQ ID NO:20), and lnhGt (SEQ ID NO:21). In some forms, the second ligand comprises an amino acid sequence selected from the group consisting of lpwtr (SEQ ID NO:6), hnwlG (SEQ ID NO:19), wende (SEQ ID NO:20), and lnhGt (SEQ ID NO:21). In some forms, the second ligand comprises an amino acid sequence 80-100% identical to an amino acid sequence selected from the group consisting of revry (SEQ ID NO:3), rdlhw (SEQ ID NO:4), drlhw (SEQ ID NO:5), and ert. In some forms, the second ligand comprises an amino acid sequence selected from the group consisting of revry (SEQ ID NO:3), rdlhw (SEQ ID NO:4), drlhw (SEQ ID NO:5), and ert. In some forms, the second ligand comprises an amino acid sequence 80-100% identical to an amino acid sequence selected from the group consisting of lfkhh (SEQ ID NO:16), fGyvd (SEQ ID NO:17), and ernta (SEQ ID NO:18). In some forms, the second ligand comprises an amino acid sequence selected from the group consisting of lfkhh (SEQ ID NO:16), fGyvd (SEQ ID NO:17), and ernta (SEQ ID NO:18). In some forms, the second ligand comprises an amino acid sequence 80-100% identical to an amino acid sequence selected from the group consisting of hreww (SEQ ID NO:10), tfnkn (SEQ ID NO:7), wlsGk (SEQ ID NO:8), and srdwp (SEQ ID NO:9).

In some forms, the second ligand comprises an amino acid sequence selected from the group consisting of hreww (SEQ ID NO:10), tfnkn (SEQ ID NO:7), wlsGk (SEQ ID NO:8), and srdwp (SEQ ID NO:9). In some forms, the second ligand comprises an amino acid sequence 80-100% identical to an amino acid sequence selected from the group consisting of ehtye (SEQ ID NO:22), dwpve (SEQ ID NO:23), kwtsd (SEQ ID NO:24), svand (SEQ ID NO:25), and dntwp (SEQ ID NO:26). In some forms, the second ligand comprises an amino acid sequence selected from the group consisting of ehtye (SEQ ID NO:22), dwpve (SEQ ID NO:23), kwtsd (SEQ ID NO:24), svand (SEQ ID NO:25), and dntwp (SEQ ID NO:26).

5. Properties

In some forms, the PSMA capture agents provided herein are stable across a wide range of temperatures, pH values, storage times, storage conditions, and reaction conditions, and in some forms the capture agents are more stable than a comparable antibody or biologic. In some forms, the capture agents are stable in storage as a lyophilized powder. In some form, the capture agents are stable in storage at a temperature of about −80° C. to about 60° C. In some forms, the capture agents are stable at room temperature. In some forms, the capture agents are stable in human serum for at least 24 hours. In some forms, the capture agents are stable at a pH in the range of about 3 to about 12. In some forms, the capture agents are stable as a powder for two months at a temperature of about 60° C.

6. Detectable Labels

In some forms, the capture agent can be labeled or loaded with a label selected from the group consisting of biotin, copper-DOTA, biotin-PEG3, aminooxyacetate, $^{19}$FB, $^{18}$FB and FITC-PEG3. In some forms, the capture agent is labeled with the detectable moiety consisting of $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, $^{11}$C and $^{76}$Br. In some forms, the label is a fluorescent label. In some forms, the detectable label is $^{18}$F.

7. Methods and Uses

As used herein, the terms "disclosed capture agent" or "disclosed capture agents" refer to synthetic protein-catalyzed capture agents which bind PSMA, as described herein.

Also provided is a method of detecting PSMA in a subject, comprising the step of contacting a biological sample from the subject with one or more capture agents of the invention. Also provided is the use of one or more disclosed capture agents for the detection of PSMA in a subject.

Also provided is a method of detecting PSMA in a biological sample using an immunoassay, wherein the immunoassay utilizes a capture agent as described herein, and wherein said capture agent replaces an antibody or its equivalent in the immunoassay. In some forms, methods are provided for identifying, detecting, quantifying, or separating PSMA in a biological sample using the capture agents as described herein. In some forms of the method, the immunoassay is selected from the group of Western blot, pull-down assay, dot blot, and ELISA.

Also provided is a method of detecting the presence of PSMA in a human or mammalian subject, the method comprising the steps of:

(a) administering to a biological sample from the subject one or more capture agents, wherein each capture agent is linked to a detectable moiety; and (b) detecting the moiety linked to each capture agent in the subject; wherein detection of the moiety indicates the presence of in the subject.

Also provided herein is a method of detecting PSMA in a sample comprising:
(a) exposing the sample to one or more capture agents, wherein each capture agent is linked to a detectable moiety;
(b) binding PSMA in the biological sample to a capture agent and
(c) detecting the moiety linked to each capture agent on the substrate, wherein detection of the moiety on the substrate detects PSMA in the sample.

8. Kits

Provided herein in some forms are kits comprising one or more of the disclosed capture agents. In some forms, these kits can be used for identifying, detecting, quantifying, and/or separating PSMA, and in some forms the kits can be used in the diagnosis and/or staging of a condition associated with the presence of PSMA. In some forms, a kit as provided herein comprises: (a) a substrate comprising an adsorbent thereon, wherein the adsorbent is suitable for binding PSMA, and (b) a washing solution or instructions for making a washing solution, wherein the combination of the adsorbent and the washing solution allows detection of PSMA. In some forms, the kits provided herein can be used in the treatment of a condition associated with the presence of PSMA.

In some forms, a kit can further comprise instructions for suitable operational parameters in the form of a label or a separate insert. For example, the kit can have standard instructions informing a consumer/kit user how to wash the probe after a sample of plasma or other tissue sample is contacted on the probe. In some forms, a kit comprises (a) one or more capture agents that specifically bind PSMA; and (b) a detection reagent. Such kits can be prepared from the materials described herein.

The kits provided herein can optionally comprise a standard or control information, and/or a control amount of material, so that the test sample can be compared with the control information standard and/or control amount to determine if the test amount of PSMA detected in a sample is an amount consistent with a diagnosis of a particular condition.

9. Synthesis of Capture Agents

Provided herein are methods for making (i.e., synthesizing) PSMA-specific capture agents. In some forms, the method comprises the steps of:
(a) selecting a first ligand that binds to a first epitope on the target protein,
(b) selecting a second ligand that binds to a second epitope on the target protein,
(c) selecting a linker that has a length that allows the linker to bind both the first ligand and the second ligand when both the first and the second ligands are specifically binding the first and second epitopes, respectively, and
(d) binding the linker to the first and second ligands, thereby producing the synthetic capture agent that specifically binds to the target protein.

In some forms the ligands are identified using the following steps:
(a) a pre-clear to eliminate non-specific binders,
(b) a product screen to identify hits resulting from epitope-templated in situ click chemistry,
(c) a target screen against His-tagged PSMA protein, and
(d) another target screen against His-tagged PSMA protein in 2% (v/v) human serum to identify peptides whose binding to PSMA is unperturbed by serum proteins.

In some forms, the first epitope and the second epitope are ~4.4 Å to ~26.4 Å, ~8.8 Å to ~26.4 Å or ~7 Å to ~15 Å or ~15 Å distant from each other. In some forms, the linker is longer than the distance between the first and second epitope. Optionally, the linker is 10-50%, 5-25% or 1-10% longer than the distance between the first and second epitope.

In some forms, the capture agent has a binding affinity for the target protein greater than either of the ligands. In some forms, the capture agent has a binding affinity that is at least 50, 75 or 90% of the binding affinity of a full cooperative binder. In some forms, the capture agent has a binding affinity that is at least 1, 2, 3, 4, 5, 6, 7, 8, 9, 10, 20, 30, 40, 50, 60, 70, 80, 90, or 100% of the binding affinity of a full cooperative binder.

In some forms, the target protein is a synthetic epitope, wherein the synthetic epitope comprises at least a 20 amino acid sequence of a full length protein, wherein at least one amino acid of the synthetic epitope comprises an azide or an acetylene group. In some forms, the synthetic epitope is at least 10, 20, 30, 40, 50, 60, 70, 80, 90, 100, 110, 120, 150, 200, 250 or 300 amino acid sequence of a full length protein. In some forms, at least two amino acids of the synthetic epitope comprise an azide or an acetylene group. In some forms, at least 3, 4, 5, 6, 7, 8, 9 or 10 amino acids of the synthetic epitope comprise an azide or an acetylene group.

According to some forms, the full length protein is a naturally occurring protein. According to some forms, the naturally occurring protein is PSMA.

According to some forms, the capture agent binds the synthetic epitope and the full length protein with a binding affinity that is at least 50% of the binding affinity of a full cooperative binder. According to some forms, the capture agent binds the synthetic epitope and the full length protein with a binding affinity that is at least 1, 2, 3, 4, 5, 6, 7, 8, 9, 10, 20, 30, 40, 50, 60, 70, 80, 90, or 100% of the binding affinity of a full cooperative binder.

C. PSMA Capture Agents

In one aspect, provided herein is a stable, synthetic capture agent that specifically binds PSMA, wherein the capture agent comprises two or more "anchor" ligands (also referred to as simply "ligands" herein) and a linker and wherein the ligands selectively bind PSMA.

In some forms, a ligand comprises one or more polypeptides or peptides. In some of these forms, a target-binding moiety comprises one or more peptides comprising D-amino acids, L-amino acids, and/or amino acids substituted with functional groups selected from the group consisting of substituted and unsubstituted alkyl, substituted and unsubstituted azido, substituted and unsubstituted alkynyl, substituted and unsubstituted biotinyl, substituted and unsubstituted azioalkyl, substituted and unsubstituted polyethyleneglycolyl, and substituted and unsubstituted 1,2, 3-triazole.

In some forms, the ligands are linked to one another via a covalent linkage through a linker. In some of these forms, the ligand and linker are linked to one another via an amide bond or a 1,4-disubstituted-1,2,3-triazole linkage as shown below:

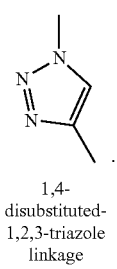

1,4-disubstituted-1,2,3-triazole linkage

In those forms where the ligands and linker are linked to one another via a 1,4-disubstituted-1,2,3-triazole linkage, the 1,4-disubstituted-1,2,3-triazole linkage can be formed by Cu-Catalyzed Azide/Alkyne Cycloaddition (CuAAC).

In some forms, the ligands and linker are linked to one another by a Tz4 linkage having the following structure:

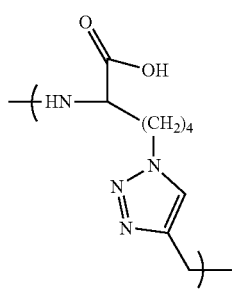

In some forms, the ligands and linker are linked to one another by a Tz5 linkage having the following structure:

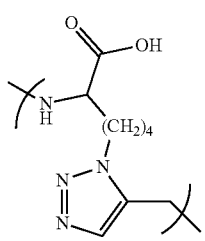

In those forms wherein one or more of the ligands and linker are linked to one another via amide bonds, the amide bond can be formed by coupling a carboxylic acid group and an amine group in the presence of a coupling agent (e.g., 0-(7-azabenzotriazol-1-yl)-N,N,N',N'-tetramethyluronium hexafluorophosphate (HATU), N-hydroxy-7-aza-benzotriazole (HOAt), or diisopropylethylamine (DIEA) in DMF).

In some forms, the capture agents provided herein are stable across a range of reaction conditions and/or storage times. A capture agent that is "stable" as used herein maintains the ability to specifically bind to a target protein. In some forms, the capture agents provided herein are more stable than an antibody binding to the same target protein under one or more reaction and/or storage conditions. For example, in some forms the capture agents provided herein are more resistant to proteolytic degradation than an antibody binding to the same target protein.

In some forms, the capture agents provided herein have a shelf-life of greater than six months, meaning that they are stable in storage for greater than six months. In some of these forms, the capture agents have a shelf-life of one year or greater, two years or greater, or more than three years. In some of these forms, the capture agents are stored as a lyophilized powder. In some forms, the capture agents provided herein have a longer shelf-life than an antibody binding to the same target protein.

In some forms, the capture agents provided herein are stable at temperatures ranging from about −80° to about 120° C. In some of these forms, the capture agents are stable within a temperature range of −80° to −40° C.; −40° to −20° C.; −20° to 0° C.; 0° to 20° C.; 20° to 40° C.; 40° to 60° C.; 60° to 80° C.; and/or 80° to 120° C. In some forms, the capture agents provided herein are stable across a wider range of temperatures than an antibody binding to the same target protein, and/or remain stable at a specific temperature for a longer time period than an antibody binding to the same target protein.

In some forms, the capture agents provided herein are stable at a pH range from about 3.0 to about 8.0. In some forms, the range is about 4.0 to about 7.0. In some forms, the range is about 7.0 to about 8.0.

In some forms, the capture agents provided herein are stable in human serum for more than 12 hours. In some of these forms, the capture agents are stable in human serum for more than 18 hours, more than 24 hours, more than 36 hours, or more than 48 hours. In some forms, the capture agents provided herein are stable for a longer period of time in human serum than an antibody binding to the same target protein. In some forms, the capture agents are stable as a powder for two months at a temperature of about 60° C. In some forms, the capture agents provided herein can comprise one or more detection labels, including for example biotin, copper-1,4,7,10-tetraazacyclododecane-1,4,7,10-tetraacetic acid (copper-DOTA), $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc. $^{110m}$In, 11C, $^{76}$Br, $^{123}$I, $^{131}$I, $^{67}$Ga, $^{111}$In and $^{99m}$Tc, or other radiolabeled products that can include gamma emitters, proton emitters, positron emitters, tritium, or covered tags detectable by other methods (i.e., gadolinium) among others. In some forms, the detection label is $^{18}$F. In some forms, the capture agents can be modified to be used as imaging agents. The imaging agents can be used as diagnostic agents.

In some forms, the capture agents provided herein can be modified to obtain a desired chemical or biological activity. Examples of desired chemical or biological activities include, without limitation, improved solubility, stability, bioavailability, detectability, or reactivity. Examples of specific modifications that can be introduced to a capture agent include, but are not limited to, cyclizing the capture agent through formation of a disulfide bond; modifying the capture agent with other functional groups or molecules. Similarly, a capture agent can be synthesized to bind to non-canonical or non-biological epitopes on proteins, thereby increasing their versatility. In some forms, the capture agent can be modified by modifying the synthesis blocks of the target-binding moieties before the coupling reaction.

Increased PSMA is associated with prostate cancer. The disclosed capture agents can be used as both a therapeutic and an imaging agent.

D. Methods of Making/Screening Capture Agents

Provided herein in some forms are methods of screening target-binding moieties and/or making capture agents that comprise these target-binding moieties. Methods for screening target-binding moieties and/or making capture agents that comprise these target-binding moieties can also be found in International Publication Nos. WO 2012/106671, WO 2013/033561, WO 2013/009869 and WO 2014/074907, each of which is incorporated by reference, herein, in their entireties.

In some forms, two separately-identified ligands that bind to two different regions of the same protein (the target) are chemically linked together to form a biligand. By optimizing a linker of the two ligands, the biligand formed by the ligands and linker can exhibit a binding affinity that is far superior to either of the individual ligands. This enhanced binding effect is called binding cooperativity. For an ideal cooperative binder, the thermodynamic binding energies of the individual ligands to the target will sum to yield the binding energy of the linked biligand. This means that the binding affinity constant ($K_D$) of the linked biligand will be the product of the binding affinity of the individual ligands (i.e. $K_D=K_{D1}\times K_{D2}$, where the subscripts 1 and 2 refer to the two ligands). In practice, full cooperative binding is rarely, if ever, achieved. Thus, a comparison of the properties of a linked biligand against those of a fully cooperative binder provides a measurement of how optimally the two ligands were linked.

If the protein target has a known and well-defined tertiary (folded) structure, then key aspects of this targeting method involve strategies for identifying ligands that bind to preferred regions of the protein, followed by approaches for identifying an optimized linker. If the protein does not have a well-defined tertiary structure, the disclosure describes strategies designed to still achieve a significant measure of cooperative binding from a biligand.

The initial goal for developing a set of PCC binders against a protein target is to identify one or more PCCs that bind to one epitope on the protein target, and one or more different PCCs binding to a second epitope. Additional PCCs that bind to a third, fourth, etc., epitope can be useful as well. In the epitope targeted PCC method, this can be accomplished by screening peptide libraries against synthetic epitopes (SynEps, also referred to as "Epitopes" herein, e.g., Epitope1, Epitope2, and Epitope3 and first epitope, second epitope, and third epitope). A SynEp is a polypeptide that has the sequence of the naturally occurring target epitope, except that one position contains an artificial amino acid that presents an azide or acetylene chemical group, called a click handle. The SynEp is further modified to contain an assay handle, such as a biotin group, at the N- or C-terminus. The screening procedure can be done using any procedure disclosed herein or known in the art. By screening, one identifies at least one unique peptide binder to each of at least two epitopes on the target. Those peptide binders are validated via carrying out binding assays against the full protein target as well as against the SynEps. For those binding assays, the SynEps are prepared with the naturally occurring residue in place of the click handle.

Ideally, the different regions of the target protein to which the different ligands bind will be relatively close together (a few nanometers or less) in the tertiary protein structure. For even a single SynEp, a screen can produce PCCs that bind to two different sites. During the SynEp screening steps, PCCs that bind to the N-terminal side of the epitope or the C-terminal side can both be identified.

Once the epitope targeted PCCs are identified, there are several methods for selecting a linker.

In some forms, if the folded structure of the protein is known, and if the PCCs bind to that folded structure, then one can use that information, plus knowledge of which PCCs bind to which epitopes, to estimate an optimal linker length. For example, one PCC can bind to the N-side of one epitope and a second PCC can bind to the C-side of a second epitope. Analysis of this binding arrangement, together with the structure of the protein from, for example, the Protein Database, permits an estimate of the length of an optimized linker. Such an estimate can narrow down the choice of candidate linkers to a very small number. One example might be to use such a length estimate to select one or two length-matched polyethylene glycol oligomers for testing. The best linker is the one that brings the biligand affinity closest to that a fully cooperative binder.

In some forms, if the folded structure of the protein is not known, or if the protein simply does not have a well-defined folded structure, then one uses as much information as is available to determine the composition of a library of candidate linker molecules. That library is then screened to identify a best linker.

In some forms, if the folded structure of the protein is not known or if the protein simply does not have a well-defined folded structure, then, using what knowledge about the protein does exist, simply select a linker to append the two PCCs. Even if an optimized, fully cooperative binder is not identified in this way, the linked biligand will almost certainly outperform either of the two monoligands because of cooperativity effects.

Peptide library screening can be performed with one or more different epitopes. When two or more different epitopes are used, some or all of the different epitopes can be used sequentially in the screening (referred to as sequential screening) (screening, for example, only the hit peptides from a prior screen in a subsequence screen), in combination (referred to as multi-ligand screening) (screening, for example, using two or more different epitopes in the same screen), or a combination of both sequential and combination screening. In some forms, the epitopes used can be two epitopes where each epitope is selected from the group consisting of amino acid sequences comprising RTEDFFKLERDMK (SEQ ID NO:2) and EYAYRRGIAEAVGLPSI (SEQ ID NO:1). In some forms, the epitopes used can be two or more epitopes where each epitope is selected from the group consisting of amino acid sequences comprising RTEDFFKLERDMK (SEQ ID NO:2), EYAYRRGIAEAVGLPSI (SEQ ID NO:1), TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15). In some forms, the epitopes used can be two or more epitopes where each epitope is selected from the group consisting of amino acid sequences comprising TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15).

In some forms, the epitopes used can be two or more epitopes where one or both of the epitopes is selected from the group consisting of amino acid sequences comprising RTEDFFKLERDMK (SEQ ID NO:2) and EYAYRRGIAEAVGLPSI (SEQ ID NO:1). In some forms, the epitopes used can be two or more epitopes where one or more of the epitopes is selected from the group consisting of amino acid sequences comprising RTEDFFKLERDMK (SEQ ID NO:2), EYAYRRGIAEAVGLPSI (SEQ ID NO:1), TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15). In some forms, the epitopes used can be two or more epitopes where one or more of the epitopes is selected from the group consisting of amino acid sequences comprising TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15).

In some forms, the screen uses two first epitopes where both of the first epitopes are selected from the group consisting of amino acid sequences comprising RTEDFFKLERDMK (SEQ ID NO:2) and EYAYRRGIAEAVGLPSI (SEQ ID NO:1). In some forms, the screen uses two or more first epitopes where each of the first epitopes comprises the amino acid sequence RTEDFFKLERDMK (SEQ ID NO:2), EYAYRRGIAEAVGLPSI (SEQ ID NO:1), TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15). In some forms, the screen uses two or more first epitopes where each of the first epitopes comprises the amino acid sequence TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15).

In some forms, the screen uses two second epitopes where both of the second epitopes are selected from the group consisting of amino acid sequences comprising RTEDFFKLERDMK (SEQ ID NO:2) and EYAYRRGIAEAVGLPSI (SEQ ID NO:1). In some forms, the screen uses two or more second epitopes where each of the second epitopes RTEDFFKLERDMK (SEQ ID NO:2), EYAYRRGIAEAVGLPSI (SEQ ID NO:1), TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15). In some forms, the screen uses two or more second epitopes where each of the second epitopes TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15).

In some forms, the screen uses two first epitopes where one or both of the first epitopes are selected from the group consisting of amino acid sequences comprising RTEDFFKLERDMK (SEQ ID NO:2) and EYAYRRGIAEAVGLPSI (SEQ ID NO:1). In some forms, the screen uses two or more first epitopes where one or more of the first epitopes comprises the amino acid sequence RTEDFFKLERDMK (SEQ ID NO:2), EYAYRRGIAEAVGLPSI (SEQ ID NO:1), TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15). In some forms, the screen uses two or more first epitopes where one or more of the first epitopes comprises the amino acid sequence TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15).

In some forms, the screen uses two second epitopes where one or both of the second epitopes are selected from the group consisting of amino acid sequences comprising RTEDFFKLERDMK (SEQ ID NO:2) and EYAYRRGIAEAVGLPSI (SEQ ID NO:1). In some forms, the screen uses two or more first epitopes where one or more of the first epitopes comprises the amino acid sequence RTEDFFKLERDMK (SEQ ID NO:2), EYAYRRGIAEAVGLPSI (SEQ ID NO:1), TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15). In some forms, the screen uses two or more first epitopes where one or more of the first epitopes comprises the amino acid sequence TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), and GSAPPDSSWRGSLKVPYNVGPGF (SEQ ID NO:15).

E. In Vitro

For detection of PSMA in solution, a capture agent can be detectably labeled, then contacted with the solution, and thereafter formation of a complex between the capture agent and the PSMA target can be detected. As an example, a fluorescently labeled capture agent can be used for in vitro PSMA detection assays, wherein the capture agent is added to a solution to be tested for PSMA under conditions allowing binding to occur. The complex between the fluorescently labeled capture agent and the PSMA target can be detected and quantified by, for example, measuring the increased fluorescence polarization arising from the complex-bound peptide relative to that of the free peptide.

Alternatively, a sandwich-type "ELISA" assay can be used, wherein a capture agent is immobilized on a solid support such as a plastic tube or well, then the solution suspected of containing PSMA is contacted with the immobilized binding moiety, non-binding materials are washed away, and complexed polypeptide is detected using a suitable detection reagent for recognizing PSMA.

For detection or purification of soluble PSMA from a solution, capture agents can be immobilized on a solid substrate such as a chromatographic support or other matrix material, then the immobilized binder can be loaded or contacted with the solution under conditions suitable for formation of a capture agent/PSMA complex. The non-binding portion of the solution can be removed and the complex can be detected, for example, using an anti-PSMA antibody, or an anti-binding polypeptide antibody, or the PSMA can be released from the binding moiety at appropriate elution conditions.

F. In Vivo Diagnostic Imaging

A particularly preferred use for the disclosed capture agents is for creating visually readable images of PSMA or PSMA-expressing cells in a biological fluid, such as, for example, in human serum. The PSMA capture agents disclosed herein can be converted to imaging reagents by conjugating the capture agents with a label appropriate for diagnostic detection. Preferably, a capture agent exhibiting much greater specificity for PSMA than for other proteins is conjugated or linked to a label appropriate for the detection methodology to be employed. For example, the capture agent can be conjugated with or without a linker to a paramagnetic chelate suitable for Magnetic Resonance Imaging (MRI), with a radiolabel suitable for x-ray, Positron Emission Tomography (PET), Single Photon Emission Computed Tomography (SPECT) or scintigraphic imaging (including a chelator for a radioactive metal), with an ultrasound contrast agent (e.g., a stabilized microbubble, a microballoon, a microsphere or what has been referred to as a gas filled "liposome") suitable for ultrasound detection, or with an optical imaging dye.

In some forms, rather than directly labeling a capture agent with a detectable label or radiotherapeutic construct, one or more of the disclosed peptides or constructs can be conjugated with for example, avidin, biotin, or an antibody or antibody fragment that will bind the detectable label or radiotherapeutic.

Also disclosed are methods for detecting PSMA in a subject, the method comprising the step of administering one or more capture agents to the subject. In some forms, at least one of the capture agents specifically binds PSMA. In some forms, PSMA is detected. In some forms, one or more of the capture agents are loaded with a detectable moiety. In some forms, the method further comprises the steps of binding PSMA to the one or more capture agents, and detecting the detectable moiety linked to the one or more capture agents. In some forms, the method further comprises the steps of binding PSMA to the one or more capture agents, and detecting the detectable moiety linked to the one or more capture agents.

1. Magnetic Resonance Imaging

The PSMA capture agents described herein can advantageously be conjugated with a paramagnetic metal chelate in order to form a contrast agent for use in MRI.

Preferred paramagnetic metal ions have atomic numbers 21-29, 42, 44, or 57-83. This includes ions of the transition metal or lanthanide series which have one, and more preferably five or more, unpaired electrons and a magnetic moment of at least 1.7 Bohr magneton. Preferred paramagnetic metals include, but are not limited to, chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III), europium (III) and ytterbium (III), chromium (III), iron (III), and gadolinium (III). The trivalent cation, Gd3+, is particularly preferred for MRI contrast agents, due to its high relaxivity and low toxicity, with the further advantage that it exists in only one biologically accessible oxidation state, which minimizes undesired metabolism of the metal by a patient. Another useful metal is Cr3+, which is relatively inexpensive. Gd(III) chelates have been used for clinical and radiologic MR applications since 1988, and approximately 30% of MRI exams currently employ a gadolinium-based contrast agent.

The paramagnetic metal chelator is a molecule having one or more polar groups that act as a ligand for, and complex with, a paramagnetic metal. Suitable chelators are known in the art and include acids with methylene phosphonic acid groups, methylene carbohydroxamine acid groups, carboxyethylidene groups, or carboxymethylene groups. Examples of chelators include, but are not limited to, diethylenetriaminepentaacetic acid (DTPA), 1,4,7,10-tetraazacyclo-tetra-decane-1,4,7,10-tetraacetic acid (DOTA), 1-substituted 1,4,7,-tricarboxymethyl-1,4,7,10-teraazacyclododecane (DO3A), ethylenediaminetetraacetic acid (EDTA), and 1,4,8,11-tetra-azacyclotetradecane-1,4,8,11-tetraacetic acid (TETA). Additional chelating ligands are ethylene bis-(2-hydroxy-phenylglycine) (EHPG), and derivatives thereof, including 5-Cl-EHPG, 5-Br-EHPG, 5-Me-EHPG, 5-t-Bu-EHPG, and 5-sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl DTPA; bis-2 (hydroxybenzyl)-ethylene-diaminediacetic acid (HBED) and derivatives thereof; the class of macrocyclic compounds which contain at least 3 carbon atoms, more preferably at least 6, and at least two heteroatoms (0 and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N''-triacetic acid, benzo-TETA, benzo-DOTMA, where DOTMA is 1,4,7,10-tetraazacyclotetradecane-1,4,7,10-tetra(methyl tetraacetic acid), and benzo-TETMA, where TETMA is 1,4,8,11-tetraazacyclotetradecane-1,4,8,11-(methyl tetraacetic acid); derivatives of 1,3-propylene-diaminetetraacetic acid (PDTA) and triethylenetetraaminehexaacetic acid (TTNA); derivatives of 1,5,10-N,N',N''-tris(2,3-dihydroxybenzoyl)-tricatecholate (LICAM); and 1,3,5-N,N',N''-tris(2,3-dihydroxybenzoyl)aminomethylbenzene (MECAM). A preferred chelator for use with the disclosed compounds and methods is DTPA, and the use of DO3A is particularly preferred. Examples of representative chelators and chelating groups for such use are described in WO 98/18496, WO 86/06605, WO 91/03200, WO 95/28179, WO 96/23526, WO 97/36619, PCT/US98/01473, PCT/US98/20182, and U.S. Pat. Nos. 4,899,755, 5,474,756, 5,846,519 and 6,143,274, all of which are hereby incorporated by reference.

In some forms, the chelator of the MRI contrast agent is coupled to the PSMA capture agent. The positioning of the chelate should be selected so as not to interfere with the binding affinity or specificity of the PSMA capture agent. The chelate also can be attached anywhere on the capture agent.

In general, the PSMA capture agent can be bound directly or covalently to the metal chelator (or other detectable label), or it can be coupled or conjugated to the metal chelator using a linker, which can be, without limitation, amide, urea, acetal, ketal, double ester, carbonyl, carbamate, thiourea, sulfone, thioester, ester, ether, disulfide, lactone, imine, phosphoryl, or phosphodiester linkages; substituted or unsubstituted saturated or unsaturated alkyl chains; linear, branched, or cyclic amino acid chains of a single amino acid or different amino acids (e.g., extensions of the N- or C-terminus of the PSMA binding moiety); derivatized or underivatized polyethylene glycols (PEGs), polyoxyethylene, or polyvinylpyridine chains; substituted or unsubstituted polyamide chains; derivatized or underivatized polyamine, polyester, polyethylenimine, polyacrylate, poly (vinyl alcohol), polyglycerol, or oligosaccharide (e.g., dextran) chains; alternating block copolymers; malonic, succinic, glutaric, adipic and pimelic acids; caproic acid; simple diamines and dialcohols; any of the other linkers disclosed herein; or any other simple polymeric linkers known in the art (see, for example, WO 98/18497 and WO 98/18496). Preferably the molecular weight of the linker can be tightly controlled. The molecular weights can range in size from less than 100 to greater than 1000. Preferably the molecular weight of the linker is less than 100. In addition, it can be desirable to utilize a linker that is biodegradable in vivo to provide efficient routes of excretion for the disclosed imaging reagents. Depending on their location within the linker, such biodegradable functionalities can include ester, double ester, amide, phosphoester, ether, acetal, and ketal functionalities.

In general, known methods can be used to couple the metal chelate and the PSMA capture agent using such linkers (WO 95/28967, WO 98/18496, WO 98/18497 and discussion therein). The PSMA binding moiety can be linked through an N- or C-terminus via an amide bond, for example, to a metal coordinating backbone nitrogen of a metal chelate or to an acetate arm of the metal chelate itself. The present disclosure contemplates linking of the chelate on any position, provided the metal chelate retains the ability to bind the metal tightly in order to minimize toxicity.

MRI contrast reagents prepared according to the disclosures herein can be used in the same manner as conventional MRI contrast reagents. Certain MR techniques and pulse sequences can be preferred to enhance the contrast of the site to the background blood and tissues. These techniques include (but are not limited to), for example, black blood angiography sequences that seek to make blood dark, such as fast spin echo sequences (Alexander, A. et al., 1998. Magn. Reson. Med., 40: 298-310) and flow-spoiled gradient echo sequences (Edelman, R. et al., 1990. Radiology, 177: 45-50). These methods also include flow independent techniques that enhance the difference in contrast, such as inversion-recovery prepared or saturation-recovery prepared sequences that will increase the contrast between PSMA-expressing tissue and background tissues. Finally, magnetization transfer preparations also can improve contrast with these agents (Goodrich, K. et al., 1996. Invest. Radia, 31: 323-32).

The labeled reagent is administered to the patient in the form of an injectable composition. The method of administering the MRI contrast agent is preferably parenterally, meaning intravenously, intraarterially, intrathecally, interstitially, or intracavitarilly. For imaging PSMA-expressing tissues, such as tumors, intravenous or intraarterial administration is preferred. For MRI, it is contemplated that the subject will receive a dosage of contrast agent sufficient to enhance the MR signal at the site of PSMA expression by at least 10%. After injection with the PSMA capture agent containing MRI reagent, the patient is scanned in the MRI machine to determine the location of any sites of PSMA expression. In therapeutic settings, upon identification of a site of PSMA expression (e.g., fluid or tissue), an anti-cancer agent (e.g., inhibitors of PSMA) can be immediately administered, if necessary, and the patient can be subsequently scanned to visualize viral load.

2. Nuclear Imaging (Radionuclide Imaging) and Radiotherapy

The disclosed PSMA capture agents can be conjugated with a radionuclide reporter appropriate for scintigraphy, SPECT, or PET imaging and/or with a radionuclide appropriate for radiotherapy. Also contemplated are constructs in which the PSMA capture agents are conjugated with both a chelator for a radionuclide useful for diagnostic imaging and a chelator useful for radiotherapy.

For use as a PET agent a disclosed capture agent can be complexed with one of the various positron emitting metal ions, such as $^{51}$Mn, $^{52}$Fe, $^{60}$Cu, $^{68}$Ga, $^{72}$As, $^{94m}$Tc, or $^{110}$In. The disclosed binding moieties (e.g., capture agents) can also be labeled by halogenation using radionuclides such as $^{18}$F, $^{124}$I, $^{125}$I, $^{131}$I, $^{123}$I, $^{77}$Br, and $^{76}$Br. Preferred metal radionuclides for scintigraphy or radiotherapy include $^{99m}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{177}$Lu, $^{198}$Au and $^{199}$Au. The choice of metal will be determined based on the desired therapeutic or diagnostic application. For example, for diagnostic purposes the preferred radionuclides include $^{64}$Cu, $^{67}$Ga, $^{68}$Ga, $^{99m}$Tc, and $^{111}$In. For therapeutic purposes, the preferred radionuclides include $^{64}$Cu, $^{90}$Y, $^{105}$Rh, $^{111}$In, $^{117m}$Sn, $^{149}$Pm, $^{153}$Sm, $^{161}$Tb, $^{166}$Tb, $^{166}$Dy, $^{166}$Ho, $^{175}$Yb, $^{177}$Ln, $^{186/188}$Re, and $^{199}$Au. $^{99m}$Tc is useful for diagnostic applications because of its low cost, availability, imaging properties, and high specific activity. The nuclear and radioactive properties of 99mTc make this isotope an ideal scintigraphic imaging agent. This isotope has a single photon energy of 140 keV and a radioactive half-life of about 6 hours, and is readily available from a $^{99}$Mo-$^{99m}$Tc generator. $^{18}$F, 4-[$^{18}$F]fluorobenzaldehyde ($^{18}$FB), Al[$^{18}$F]-NOTA, $^{68}$Ga-DOTA, and $^{68}$Ga-NOTA are typical radionuclides for conjugation to PSMA capture agents for diagnostic imaging. The metal radionuclides can be chelated by, for example, linear, macrocyclic, terpyridine, and $N_3S$, $N_2S_2$, or $N_4$ chelants (see also, U.S. Pat. Nos. 5,367,080, 5,364,613, 5,021,556, 5,075, 099, 5,886,142), and other chelators known in the art including, but not limited to, HYNIC, DTPA, EDTA, DOTA, DO3A, TETA, NOTA and bisamino bisthiol (BAT) chelators (see also U.S. Pat. No. 5,720,934). For example, N.sub.4 chelators are described in U.S. Pat. Nos. 6,143,274; 6,093,382; 5,608,110; 5,665,329; 5,656,254; and 5,688,487. Certain N.sub.35 chelators are described in PCT/CA94/00395, PCT/CA94/00479, PCT/CA95/00249 and in U.S. Pat. Nos. 5,662,885; 5,976,495; and 5,780,006. The chelator also can include derivatives of the chelating ligand mercapto-acetyl-acetyl-glycyl-glycine (MAG3), which contains an $N_3S$, and $N_2S_2$ systems such as MAMA (monoamidemonoaminedithiols), DADS ($N_2S$ diaminedithiols), CODADS and the like. These ligand systems and a variety of others are described in, for example, Liu, S, and Edwards, D., 1999. Chem. Rev., 99:2235-2268, and references therein.

The chelator also can include complexes containing ligand atoms that are not donated to the metal in a tetradentate array. These include the boronic acid adducts of technetium and rhenium dioximes, such as are described in U.S. Pat. Nos. 5,183,653; 5,387,409; and 5,118,797, the disclosures of which are incorporated by reference herein, in their entirety.

The chelators can be covalently linked directly to the PSMA capture agent via a linker, as described previously, and then directly labeled with the radioactive metal of choice (see, WO 98/52618, U.S. Pat. Nos. 5,879,658, and 5,849,261).

PSMA capture agents comprising $^{18}$F, 4-[$^{18}$F]fluorobenzaldehyde ($^{18}$FB), Al[$^{18}$F]-NOTA, $^{68}$Ga-DOTA, and $^{68}$Ga-NOTA are of preferred interest for diagnostic imaging. Complexes of radioactive technetium are also useful for diagnostic imaging, and complexes of radioactive rhenium are particularly useful for radiotherapy. In forming a complex of radioactive technetium with the disclosed reagents (e.g., capture agents), the technetium complex, preferably a salt of $^{99m}$Tc pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent to be labeled and a sufficient amount of reducing agent to label the reagent with $^{99m}$Tc. Alternatively, the complex can be formed by reacting a peptide conjugated with an appropriate chelator with a pre-formed labile complex of technetium and another compound known as a transfer ligand. This process is known as ligand exchange and is well known to those skilled in the art. The labile complex can be formed using such transfer ligands as tartrate, citrate, gluconate or mannitol, for example. Useful $^{99m}$Tc pertechnetate salts include the alkali metal salts such as the sodium salt, or ammonium salts or lower alkyl ammonium salts.

Preparation of the disclosed complexes where the metal is radioactive rhenium can be accomplished using rhenium starting materials in the +5 or +7 oxidation state. Examples of compounds in which rhenium is in the Re(VII) state are $NH_4ReO_4$ or $KReO_4$. Re(V) is available as, for example, $[ReOCl_4](NBu_4)$, $[ReOC_4](AsPh_4)$, $ReOCl_3(PPh_3)_2$ and as $ReO_2(pyridine)^{4+}$, where Ph is phenyl and Bu is n-butyl. Other rhenium reagents capable of forming a rhenium complex also can be used.

Radioactively labeled PET, SPECT, or scintigraphic imaging agents described herein preferably have a suitable amount of radioactivity. Generally, the unit dose to be administered has a radioactivity of about 0.01 mCi to about 100 mCi, preferably 1 mCi to 20 mCi. The solution to be injected at unit dosage is from about 0.01 mL to about 10 mL. It is generally preferred to form radioactive complexes in solutions containing radioactivity at concentrations of from about 0.01 mCi to 100 mCi per mL.

Typical doses of a radionuclide-labeled PSMA capture agent can provide 10-20 mCi. After injection of the radionuclide-labeled PSMA capture agents into the patient, a gamma camera calibrated for the gamma ray energy of the nuclide incorporated in the imaging agent is used to image areas of uptake of the agent and quantify the amount of radioactivity present in the site. Imaging of the site in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos.

Proper dose schedules for the disclosed radiotherapeutic compounds are known to those skilled in the art. The compounds can be administered using many methods including, but not limited to, a single or multiple IV or IP injections, using a quantity of radioactivity that is sufficient to cause damage or ablation of the targeted PSMA-expressing tissue, but not so much that substantive damage is caused to non-target (normal tissue). The quantity and dose required is different for different constructs, depending on the energy and half-life of the isotope used, the degree of uptake and clearance of the agent from the body and the mass of the PSMA-expressing tissue. In general, doses can range from a single dose of about 30-50 mCi to a cumulative dose of up to about 3 Ci.

The disclosed radiotherapeutic compositions can include physiologically acceptable buffers, and can require radiation stabilizers to prevent radiolytic damage to the compound prior to injection. Radiation stabilizers are known to those skilled in the art, and can include, for example, para-aminobenzoic acid, ascorbic acid, gentistic acid and the like.

Also disclosed are single, or multi-vial kits that contain all of the components needed to prepare the disclosed complexes, other than the radionuclide.

A single-vial kit preferably contains a chelating ligand, a source of stannous salt, or other pharmaceutically acceptable reducing agent, and is appropriately buffered with pharmaceutically acceptable acid or base to adjust the pH to a value of about 3 to about 9. The quantity and type of reducing agent used would depend on the nature of the exchange complex to be formed. The proper conditions are well known to those that are skilled in the art. It is preferred that the kit contents be in lyophilized form. Such a single vial kit can optionally contain labile or exchange ligands such as glucoheptonate, gluconate, mannitol, malate, citric or tartaric acid and can also contain reaction modifiers such as diethylenetriamine-pentaacetic acid (DPTA), ethylenediamine tetraacetic acid (EDTA), or α, β, or γ cyclodextrin that serve to improve the radiochemical purity and stability of the final product. The kit also can contain stabilizers, bulking agents such as mannitol, that are designed to aid in the freeze-drying process, and other additives known to those skilled in the art.

A multi-vial kit preferably contains the same general components but employs more than one vial in reconstituting the radiopharmaceutical. For example, one vial can contain all of the ingredients that are required to form a labile Tc(V) complex on addition of pertechnetate (e.g., the stannous source or other reducing agent). Pertechnetate is added to this vial, and after waiting an appropriate period of time, the contents of this vial are added to a second vial that contains the ligand, as well as buffers appropriate to adjust the pH to its optimal value. After a reaction time of about 5 to 60 minutes, the complexes are formed. It is advantageous that the contents of both vials of this multi-vial kit be lyophilized. As above, reaction modifiers, exchange ligands, stabilizers, bulking agents, etc. can be present in either or both vials.

Also provided herein is a method to incorporate an 18F radiolabeled prosthetic group onto an PSMA capture agent. In some forms, 4-[$^{18}$F]fluorobenzaldehyde ($^{18}$FB) is conjugated onto a capture agent bearing an aminooxy moiety, resulting in oxime formation. In some forms, [$^{18}$F]fluorobenzaldehyde is conjugated onto a capture agent bearing an acyl hydrazide moiety, resulting in a hydrazone adduct. 4-Fluorobenzaldehyde, can be prepared in $^{18}$F form by displacement of a leaving group, using $^{18}$F ion, by known methods. $^{18}$F-labeled capture agents can also be prepared from capture agents possessing thiosemicarbazide moieties under conditions that promote formation of a thiosemicarbozone, or by use of a $^{18}$F-labeled aldehyde bisulfite addition complex.

The above methods are particularly amenable to the labeling of capture agents, e.g., the capture agents described herein, which can be modified during synthesis to contain a nucleophilic hydroxylamine, thiosemicarbazide or hydrazine (or acyl hydrazide) moiety that can be used to react with the labeled aldehyde. The methods can be used for any capture agent that can accommodate a suitable nucleophilic moiety. Typically the nucleophilic moiety is appended to the N-terminus of the peptide, but the skilled artisan will recognize that the nucleophile also can be linked to an amino acid side chain or to the peptide C-terminus. Methods of synthesizing a radiolabeled peptide sequence are provided in which 4-[$^{18}$F]fluorobenzaldehyde is reacted with a peptide sequence comprising either a hydroxylamine, a thiosemicarbazide or a hydrazine (or acyl hydrazide) group, thereby forming the corresponding oximes, thiosemicarbazones or hydrazones, respectively. The 4-[$^{18}$F]fluorobenzaldehyde typically is generated in situ by the acid-catalyzed decomposition of the addition complex of 4-[$^{18}$F]fluorobenzaldehyde and sodium bisulfite. The use of the bisulfite addition complex enhances the speed of purification since, unlike the aldehyde, the complex can be concentrated to dryness. Formation of the complex is also reversible under acidic and basic conditions. In particular, when the complex is contacted with a peptide containing a hydroxylamine, a thiosemicarbazide or a hydrazine (or acyl hydrazide) group in acidic medium, the reactive free 4-[$^{18}$F]fluorobenzaldehyde is consumed as it is formed in situ, resulting in the corresponding $^{18}$F radiolabeled peptide sequence.

In the instances when the oxime, thiosemicarbazone or hydrazone linkages present in vivo instability, an additional reduction step can be employed to reduce the double bond connecting the peptide to the $^{18}$F bearing substrate. The corresponding reduced peptide linkage would enhance the stability. One of skill in the art would appreciate the variety of methods available to carry out such a reduction step. Reductive amination steps as described in Wilson et al., Journal of Labeled Compounds and Radiopharmaceuticals, XXVIII (10), 1189-1199, 1990 can also be used to form a Schiff's base involving a peptide and 4-[$^{18}$F]fluorobenzaldehyde and directly reducing the Schiff's base using reducing agents such as sodium cyanoborohydride.

The 4-[$^{18}$F]fluorobenzaldehyde can be prepared as described in Wilson et al., Journal of Labeled Compounds and Radiopharmaceuticals, XXVIII (10), 1189-1199, 1990; Iwata et al., Applied radiation and isotopes, 52, 87-92, 2000; Poethko et al., The Journal of Nuclear Medicine, 45, 892-902, 2004; and Schottelius et al., Clinical Cancer Research, 10, 3593-3606, 2004. The Na$^{18}$F in water can be added to a mixture of kryptofix and $K_2CO_3$. Anhydrous acetonitrile can be added and the solution evaporated in a heating block under a stream of argon. Additional portions of acetonitrile can be added and evaporated to completely dry the sample. The 4-trimethylammoniumbenzaldehyde triflate can be dissolved in DMSO and added to the dried F-18. The solution can then be heated in the heating block. The solution can be cooled briefly, diluted with water and filtered through a Waters®. Oasis HLB LP extraction cartridge. The cartridge can be washed with 9:1 water:acetonitrile and water to remove unbound $^{18}$F and unreacted 4-trimethylammoniumbenzaldehyde triflate. The 4-[$^{18}$F]fluorobenzaldehyde can then be eluted from the cartridge with methanol in fractions.

G. Therapeutic Applications

Provided herein in some forms are methods of using the PSMA capture agents disclosed herein to identify, detect, quantify, and/or separate PSMA in a biological sample. In some forms, these methods utilize an immunoassay, with the capture agent replacing an antibody or its equivalent. In some forms, the immunoassay can be a Western blot, pull-down assay, dot blot, or ELISA.

A biological sample for use in the methods provided herein can be selected from the group consisting of organs, tissue, bodily fluids, and cells. Where the biological sample is a bodily fluid, the fluid can be selected from the group consisting of blood, serum, plasma, urine, sputum, saliva, stool, spinal fluid, cerebral spinal fluid, lymph fluid, skin secretions, respiratory secretions, intestinal secretions, genitourinary tract secretions, tears, and milk. The organs include, e.g., the adrenal glands, bladder, bones, brain, breasts, cervix, esophagus, eyes, gall bladder, genitals, heart, kidneys, large intestine, liver, lungs, lymph nodes, ovaries, pancreas, pituitary gland, prostate, salivary glands, skeletal muscles, skin, small intestine, spinal cord, spleen, stomach, thymus gland, trachea, thyroid, testes, ureters, and urethra. Tissues include, e.g., epithelial, connective, nervous, and muscle tissues.

Provided herein in some forms are methods of using the PSMA capture agents disclosed herein to diagnose and/or classify (e.g., stage) a condition associated with PSMA expression. In some of these forms, the methods comprise (a) obtaining a biological sample from a subject; (b) measuring the presence or absence of PSMA in the sample with the PSMA capture agent; (c) comparing the levels of PSMA to a predetermined control range for PSMA; and (d) diagnosing a condition associated with PSMA expression based on the difference between PSMA levels in the biological sample and the predetermined control.

In some forms, the PSMA capture agents disclosed herein are used as a mutant specific targeted therapeutic. In some forms, the PSMA capture agent is administered alone without delivering DNA, a radiopharmaceutical or another active agent.

The disclosed PSMA capture agents also can be used to target genetic material to PSMA-expressing cells. The genetic material can include nucleic acids, such as RNA or DNA, of either natural or synthetic origin, including recombinant RNA and DNA and antisense RNA and DNA. Types of genetic material that can be used include, for example, genes carried on expression vectors such as plasmids, phagemids, cosmids, yeast artificial chromosomes (YACs) and defective or "helper" viruses, antigene nucleic acids, both single and double stranded RNA and DNA and analogs thereof, such as phosphorothioate and phosphorodithioate oligodeoxynucleotides. Additionally, the genetic material can be combined, for example, with lipids, proteins or other polymers. Delivery vehicles for genetic material can include, for example, a virus particle, a retroviral or other gene therapy vector, a liposome, a complex of lipids (especially cationic lipids) and genetic material, a complex of dextran derivatives and genetic material, etc.

In some forms, the disclosed capture agents can be utilized in gene therapy. In some forms, genetic material, or one or more delivery vehicles containing genetic material can be conjugated to one or more PSMA capture agents of this disclosure and administered to a patient.

Therapeutic agents and the PSMA capture agents disclosed herein can be linked or fused in known ways, optionally using the same type of linkers discussed elsewhere in this application. Preferred linkers will be substituted or unsubstituted alkyl chains, amino acid chains, polyethylene glycol chains, and other simple polymeric linkers known in the art. More preferably, if the therapeutic agent is itself a protein, for which the encoding DNA sequence is known, the therapeutic protein and PSMA binding polypeptide can be coexpressed from the same synthetic gene, created using recombinant DNA techniques, as described above. The coding sequence for the PSMA binding polypeptide can be fused in frame with that of the therapeutic protein, such that the peptide is expressed at the amino- or carboxy-terminus of the therapeutic protein, or at a place between the termini, if it is determined that such placement would not destroy the required biological function of either the therapeutic protein or the PSMA binding polypeptide. A particular advantage of this general approach is that concatamerization of multiple, tandemly arranged PSMA capture agents is possible, thereby increasing the number and concentration of PSMA binding sites associated with each therapeutic protein. In this manner, PSMA binding avidity is increased, which would be expected to improve the efficacy of the recombinant therapeutic fusion protein.

Also disclosed are methods for treating a subject in need thereof, the method comprising the step of administering one or more capture agents to the subject, where the subject has a disease or condition that can be targeted via PSMA. In some forms, the disease of condition is cancer. In some forms, at least one of the capture agents specifically binds PSMA. In some forms, one or more of the capture agents are loaded with a therapeutic moiety.

The disclosed biligands can be produced using a one-bead-one-compound (OBOC) library of alkyne-appended macrocycle peptides screened against the target SynEp appending an azide and a biotin detection label. In this system, those peptides that bind to the SynEp in just the right orientation are covalently coupled through a click reaction between azide and alkyne. After thoroughly washing to remove non-covalently bound copies of the SynEp, the beads are treated with alkaline phosphatase (AP)-conjugated streptavidin. Hit beads are visualized using BCIP/NBT and picked for sequencing. Hits are scaled up and tested against the full-length protein to identify the best binders.

The disclosed compositions and methods can be further understood through the following numbered paragraphs.

1. A theranostic capture agent for a target, the capture agent comprising two or more ligands covalently linked to each other, wherein the ligands specifically bind to one of two or more distinct epitopes of a target that are in different locations on the target, wherein the capture agent is (a) a precursor that can be loaded with a detectable moiety, a therapeutic moiety, or both, (b) loaded with a detectable moiety, (c) loaded with a therapeutic moiety, or (d) loaded with both a detectable moiety and a therapeutic moiety.

2. The capture agent of paragraph 1, wherein the capture agent comprises a first of the ligands that has affinity for a first of the epitopes, a second of the ligands that has affinity for a second of the epitopes, and a linker covalently connecting the first ligand to the second ligand.

3. The capture agent of paragraph 2, wherein the capture agent includes a loading moiety that can be or is loaded with a detectable moiety, a therapeutic moiety, or both.

4. The capture agent of paragraph 3, wherein the loading moiety is DOTA or NOTA

5. The capture agent of paragraph 3 or 4, wherein the loading moiety is (a) unloaded, (b) loaded with a detectable moiety, (c) loaded with a therapeutic moiety, or (d) loaded with both a detectable moiety and a therapeutic moiety.

6. The capture agent of any one of paragraphs 3-5, wherein the loading moiety is loaded with a detectable moiety.

7. The capture agent of any one of paragraphs 3-5, wherein the capture agent is loaded with a detectable moiety.

8. The capture agent of any one of paragraphs 1-7, wherein the detectable moiety is selected from the group consisting of biotin, copper, biotin-PEG3, aminooxyacetate, $^{19}$FB, $^{18}$FB and FITC-PEG$_3$.

9. The capture agent of paragraph 6 or 7, wherein the detectable moiety is selected from the group consisting of Al$^{18}$F, $^{18}$F, $^{68}$Ga, $^{64}$Cu, $^{68}$Ga, $^{89}$Zr, $^{124}$I, $^{86}$Y, $^{94m}$Tc, $^{110m}$In, $^{11}$C, and $^{76}$Br.

10. The capture agent of any one of paragraphs 3-9, wherein the loading moiety is loaded with a therapeutic moiety.

11. The capture agent of any one of paragraphs 1-9, wherein the capture agent is loaded with a therapeutic moiety.

12. The capture agent of any one of paragraphs 1-11, wherein the therapeutic moiety is selected from the group consisting of $^{177}$Lu, $^{99m}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{198}$Au and $^{199}$Au.

13. The capture agent of paragraph 11 or 12, wherein the therapeutic moiety is selected from the group consisting of $^{177}$Lu, $^{99m}$Tc, $^{51}$Cr, $^{67}$Ga, $^{68}$Ga, $^{47}$Sc, 51Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{198}$Au and $^{199}$Au.

14. The capture agent of any one of paragraphs 1-13, wherein the capture agent binds PSMA.

15. The capture agent of paragraph 14, wherein the first epitope is an epitope on PSMA, wherein the first ligand has affinity for the epitope on PSMA.

16. The capture agent of paragraph 14 or 15, wherein the second epitope is an epitope on PSMA, wherein the second ligand has affinity for the epitope on PSMA.

17. The capture agent of any one of paragraphs 14-16, wherein the capture agent specifically binds PSMA.

18. The capture agent of any one of paragraphs 14-17, wherein the first epitope comprises the amino acid sequence RTEDFFKLERDMK (SEQ ID NO:2), EYAYRRGI-AEAVGLPSI (SEQ ID NO:1), TKKSPSPEFSGMP (SEQ ID NO:11), TKKSPSPEFSGMPRISKLG (SEQ ID NO:12), YTKNWETNKFSG (SEQ ID NO:13), PADYFAPGVKSYPDGWNLPG (SEQ ID NO:14), or GSAPPDSSWRGSLKVPYNVGPGF (SEQ ID NO:15).

19. The capture agent of any one of paragraphs 14-18, wherein the first ligand comprises an amino acid sequence 80-100% identical to an amino acid sequence selected from the group consisting of revry (SEQ ID NO:3), hreww (SEQ ID NO:10), rdlhw (SEQ ID NO:4), drlhw (SEQ ID NO:5), ert, lpwtr (SEQ ID NO:6), tfnkn (SEQ ID NO:7), wlsGk (SEQ ID NO:8), srdwp (SEQ ID NO:9), lfkhh (SEQ ID NO:16), fGyvd (SEQ ID NO:17), ernta (SEQ ID NO:18), hnwlG (SEQ ID NO:19), wende (SEQ ID NO:20), lnhGt (SEQ ID NO:21), ehtye (SEQ ID NO:22), dwpve (SEQ ID NO:23), kwtsd (SEQ ID NO:24), svand (SEQ ID NO:25), and dntwp (SEQ ID NO:26).

20. The capture agent of any one of paragraphs 14-18, wherein the first ligand comprises an amino acid sequence 80-100% identical to an amino acid sequence selected from the group consisting of pkvrd (SEQ ID NO:27), frvkd (SEQ ID NO:28), lynre (SEQ ID NO:29), Gydfp (SEQ ID NO:30), sfkyk (SEQ ID NO:31), dyksk (SEQ ID NO:32), wksl (SEQ ID NO:33), rkatp (SEQ ID NO:34), Grkpf (SEQ ID NO:35), kwndd (SEQ ID NO:36), eldd (SEQ ID NO:37), anGsw (SEQ ID NO:38), tkGne (SEQ ID NO:39), plntd (SEQ ID NO:40), kvetd (SEQ ID NO:41), neGfd (SEQ ID NO:42), ekfld (SEQ ID NO:43), dkkaw (SEQ ID NO:44), veyGn (SEQ ID NO:45), and eyprh (SEQ ID NO:46).

21. The capture agent of any one of paragraphs 14-18, wherein the first ligand comprises an amino acid sequence selected from the group consisting of revry (SEQ ID NO:3), hreww (SEQ ID NO:10), rdlhw (SEQ ID NO:4), drlhw (SEQ ID NO:5), ert, lpwtr (SEQ ID NO:6), tfnkn (SEQ ID NO:7), wlsGk (SEQ ID NO:8), srdwp (SEQ ID NO:9), lfkhh (SEQ ID NO:16), fGyvd (SEQ ID NO:17), ernta (SEQ ID NO:18), hnwlG (SEQ ID NO:19), wende (SEQ ID NO:20), lnhGt (SEQ ID NO:21), ehtye (SEQ ID NO:22), dwpve (SEQ ID NO:23), kwtsd (SEQ ID NO:24), svand (SEQ ID NO:25), and dntwp (SEQ ID NO:26).

22. The capture agent of any one of paragraphs 14-18, wherein the first ligand comprises an amino acid sequence selected from the group consisting of pkvrd (SEQ ID NO:27), frvkd (SEQ ID NO:28), lynre (SEQ ID NO:29), Gydfp (SEQ ID NO:30), sfkyk (SEQ ID NO:31), dyksk (SEQ ID NO:32), wksl (SEQ ID NO:33), rkatp (SEQ ID NO:34), Grkpf (SEQ ID NO:35), kwndd (SEQ ID NO:36), eldd (SEQ ID NO:37), anGsw (SEQ ID NO:38), tkGne (SEQ ID NO:39), plntd (SEQ ID NO:40), kvetd (SEQ ID NO:41), neGfd (SEQ ID NO:42), ekfld (SEQ ID NO:43), dkkaw (SEQ ID NO:44), veyGn (SEQ ID NO:45), and eyprh (SEQ ID NO:46).

23. The capture agent of paragraph 15, wherein the first ligand comprises the structure

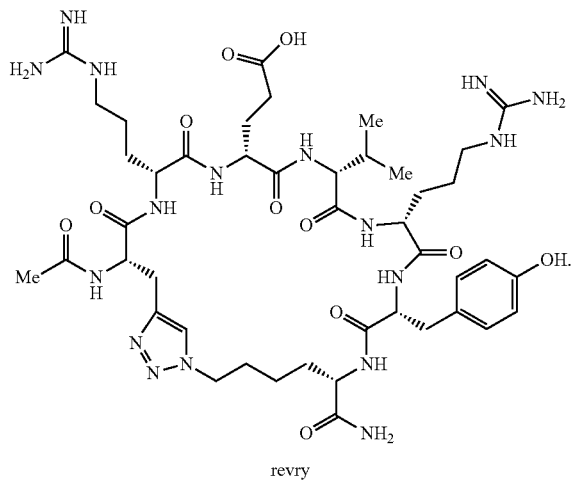 [SMILES: CC(=O)N[C@H]1Cc2cn(nn2)CCCC[C@@H](C(N)=O)NC(=O)[C@@H](Cc2ccc(O)cc2)NC(=O)[C@@H](CCCNC(=N)N)NC(=O)[C@@H](C(C)C)NC(=O)[C@@H](CCC(=O)O)NC(=O)[C@@H](CCCNC(=N)N)NC1=O]

revry

24. The capture agent of paragraph 15, wherein the first ligand comprises the structure

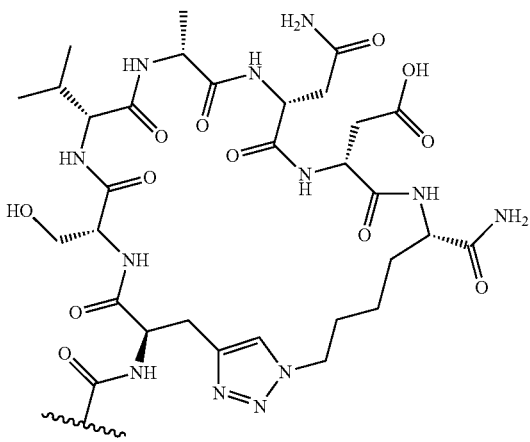 [SMILES: *C(=O)N[C@@H]1Cc2cn(nn2)CCCC[C@@H](C(N)=O)NC(=O)[C@@H](CC(=O)O)NC(=O)[C@@H](CC(N)=O)NC(=O)[C@@H](C)NC(=O)[C@@H](C(C)C)NC(=O)[C@@H](CO)NC1=O]

25. The capture agent of any one of paragraphs 15-22, wherein the second epitope comprises the amino acid sequence EYAYRRGIAEAVGLPSI (SEQ ID NO:1).

26. The capture agent of paragraph 25, wherein the second ligand comprises an amino acid sequence 80-100% identical to an amino acid sequence selected from the group consisting of lpwtr (SEQ ID NO:6), hnwlG (SEQ ID NO:19), wende (SEQ ID NO:20), and lnhGt (SEQ ID NO:21).

27. The capture agent of paragraph 25, wherein the second ligand comprises an amino acid sequence selected from the group consisting of lpwtr (SEQ ID NO:6), hnwlG (SEQ ID NO:19), wende (SEQ ID NO:20), and lnhGt (SEQ ID NO:21).

28. The capture agent of any one of paragraphs 15-24, wherein the second epitope comprises the amino acid sequence TKKSPSPEFSGMP (SEQ ID NO:11).

29. The capture agent of paragraph 28, wherein the second ligand comprises an amino acid sequence 80-100% identical to an amino acid sequence selected from the group consisting of revry (SEQ ID NO:3), rdlhw (SEQ ID NO:4), drlhw (SEQ ID NO:5), and ert.

30. The capture agent of paragraph 28, wherein the second ligand comprises an amino acid sequence selected from the group consisting of revry (SEQ ID NO:3), rdlhw (SEQ ID NO:4), drlhw (SEQ ID NO:5), and ert.

31. The capture agent of any one of paragraphs 15-22, wherein the second epitope comprises the amino acid sequence YTKNWETNKFSG (SEQ ID NO:13).

32. The capture agent of paragraph 31, wherein the second ligand comprises an amino acid sequence 80-100% identical to an amino acid sequence selected from the group consisting of lfkhh (SEQ ID NO:16), fGyvd (SEQ ID NO:17), and ernta (SEQ ID NO:18).

33. The capture agent of paragraph 31, wherein the second ligand comprises an amino acid sequence selected from the group consisting of lfkhh (SEQ ID NO:16), fGyvd (SEQ ID NO:17), and ernta (SEQ ID NO:18).

34. The capture agent of any one of paragraphs 15-22, wherein the second epitope comprises the amino acid sequence RTEDFFKLERDMK (SEQ ID NO:2).

35. The capture agent of paragraph 34, wherein the second ligand comprises an amino acid sequence 80-100% identical to an amino acid sequence selected from the group consisting of hreww (SEQ ID NO:10), tfnkn (SEQ ID NO:7), wlsGk (SEQ ID NO:8), and srdwp (SEQ ID NO:9).

36. The capture agent of paragraph 34, wherein the second ligand comprises an amino acid sequence selected from the group consisting of hreww (SEQ ID NO:10), tfnkn (SEQ ID NO:7), wlsGk (SEQ ID NO:8), and srdwp (SEQ ID NO:9).

37. The capture agent of any one of paragraphs 15-22, wherein the second epitope comprises the amino acid sequence TKKSPSPEFSGMPRISKLG (SEQ ID NO:12), PADYFAPGVKSYPDGWNLPG (SEQ ID NO:14), or GSAPPDSSWRGSLKVPYNVGPGF (SEQ ID NO:15).

38. The capture agent of paragraph 37, wherein the second ligand comprises an amino acid sequence 80-100% identical to an amino acid sequence selected from the group consisting of ehtye (SEQ ID NO:22), dwpve (SEQ ID NO:23), kwtsd (SEQ ID NO:24), svand (SEQ ID NO:25), and dntwp (SEQ ID NO:26).

39. The capture agent of paragraph 37, wherein the second ligand comprises an amino acid sequence selected from the group consisting of ehtye (SEQ ID NO:22), dwpve (SEQ ID NO:23), kwtsd (SEQ ID NO:24), svand (SEQ ID NO:25), and dntwp (SEQ ID NO:26).

40. The capture agent of any one of paragraphs 15-22, wherein the second epitope comprises the amino acid sequence TKKSPSPEFSGMPRISKLG (SEQ ID NO:12).

41. The capture agent of any one of paragraphs 15-22, wherein the second epitope comprises the amino acid sequence PADYFAPGVKSYPDGWNLPG (SEQ ID NO:14).

42. The capture agent of any one of paragraphs 15-22, wherein the second epitope comprises the amino acid sequence GSAPPDSSWRGSLKVPYNVGPGF (SEQ ID NO:15).

43. The capture agent of any one of paragraphs 2-42, wherein the first ligand is cyclic.

44. The capture agent of any one of paragraphs 2-43, wherein the first ligand comprises a 1,4-substituted-1,2,3-triazole residue (Tz4) or a 1,5-substituted-1,2,3-triazole residue (Tz5).

45. The capture agent of paragraph 44, wherein the first ligand comprises a 1,4-substituted-1,2,3-triazole residue (Tz4).

46. The capture agent of paragraph 44, wherein the first ligand comprises a 1,5-substituted-1,2,3-triazole residue (Tz5).

47. The capture agent of any one of paragraphs 2-46, wherein the second ligand is cyclic.

48. The capture agent of any one of paragraphs 2-47, wherein the second ligand comprises a 1,4-substituted-1,2,3-triazole residue (Tz4) or a 1,5-substituted-1,2,3-triazole residue (Tz5).

49. The capture agent of paragraph 48, wherein the second ligand comprises a 1,4-substituted-1,2,3-triazole residue (Tz4).

50. The capture agent of paragraph 48, wherein the second ligand comprises a 1,5-substituted-1,2,3-triazole residue (Tz5).

51. The capture agent of any one of paragraphs 2-50, wherein the linker is divalent.

52. The capture agent of any one of paragraphs 2-51, wherein the length of the linker corresponds to distance between the first epitope and the second epitope.

53. The capture agent of any one of paragraphs 2-52, wherein the length of the linker is from ~4.4 Å to ~26.4 Å, from ~8.8 Å to ~26.4 Å or from ~7 Å to ~15 Å.

54. The capture agent of any one of paragraphs 2-53, wherein the length of the linker is ~15 Å.

55. The capture agent of any one of paragraphs 2-54, wherein the linker comprises one or more repeat units of ethylene glycol.

56. The capture agent of paragraph 55, wherein the linker is selected from the group consisting of $PEG_1$, $PEG_2$, $PEG_3$, $PEG_4$ and $PEG_5$.

57. The capture agent of any one of paragraphs 2-54, wherein the linker comprises a peptide.

58. The capture agent of paragraph 57, wherein the linker is glycine.

59. A method for detecting PSMA in a biological sample, the method comprising the step of contacting the biological sample with one or more capture agents of paragraph 1-58.

60. The method of paragraph 59, wherein at least one of the capture agents specifically binds PSMA.

61. The method of paragraph 59, wherein PSMA is detected.

62. The method of paragraph 59, wherein one or more of the capture agents are loaded with a detectable moiety.

63. The method of paragraph 62 further comprising the steps of binding PSMA to the one or more capture agents, and detecting the detectable moiety linked to the one or more capture agents.

64. The method of paragraph 62 further comprising the steps of binding PSMA to the one or more capture agents, and detecting the detectable moiety linked to the one or more capture agents.

65. A method for detecting PSMA in a subject, the method comprising the step of administering one or more capture agents of paragraph 1-58 to the subject.

66. The method of paragraph 65, wherein at least one of the capture agents specifically binds PSMA.

67. The method of paragraph 65, wherein PSMA is detected.

68. The method of paragraph 65, wherein one or more of the capture agents are loaded with a detectable moiety.

69. The method of paragraph 65 further comprising the steps of binding PSMA to the one or more capture agents, and detecting the detectable moiety linked to the one or more capture agents.

70. The method of paragraph 65 further comprising the steps of binding PSMA to the one or more capture agents, and detecting the detectable moiety linked to the one or more capture agents.

71. A method for treating a subject in need thereof, the method comprising the step of administering one or more capture agents of paragraph 1-58 to the subject, wherein the subject has a disease or condition that can be targeted via PSMA.

72. The method of paragraph 71, wherein the disease of condition is cancer.

73. The method of paragraph 71, wherein at least one of the capture agents specifically binds PSMA.

74. The method of paragraph 71, wherein one or more of the capture agents are loaded with a therapeutic moiety.

75. The method of paragraph 74, wherein one or more of the one or more capture agents are loaded with a detectable moiety.

76. The method of paragraph 74, wherein one or more of the one or more capture agents loaded with the therapeutic moiety are also loaded with a detectable moiety.

77. The method of paragraph 74 further comprising administering one or more additional capture agents to the subject, wherein one or more of the one or more additional capture agents are loaded with a detectable moiety.

78. The method of paragraph 77, wherein one or more of the one or more additional capture agents are administered at or near the same time as, or together with, one or more of the capture agents are administered.

79. The method of paragraph 77 or 78, wherein one or more of the one or more additional capture agents are administered at a different time than one or more of the capture agents are administered.

EXAMPLES

Example 1: Use of PCC Ligands in Theranostics

Capture agents (e.g., PCCs) are useful in theranostics. The specific binding of capture agents allow them to target and home to targets in a subject. By combining such a capture agent with a detectable agent, a therapeutic agent, or both, it can provide both diagnostic/detection and therapeutic effects.

Prostate-specific membrane antigen (PSMA) was used as the first target to demonstrate the use of capture agents in theranostics. PSMA is a cell surface protein with overexpression in prostate cancer. PSMA expression increases progressively in higher grade tumors, hormone-refractory prostate cancer, and metastatic disease. The substrate is internalized after binding, which results in enhanced uptake, deposit, and retention in tumor. This, in turn, provides high imaging quality for diagnosis and high local dose for (radio) therapeutics. Capture agents specific for PSMA provide new and selected binding sites, providing new feature and functions for capture agent-based theranostics.

The active site of PSMA is accessible on the extracellular portion of PSMA, as is the binding site of J591 antibody (Maurer T et al, Nat Rev Urol, 12:226-235 (2016)). The binding site of 7E11 antibody is on the intracellular portion of PSMA.

PET imaging with $^{18}F$ probes are used to target PSMA in prostate cancer patients. $^{68}Ga$ can work for imaging, but cost and convenience makes $^{18}F$ labeled probes a better choice. Examples of PSMA ligands for use in PET imaging include $^{68}Ga$-PSMA-11 (Eder et al., Biocojugate Chem. 23(4):688-97 (2012)), $^{68}G$-PSMA-617 (Benesova et al., JNM 56(6): 914-20 (2015)), $^{68}G$-PSMA I&T (Weineisen et al., JNM 56(8):1169-76 (2015)), $^{18}F$-DCEBC (Cho et al., JNM 53:1883-1891 (2012)), $^{18}F$-DCFPyL (Szabo et al., Mol. Imaging Biol. 17(4):565-74 (2015)), $^{18}F$-PSMA-1007 (Cardinale et al., JNM 58(3):425-431 (2017); Giesel et al., EJNMMI 44(4): 678-688 (2016)). All of these include a basic moiety (glutamate-urea-lysine or glutamate-urea-cysteine).

As an example, [68]G-PSMA I&T has the structure:

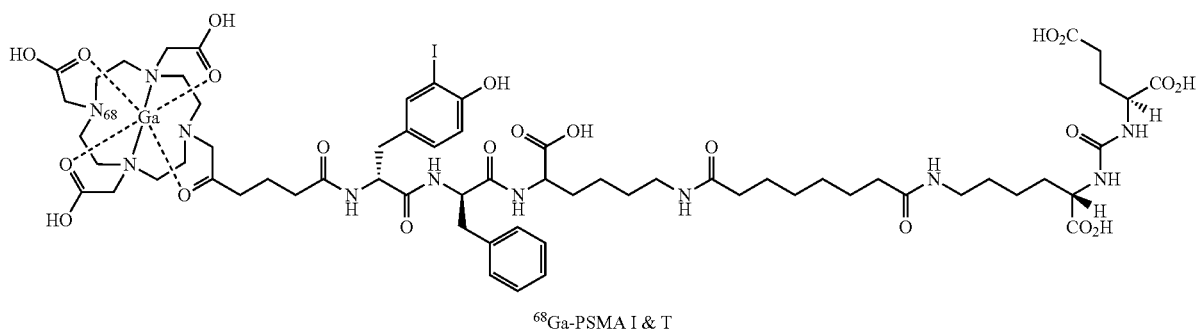

[68]Ga-PSMA I & T

This class of PSMA ligands generally rely on active site recognition and use hydrophobic additions to increase affinity. These PSMA ligands bind or interact with, for example, the arene-binding site, the arginine patch, and the glutamate pocket of PSMA (Kopka et al., JNM 58(Suppl 2):17S-26S (2017)).

Capture agents for PET imaging have been prepared by fluorination of a PCC with [18]F. For example, a PCC can be labeled with 4-[$^{18}$F]FBA:

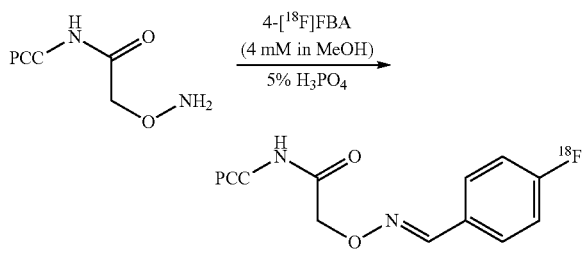

A different moiety and different attachment chemistry would be needed to add a therapeutic moiety. To embody both detection and therapeutic effect (i.e., theranostic) in the same base structure, we developed the use of a chelation moiety that can chelate either a PET-detectable radiolabel (e.g., [68]G, $^{18}$F) and a therapeutic radiolabel (e.g., $^{177}$Lu, $^{90}$Y).

Development of capture agent theranostics was demonstrated by producing capture agents that bind to PSMA and including both a detectable moiety and a therapeutic moiety, either together or alternatively. The general structure of these initial capture agent theranostics is shown in FIG. 1, which shows a single PCC ligand as the capture agent. The capture agent can alternatively be a multiligand PCC. In this example, the detectable moiety and therapeutic moiety are chelated to a chelation moiety.

Epitopes chosen for targeting in PCC screening are shown in Table 1. The bold, underlined amino acid is the amino acid replace with an amino acid that includes a click chemistry handle, which thus differentiates epitope 2A and 2B and epitope 3A and 3B.

TABLE 1

|  | Epitope 2A/2B | Epitope 3A/3B | Epitope 4 | Epitope 5 |
|---|---|---|---|---|
| Sequence | [T498-P510]<br>2A: TKKSPSPEFSGMP<br>2B: TKKSPSPEFSGMP<br>SEQ ID NO: 11 | [Y537-G548]<br>3A: YTKNWETNKFSG<br>3B: YTKNWETNKFSG<br>SEQ ID NO: 13 | [E276-I292]<br>EYAYRRGIAEA-<br>VGLPSI<br>SEQ ID NO: 1 | [R181-K193]<br>RTEDFFKLERDMK<br>SEQ ID NO: 2 |
| Total Surface Area | 1601.951 Å2 | 1590.582 Å$^2$ | 1926.545 Å$^2$ | 1937.435 |
| Solvent Accessible Surface Area | 1069.872 Å$^2$ | 766.401 Å$^2$ | 1108.787 Å$^2$ | 1017.91 |
| Net Charge | +1 | +1 | 0 | 0 |
| Average Backbone RMSD | 1.059<br>(0.153) | 1.060<br>(0.360) | 1.793 Å<br>(0.555) | 1.587 Å<br>(0.502) |
| Average RMSD (includes side chains) | 1.428<br>(0.382) | 1.428<br>(0.382) | 1.911 Å<br>(0.482) | 1.628 Å<br>(0.470) |

Epitopes 2A/2B are two related epitopes that are near the PSMA active site. The Az4 placement within epitope 2A is near the center of the epitope, allowing for PCCs to target either the C or N terminus of the sequence. For epitope 2B, the click handle is placed near the C terminus of the sequence, directing PCC recognition near this portion of the epitope. Epitopes 4 and 5 are sequences contained within the putative binding location of J591, the first clinical PSMA antibody. Epitope 4 is located on the opposite face of the active site of PSMA. Epitope 5 is positioned directly above the active site, and is close enough to allow for biligand conjugation (~20 Å away from epitope 3).

Figure 9:
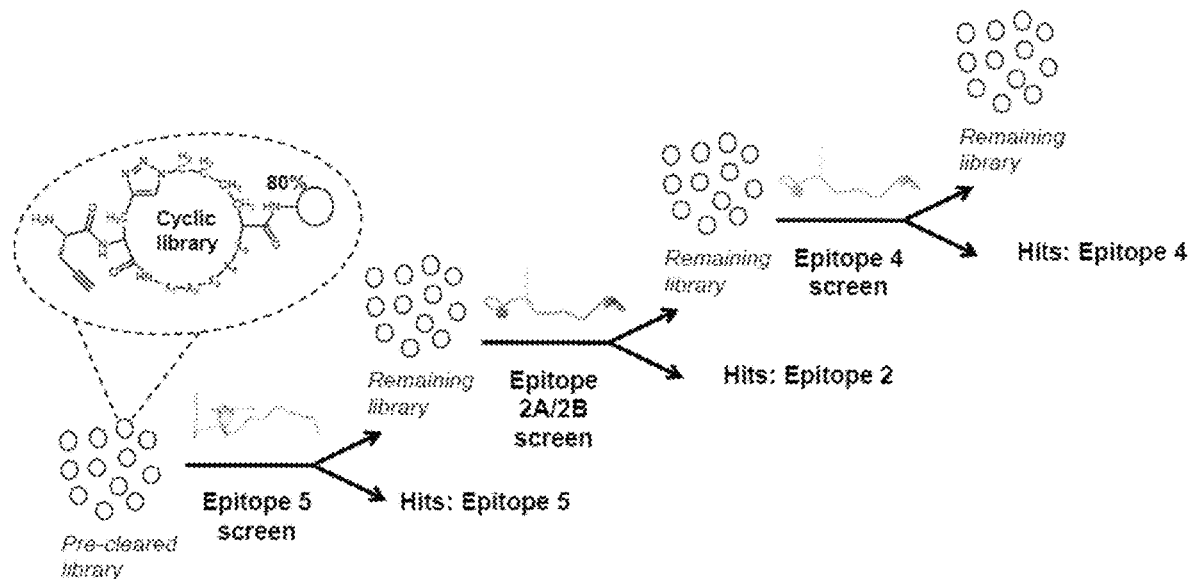
FIG. 9 is a diagram showing an example of sequential screening using epitopes 5, 2A/2B, and 4.

FIG. 9 shows the strategy used to screen for ligands to three different epitopes of PSMA. This is an illustration of sequential epitope screening.

A cyclic peptide library with a variable peptide region, a biotin moiety, and a click chemistry handle was first pre-cleared to remove peptides that non-specifically bind. The first screen is against epitope 5, which is contained within the putative binding site of the J591 antibody. The epitope has the complementary click chemistry handle to the peptide library so that when a peptide in the library binds to the epitope so that the click chemistry handles are in proximity and in the correct orientation the peptide and the epitope are coupled. This has the effect of joining the biotin label to epitope so that the hit peptides can be identified and separated. In FIG. 9 this is shown as the epitope 5 hits separate from the remaining library. The epitope 5 hits are shown in Table 2 (hreww (SEQ ID NO:10), tfnkn (SEQ ID NO:7), wlsGk (SEQ ID NO:8), srdwp (SEQ ID NO:9)).

TABLE 2

|      | x1 | x2 | x3 | x4 | x5 |
|------|----|----|----|----|----|
| hit1 | t  | f  | n  | k  | n  |
| hit2 | w  | l  | s  | G  | k  |
| hit3 | s  | r  | d  | w  | p  |
| hit4 | h  | r  | e  | w  | w  |

This remaining library, which is depleted of peptides that bind epitope 5, was then screened against epitope 2A/2B, which is in close proximity to the PSMA active site. The 2A/2B epitope has the complementary click chemistry handle to the peptide library so that when a peptide in the library binds to the epitope so that the click chemistry handles are in proximity and in the correct orientation the peptide and the epitope are coupled. This has the effect of joining the biotin label to epitope so that the hit peptides can be identified and separated. In FIG. 9 this is shown as the epitope 2A/2B hits separate from the remaining library. The epitope 2A/2B hits are shown in Table 3 (ert, revry (SEQ ID NO:3), rdlhw (SEQ ID NO:4), drlhw (SEQ ID NO:5)).

TABLE 3

|      | x1 | x2 | x3 | x4 | x5 |
|------|----|----|----|----|----|
| hit1 | e  | r  | t  |    |    |
| hit2 | r  | e  | v  | r  | y  |
| hit3 | r  | d  | l  | h  | w  |
|      | d  | r  | l  | h  | w  |

This remaining library, which is depleted of peptides that bind epitope 5 and that bind epitope 2A/2B, was then screened against epitope 4, which is contained within the putative binding site of the J591 antibody. The 4 epitope has the complementary click chemistry handle to the peptide library so that when a peptide in the library binds to the epitope so that the click chemistry handles are in proximity and in the correct orientation the peptide and the epitope are coupled. This has the effect of joining the biotin label to epitope so that the hit peptides can be identified and separated. In FIG. 9 this is shown as the epitope 4 hits separate from the remaining library. The epitope 4 hits are shown in Table 4 (lpwtr (SEQ ID NO:6)).

TABLE 4

|      | x1 | x2 | x3 | x4 | x5 |
|------|----|----|----|----|----|
| hit1 | l  | p  | w  | t  | r  |

In this example, epitopes 5, 2A/2B, and 4 were screened sequentially. Four hits were identified against epitope 5. The clear beads were subjected to a click screen against epitopes 2A/2B, which identified four unique hits. These hits have good sequence homology, with polar and/or charged residues dominating. Only one hit was identified that targeted epitope 4.

Epitope 5 hits were tested for binding to PSMA by ELISA (PSMA immobilized; PCC titrated in solution). Two immobilization strategies were employed: a His-tag and Myc-Flag tag (His-PSMA (Sino Biological) and PSMA-Myc-Flag (Origene)). Regardless of the immobilization orientation, hreww (SEQ ID NO:10) showed good binding to PSMA (His-PSMA: $EC_{50}$=871.6 nM. PSMA-Myc-Flag: $EC_{50}$=662.5 nM). The three other sequences demonstrated poor binding to PSMA regardless of how the protein was immobilized.

One epitope 2 hit, revry (SEQ ID NO:3), was docked against the equilibrated PSMA structure. The lowest energy binding mode suggests that revry (SEQ ID NO:3) binds to epitope 2 just outside the active site of PSMA. The close proximity to the active site enables the attachment of a zinc binder to yield a heterobiligand.

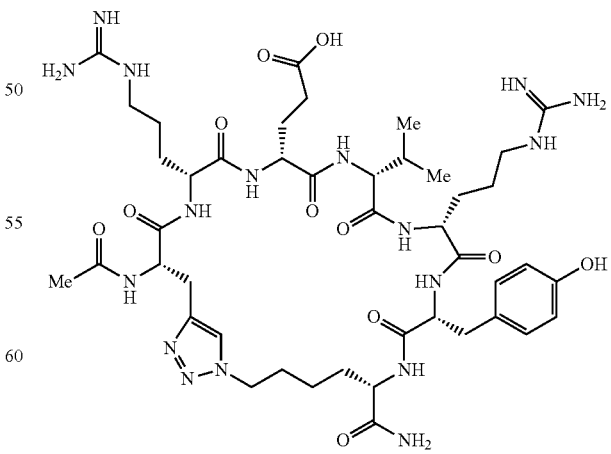

revry

Examples of zinc binders include:

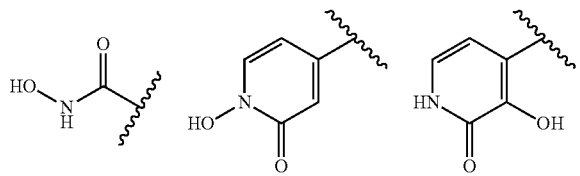 [SMILES: *C(=O)NO ; *c1ccn(O)c(=O)c1 ; *c1cc[nH]c(=O)c1O]

Hits resulting from the epitope 2 screen were also profiled by ELISA and flow. Binding against recombinant PSMA suggested good binding of the ert dimer (PEG10-ert-Tz-ert; EC50=768.9 nM). When assayed in a cellular context, the ert dimer showed binding in LNCaP cells (PSMA+) as well as PC3 (PSMA−) cells; ert (monomer) did not show binding to LNCaP or PC3 cells.

Figure 10:
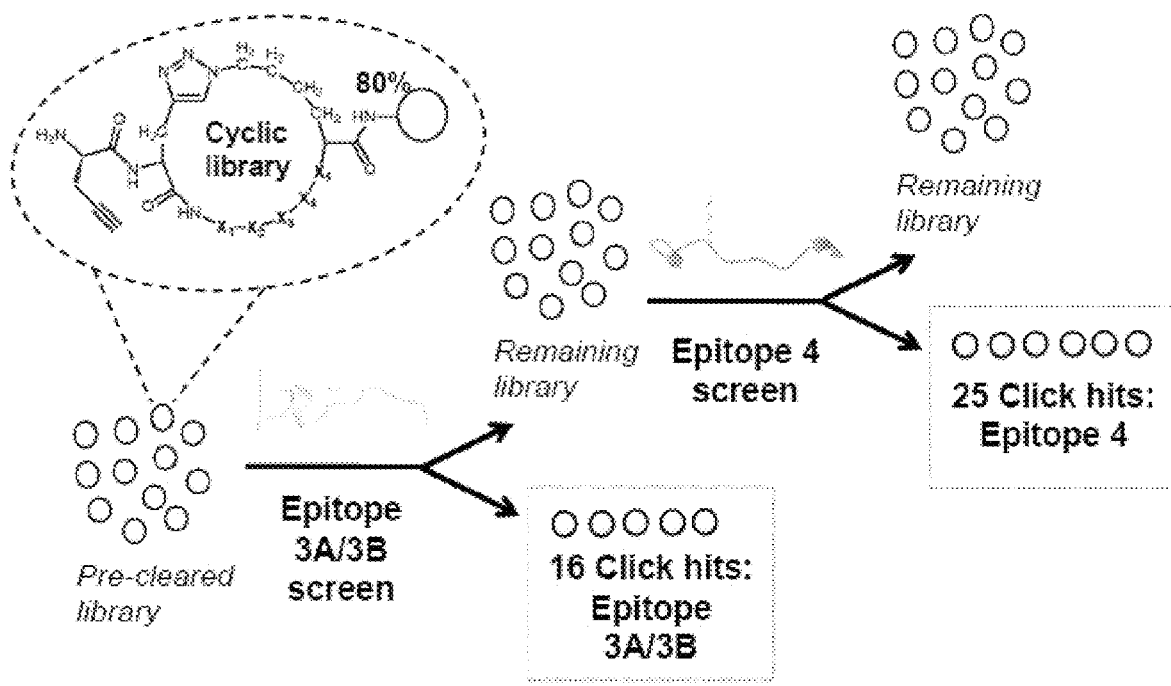
FIG. 10 is a diagram showing an example of sequential screening using epitopes 3A/3B and 4.

FIG. 10 shows the strategy used to screen for ligands to three different epitopes of PSMA. This is another illustration of sequential epitope screening. A cyclic peptide library with a variable peptide region, a biotin moiety, and a click chemistry handle was first pre-cleared to remove peptides that non-specifically bind. The first screen is against epitope 3A/3B, which is in close proximity to the PSMA active site. The epitope has the complementary click chemistry handle to the peptide library so that when a peptide in the library binds to the epitope so that the click chemistry handles are in proximity and in the correct orientation the peptide and the epitope are coupled. This has the effect of joining the biotin label to epitope so that the hit peptides can be identified and separated. 16 hits were identified and separated from the remaining library. These hits were then screened against the target protein PSMA. This produced three hits, which are shown in Table 5 (lfkhh (SEQ ID NO:16), fGyvd (SEQ ID NO:17), ernta (SEQ ID NO:18)).

TABLE 5

|      | x1 | x2 | x3 | x4 | x5 |
|------|----|----|----|----|----|
| hit1 | l  | f  | k  | h  | h  |
| hit2 | f  | G  | y  | v  | d  |
| hit3 | e  | r  | n  | t  | a  |

The remaining library, which is depleted of peptides that bind epitope 3A/3B, was then screened against epitope 4, which is in close proximity to the PSMA active site. The 4 epitope has the complementary click chemistry handle to the peptide library so that when a peptide in the library binds to the epitope so that the click chemistry handles are in proximity and in the correct orientation the peptide and the epitope are coupled. This has the effect of joining the biotin label to epitope so that the hit peptides can be identified and separated. 25 hits were identified and separated from the remaining library. These hits were then screened against the target protein PSMA. This produced three hits, which are shown in Table 6 (hnwlG (SEQ ID NO:19), wende (SEQ ID NO:20), lnhGt (SEQ ID NO:21)).

TABLE 6

|      | x1 | x2 | x3 | x4 | x5 |
|------|----|----|----|----|----|
| hit1 | h  | n  | w  | l  | G  |
| hit2 | w  | e  | n  | d  | e  |
| hit3 | l  | n  | h  | G  | t  |

Hits resulting from the epitope 3 screen were scaled up and subjected to ELISA and flow experiments. By ELISA, lfkhh (SEQ ID NO:16) bound strongly to PSMA (EC50=8.6 nM). The other hits were less potent, with binding affinities in the micromolar range. In flow, lfkhh (SEQ ID NO:16) bound equally to LNCap and PC3 cells, suggesting some non-specificity in the compound.

Hits resulting from the epitope 4 screen were also profiled in ELISA and flow cytometry. Only hnwlG (SEQ ID NO:19) showed modest binding by ELISA (EC50=5585 nM). No hit showed good PSMA binding in a cellular context.

Further epitopes chosen for targeting in PCC screening are shown in Table 7. The bold, underlined amino acid is the amino acid replace with an amino acid that includes a click chemistry handle.

TABLE 7

|                                      | Epitope 2C                                              | Epitope 6                                            | Epitope 7                                              |
|--------------------------------------|---------------------------------------------------------|------------------------------------------------------|--------------------------------------------------------|
| Sequence                             | [T498-G516] TKKSPSPEFSGM-PRISKLG SEQ ID NO: 12      | [P231-G250] CPADYFAPGVKSYPDG-WNLPGC SEQ ID NO: 47 | [G311-F333] CGSAPPDSSWRGSLKVPY-NVGPGFC SEQ ID NO: 48 |
| Total Surface Area                   | 2424.995 Å$^2$                                          | 2310.988 Å$^2$                                       | 2791.497 Å$^2$                                         |
| Solvent Accessible Surface Area      | 1307.707 Å$^2$                                          | 1053.848 Å$^2$                                       | 1379.497 Å$^2$                                         |
| Net Charge                           | +3                                                      | −1                                                   | +1                                                     |
| Backbone RMSD                        | 0.721 Å (0.156)                                         | 1.338 Å (0.312)                                      | 1.519 Å (0.347)                                        |
| Side Chain RMSD                      | 1.059 Å (0.153)                                         | 1.588 Å (0.354)                                      | 1.714 Å (0.352)                                        |

Three additional epitopes of PSMA were screened. Epitope 2 was lengthened to include additional PSMA surface. This epitope (2C) is also located near the PSMA active site. The proximity to the active site may explain the low RMSD values for this epitope, suggesting that the backbone is more structured during the molecular dynamics simulation. This design element enables the attachment of a small molecule PSMA binder to the PCC construct, providing a PSMA heterobiligand. Within the context of the protein, this epitope remains more rigid than other portions of the protein. It also has a high net charge. Epitope 6 and 7 are cyclic epitopes that are cyclized using a disulfide linkage. While the inclusion of the bis-cysteines are not found naturally in the PSMA sequence, the conformational restrictions of this cyclic epitope may lead to a higher hit rate. Epitopes 6 and 7 also overlap the putative binding site of J591, the PSMA monoclonal antibody that is in the clinic. The click handles of these epitopes are separated by 13 Å, indicating that a biligand strategy is feasible. The N and C termini of both epitopes are stapled via a cysteine disulfide to reduce conformational flexibility of the synthetic epitope.

Related constrained epitopes are epitope 6b (GC-PADYFAPGVKSYPDGWNLPGCG (SEQ ID NO:49)) and epitope 7b (GCGSAPPDSSWRGSLKVPYNVGPGFCG (SEQ ID NO:50)) (not yet used for screening). Epitope 6b is P231-G250 of PSMA, has a total surface area of 2310.988 Å$^2$, a solvent accessible surface of 1053.848 Å$^2$, a net charge of −1, average backbone RMSD of 1.338 (0.312), and average RMSD (including side chains) of 1.588 (0.354). Epitope 7b is G311-F333 of PSMA, has a total surface area of 2791.497 Å$^2$, a solvent accessible surface of 1379.497 Å$^2$, a net charge of +1, average backbone RMSD of 1.519 (0.347), and average RMSD (including side chains) of 1.714 (0.352).

Figure 11A:
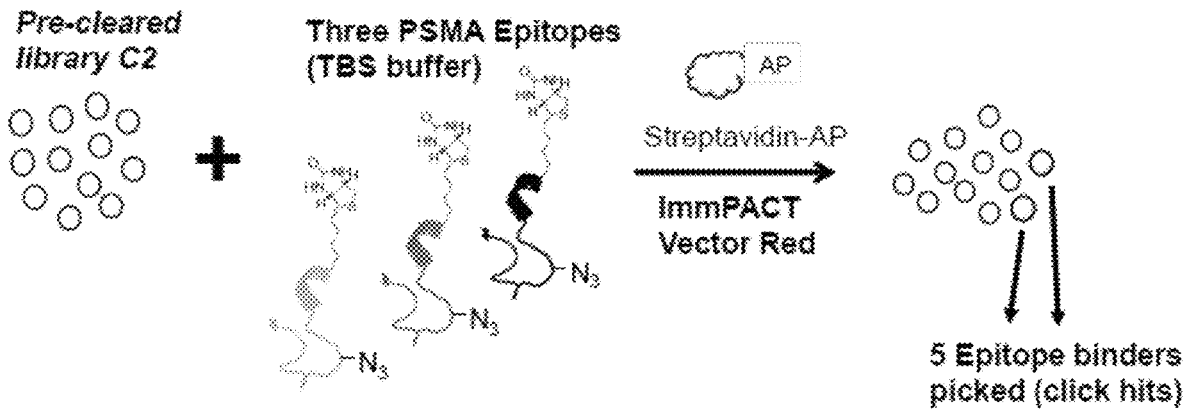
FIGS. 11A and 11B are diagrams showing an example of multi-ligand screening using epitopes 2A/2B, 6, and 7.
Figure 11B:
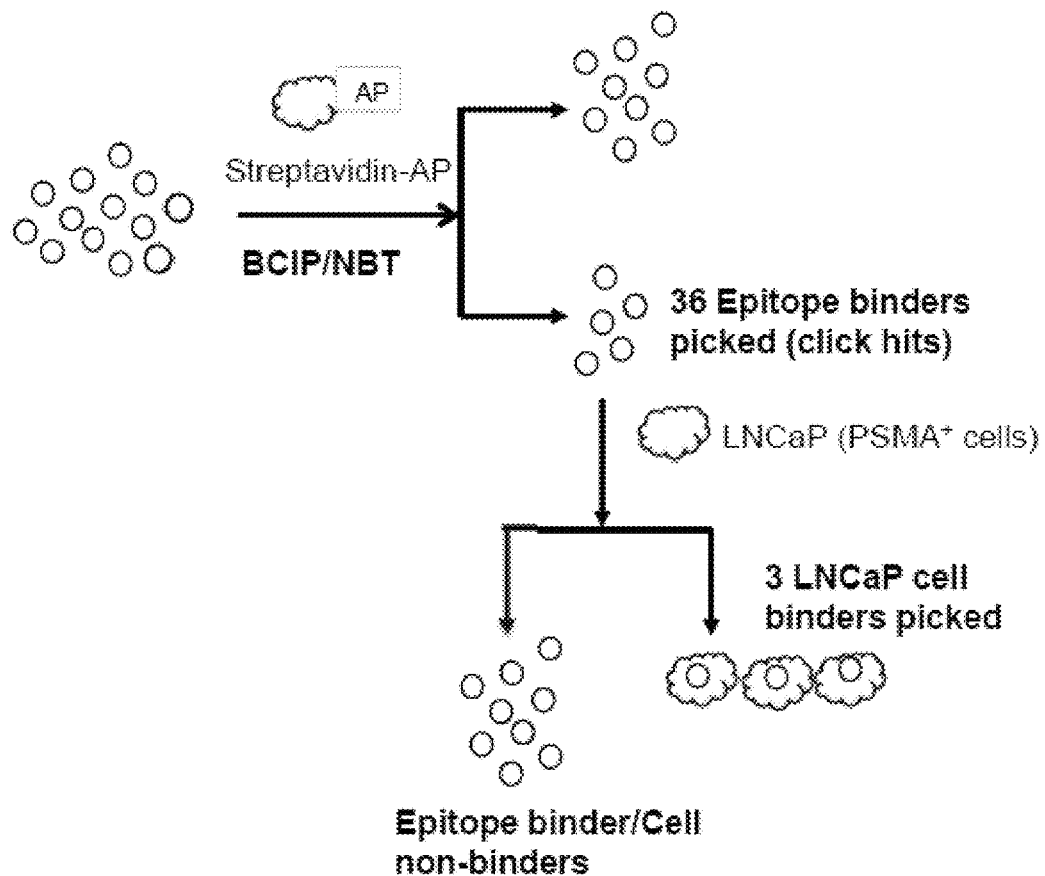
Figure 12:
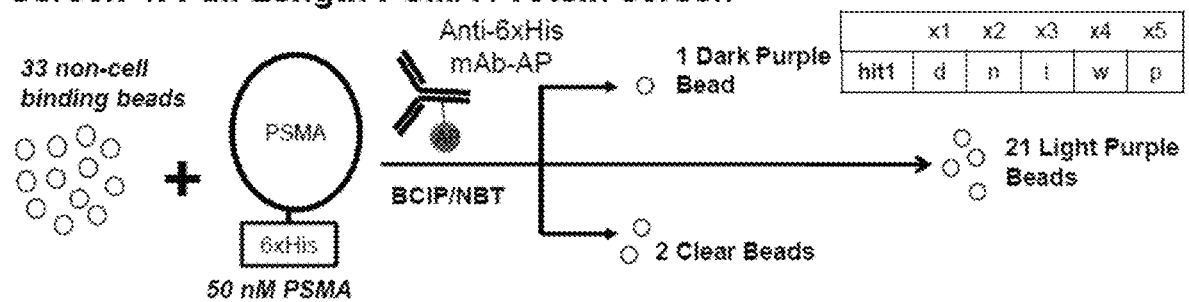
FIG. 12 is a diagram of the fourth screening a 33 non-cell binding beads to PSMA protein. The dark purple bead has the sequence dntwp (SEQ ID NO:26).

To increase the throughput of the screening step, three epitopes were mixed and screened against the pre-cleared library. PSMA epitopes 2C, 6, and 7 were mixed and picked by either an ImmPACT Vector Red or BCIP/NBT dye (FIG. 11). The ImmPACT Vector Red screen identified the hit peptide ehtye (SEQ ID NO:22). A further screen was undertaken to test the ability of LNCaP cells (a PSMA+ cell line) to bind to these hits (FIG. 11B. LNCaP cells demonstrated good adherence to three beads (Table 8; dwpve (SEQ ID NO:23); kwtsd (SEQ ID NO:24); svand (SEQ ID NO:25)) and were non- or poorly adherent to 33 beads. Following sequencing of the hit beads, it was discovered that negatively-charged amino acids dominated the 5th position. Re-synthesis of these hits provided the opportunity to test the compounds in ELISA and flow. Binding to recombinant PSMA protein was achieved by ehtye (SEQ ID NO:22) and svand (SEQ ID NO:25), with good selectivity over an unrelated protein (CD8). In flow, binding to LNCaPs was modest for the case of svand (SEQ ID NO:25). svand (SEQ ID NO:25) shows the same binding to both PSMA+ and PSMA− cells; ehtye (SEQ ID NO:22) shows increased binding to PSMA− cells; and dwpve (SEQ ID NO:23), kwtsd (SEQ ID NO:24), and dntwp (SEQ ID NO:26) show no binding by ELISA or flow. Further epitope selectivity can be deconvoluted via a single epitope orientation assay.

TABLE 8

|  | x1 | x2 | x3 | x4 | x5 |
|---|---|---|---|---|---|
| hit1 | d | w | p | v | e |
| hit2 | k | w | t | s | d |
| hit3 | s | v | a | n | d |

The 33 beads that did not bind to LNCaP cells were incubated with 50 nM full length PSMA protein. Some beads were lost during this screen. Most beads turned purple. There was one bead that was darker than the others. That one bead was sequenced and was revealed to be dntwp (SEQ ID NO:26). The 21 light purple beads were sequenced (sequences shown in Table 9). These will be evaluated further by calculating their binding affinities by docking against the screened epitopes 2C, 6, and 7. Clustering analysis was used to identify some interesting sequences. Sequences found in the periphery (pkvrd (SEQ ID NO:27), frvkd (SEQ ID NO:28), dyksk (SEQ ID NO:32), Grkpf (SEQ ID NO:35), kwndd (SEQ ID NO:36), tkGne (SEQ ID NO:39), kvetd (SEQ ID NO:41), neGfd (SEQ ID NO:42), ekfld (SEQ ID NO:43), dkkaw (SEQ ID NO:44), veyGn (SEQ ID NO:45)) are generally preferred because they are more interesting chemically.

TABLE 9

|  | x1 | x2 | x3 | x4 | x5 |  |
|---|---|---|---|---|---|---|
| hit1 | p | k | v | r | d | SEQ ID NO: 27 |
| hit2 | f | r | v | k | d | SEQ ID NO: 28 |
| hit3 | l | y | n | r | e | SEQ ID NO: 29 |
| hit4 | G | y | d | f | p | SEQ ID NO: 30 |
| hit5 | s | f | k | y | k | SEQ ID NO: 31 |
| hit6 | d | y | k | s | k | SEQ ID NO: 32 |
| hit7 |  | w | k | s | l | SEQ ID NO: 33 |
| hit8 | r | k | a | t | p | SEQ ID NO: 34 |
| hit9 | G | r | k | p | f | SEQ ID NO: 35 |
| hit10 | k | w | n | d | d | SEQ ID NO: 36 |
| hit11 |  | e | l | d | d | SEQ ID NO: 37 |
| hit12 | a | n | G | s | w | SEQ ID NO: 38 |
| hit13 | t | k | G | n | e | SEQ ID NO: 39 |
| hit14 | p | l | n | t | d | SEQ ID NO: 40 |
| hit15 | k | v | e | t | d | SEQ ID NO: 41 |
| hit16 | n | e | G | f | d | SEQ ID NO: 42 |
| hit17 | e | k | f | l | d | SEQ ID NO: 43 |
| hit18 | d | k | k | a | w | SEQ ID NO: 44 |
| hit19 | v | e | y | G | n | SEQ ID NO: 45 |
| hit20 | e | y | p | r | h | SEQ ID NO: 46 |

Additional PSMA epitopes were identified through analysis of the PSMA structure and the chemical properties of different portions of PSMA. For example, computations based on the X-ray structure of PSMA were used to identify portions of the protein that are predicted to have surface exposure, which portions of the protein are predicted to antigenic, and portions that combine surface exposure and antigenicity. These identifications were used to generate a sliding window analysis using a 14 amino acid epitope window to predict the surface exposure and antigenicity of the 14-mer epitopes. The new epitopes were selected as regions of PSMA having both high surface exposure (>85%) and high predicted antigenicity (100%). The new epitopes are amino acids 43-56 of PSMA (IKSSNEATNITPKH; amino acids 43-56 of SEQ ID NO:51), amino acids 143-156 of PSMA (LFEPPPPGYENVSD; amino acids 143-156 of SEQ ID NO:51), amino acids 181-194 of PSMA (TEDFFKLERDMKIN; amino acids 181-194 of SEQ ID NO:51), and amino acids 499-512 of PSMA (KKSPSPE-FSGMPRI; amino acids 499-512 of SEQ ID NO:51). The 43-56 epitope and the 143-156 epitope have glycosylation sites at N51 and n153, respectively. These can be used as the modification site for the click chemistry handle or, alternatively, avoided as the modification site for the click chemistry handle.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular forms and embodiments only and is not intended to be limiting.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

It is understood that the disclosed method and compositions are not limited to the particular methodology, protocols, and reagents described as these may vary. It is also to be understood that the terminology used herein is for the purpose of describing particular forms and embodiments only, and is not intended to limit the scope of the present invention which will be limited only by the appended claims.

Throughout this specification the word "comprise," or variations such as "comprises" or "comprising," will be understood to imply the inclusion of a stated element, integer or step, or group of elements, integers or steps, but not the exclusion of any other element, integer or step, or group of elements, integers or steps.

Reference throughout this specification to "some embodiments," "one embodiment," or "an embodiment" means that a particular feature, structure or characteristic described in connection with the embodiment(s) is included in at least one embodiment of the disclosed subject matter. Thus, the appearances of the phrases "in some embodiments," "in one embodiment," or "in an embodiment" in various places throughout this specification are not necessarily all referring to the same embodiment(s). Furthermore, the particular features, structures, or characteristics can be combined in any suitable manner in one or more embodiments.

Reference throughout this specification to "some forms," "one form," or "a form" means that a particular feature, structure or characteristic described in connection with the form(s) is included in at least one form of the disclosed subject matter. Thus, the appearances of the phrases "in some forms," "in one form," or "in a form" in various places throughout this specification are not necessarily all referring to the same form(s). Furthermore, the particular features, structures, or characteristics can be combined in any suitable manner in one or more forms.

It must be noted that as used herein and in the appended claims, the singular forms "a", "an", and "the" include plural reference unless the context clearly dictates otherwise. Thus, for example, reference to "a capture agent" includes a plurality of such capture agents, reference to "the capture agents" is a reference to one or more capture agents and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Unless the context clearly indicates otherwise, use of the word "can" indicates an option or capability of the object or condition referred to. Generally, use of "can" in this way is meant to positively state the option or capability while also leaving open that the option or capability could be absent in other forms or embodiments of the object or condition referred to. Unless the context clearly indicates otherwise, use of the word "may" indicates an option or capability of the object or condition referred to. Generally, use of "may" in this way is meant to positively state the option or capability while also leaving open that the option or capability could be absent in other forms or embodiments of the object or condition referred to. Unless the context clearly indicates otherwise, use of "may" herein does not refer to an unknown or doubtful feature of an object or condition.

Ranges can be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated form or embodiment that should be considered disclosed unless the context specifically indicates otherwise. It will be further understood that the endpoints of each of the ranges are significant both in relation to the other endpoint, and independently of the other endpoint unless the context specifically indicates otherwise. It should be understood that all of the individual values and sub-ranges of values contained within an explicitly disclosed range are also specifically contemplated and should be considered disclosed unless the context specifically indicates otherwise. Finally, it should be understood that all ranges refer both to the recited range as a range and as a collection of individual numbers from and including the first endpoint to and including the second endpoint. In the latter case, it should be understood that any of the individual numbers can be selected as one form of the quantity, value, or feature to which the range refers. In this way, a range describes a set of numbers or values from and including the first endpoint to and including the second endpoint from which a single member of the set (i.e. a single number) can be selected as the quantity, value, or feature to which the range refers. The foregoing applies regardless of whether in particular cases some or all of these forms and embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. may include numerous options and alternatives, this should not be construed as, and is not an admission that, such options and alternatives are equivalent to each other or, in particular, are obvious alternatives. Thus, for example, a list of different ligands does not indicate that the listed ligands are obvious one to the other, nor is it an admission of equivalence or obviousness.

Every ligand or capture agent disclosed herein is intended to be and should be considered to be specifically disclosed herein. Further, every subgroup that can be identified within this disclosure is intended to be and should be considered to be specifically disclosed herein. As a result, it is specifically contemplated that any ligand or capture agent, or subgroup of ligands or capture agents can be either specifically included for or excluded from use or included in or excluded from a list of ligands or capture agents.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a capture agent is disclosed and discussed and a number of modifications that can be made to a number of molecules including the capture agent are discussed, each and every combination and permutation of capture agent and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific for or embodiment or combination of forms and/or embodiments of the disclosed methods, and that each such combination is specifically contemplated and should be considered disclosed.

Those skilled in the art will recognize, or be able to ascertain many equivalents to the specific forms and embodiments of the method and compositions described herein. Such equivalents are intended to be encompassed by the following claims.

We claim:

1. A theranostic capture agent for a target, the capture agent comprising two or more ligands covalently linked to each other, wherein the ligands specifically bind to one of two or more distinct epitopes of a target that are in different locations on the target, wherein the capture agent (a) is a precursor that can be loaded with a detectable moiety, a therapeutic moiety, or both, (b) further comprises a detectable moiety, (c) further comprises a therapeutic moiety, or (d) further comprises both a detectable moiety and a therapeutic moiety, wherein the ligand comprises an amino acid sequence 80-100% identical to an amino acid sequence selected from the group consisting of revry (SEQ ID NO:3), hreww (SEQ ID NO:10), rdlhw (SEQ ID NO:4), drlhw (SEQ ID NO:5), ert, lpwtr (SEQ ID NO:6), tfnkn (SEQ ID NO:7), wlsGk (SEQ ID NO:8), srdwp (SEQ ID NO:9), lfkhh (SEQ ID NO:16), fGyvd (SEQ ID NO:17), ernta (SEQ ID NO:18), hnwlG (SEQ ID NO:19), wende (SEQ ID NO:20), lnhGt (SEQ ID NO:21), ehtye (SEQ ID NO:22), dwpve (SEQ ID NO:23), kwtsd (SEQ ID NO:24), svand (SEQ ID NO:25), dntwp (SEQ ID NO:26), pkvrd (SEQ ID NO:27), frvkd (SEQ ID NO:28), lynre (SEQ ID NO:29), Gydfp (SEQ ID NO:30), sfkyk (SEQ ID NO:31), dyksk (SEQ ID NO:32), wksl (SEQ ID NO:33), rkatp (SEQ ID NO:34), Grkpf (SEQ ID NO:35), kwndd (SEQ ID NO:36), eldd (SEQ ID NO:37), anGsw (SEQ ID NO:38), tkGne (SEQ ID NO:39), pintd (SEQ ID NO:40), kvetd (SEQ ID NO:41), neGfd (SEQ ID NO:42), ekfld (SEQ ID NO:43), dkkaw (SEQ ID NO:44), veyGn (SEQ ID NO:45), and eyprh (SEQ ID NO:46).

2. The capture agent of claim 1, wherein the capture agent comprises a first of the ligands that has affinity for a first of the epitopes, a second of the ligands that has affinity for a second of the epitopes, and a linker covalently connecting the first ligand to the second ligand.

3. The capture agent of claim 2, wherein the capture agent further comprises a loading moiety that (i) can be loaded with a detectable moiety, a therapeutic moiety, or both, or (ii) further comprises a detectable moiety, a therapeutic moiety, or both.

4. The capture agent of claim 3, wherein the loading moiety is DOTA or NOTA.

5. The capture agent of claim 3, wherein the loading moiety is (a) unloaded, (b) further comprises a detectable moiety, (c) further comprises a therapeutic moiety, or (d) further comprises both a detectable moiety and a therapeutic moiety.

6. The capture agent of claim 3, wherein the loading moiety further comprises a detectable moiety.

7. The capture agent of claim 3, wherein the capture agent further comprises a detectable moiety.

8. The capture agent of claim 1, further comprising a detectable moiety, wherein the detectable moiety is selected from the group consisting of biotin, copper, biotin-PEG3, aminooxyacetate, $^{19}$FB, $^{18}$FB and FITC-PEG$_3$.

9. The capture agent of claim 6, wherein the detectable moiety is selected from the group consisting of Al$^{18}$F, $^{18}$F, $^{68}$Ga, $^{64}$Cu, $^{68}$Ga, $^{89}$Zr, $^{124}$I, $^{86}$Y, $^{94m}$Tc, $^{110m}$In, $^{11}$C, and $^{76}$Br.

10. The capture agent of claim 3, wherein the loading moiety further comprises a therapeutic moiety.

11. The capture agent of claim 1, wherein the capture agent further comprises a therapeutic moiety.

12. The capture agent of claim 1, wherein the therapeutic moiety is selected from the group consisting of $^{177}$Lu, $^{99m}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{198}$Au and $^{199}$Au.

13. The capture agent of claim 11, wherein the therapeutic moiety is selected from the group consisting of $^{177}$Lu, $^{99m}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{198}$Au and $^{199}$Au.

14. The capture agent of claim 1, wherein the capture agent binds PSMA.

15. The capture agent of claim 14, wherein the first epitope is an epitope on PSMA, wherein the first ligand has affinity for the epitope on PSMA.

16. The capture agent of claim 14, wherein the second epitope is an epitope on PSMA, wherein the second ligand has affinity for the epitope on PSMA.

17. The capture agent of claim 14, wherein the capture agent specifically binds PSMA.

18. The capture agent of claim 14, wherein the first epitope comprises the amino acid sequence RTEDFFKLER-DMK (SEQ ID NO:2), EYAYRRGIAEAVGLPSI (SEQ ID NO:1), TKKSPSPEFSGMP (SEQ ID NO:11), TKKSPSPE-FSGMPRISKLG (SEQ ID NO:12), YTKNWETNKFSG (SEQ ID NO:13), PADYFAPGVKSYPDGWNLPG (SEQ ID NO:14), or GSAPPDSSWRGSLKVPYNVGPGF (SEQ ID NO:15).

19. The capture agent of claim 14, wherein the first ligand comprises an amino acid sequence 80-100% identical to an amino acid sequence selected from the group consisting of revry (SEQ ID NO:3), hreww (SEQ ID NO:10), rdlhw (SEQ ID NO:4), drlhw (SEQ ID NO:5), ert, 1pwtr (SEQ ID NO:6), tfnkn (SEQ ID NO:7), wlsGk (SEQ ID NO:8), srdwp (SEQ ID NO:9), lfkhh (SEQ ID NO:16), fGyvd (SEQ ID NO:17), ernta (SEQ ID NO:18), hnwlG (SEQ ID NO:19), wende (SEQ ID NO:20), lnhGt (SEQ ID NO:21), ehtye (SEQ ID NO:22), dwpve (SEQ ID NO:23), kwtsd (SEQ ID NO:24), svand (SEQ ID NO:25), and dntwp (SEQ ID NO:26).

20. The capture agent of claim 14, wherein the first ligand comprises an amino acid sequence 80-100% identical to an amino acid sequence selected from the group consisting of pkvrd (SEQ ID NO:27), frvkd (SEQ ID NO:28), lynre (SEQ ID NO:29), Gydfp (SEQ ID NO:30), sfkyk (SEQ ID NO:31), dyksk (SEQ ID NO:32), wksl (SEQ ID NO:33), rkatp (SEQ ID NO:34), Grkpf (SEQ ID NO:35), kwndd (SEQ ID NO:36), eldd (SEQ ID NO:37), anGsw (SEQ ID NO:38), tkGne (SEQ ID NO:39), pintd (SEQ ID NO:40), kvetd (SEQ ID NO:41), neGfd (SEQ ID NO:42), ekfld (SEQ ID NO:43), dkkaw (SEQ ID NO:44), veyGn (SEQ ID NO:45), and eyprh (SEQ ID NO:46).

21. The capture agent of claim 14, wherein the first ligand comprises an amino acid sequence selected from the group consisting of revry (SEQ ID NO:3), hreww (SEQ ID NO:10), rdlhw (SEQ ID NO:4), drlhw (SEQ ID NO:5), ert, lpwtr (SEQ ID NO:6), tfnkn (SEQ ID NO:7), wlsGk (SEQ ID NO:8), srdwp (SEQ ID NO:9), lfkhh (SEQ ID NO:16), fGyvd (SEQ ID NO:17), ernta (SEQ ID NO:18), hnwlG (SEQ ID NO:19), wende (SEQ ID NO:20), lnhGt (SEQ ID NO:21), ehtye (SEQ ID NO:22), dwpve (SEQ ID NO:23), kwtsd (SEQ ID NO:24), svand (SEQ ID NO:25), and dntwp (SEQ ID NO:26).

22. The capture agent of claim 14, wherein the first ligand comprises an amino acid sequence selected from the group consisting of pkvrd (SEQ ID NO:27), frvkd (SEQ ID NO:28), lynre (SEQ ID NO:29), Gydfp (SEQ ID NO:30), sfkyk (SEQ ID NO:31), dyksk (SEQ ID NO:32), wksl (SEQ ID NO:33), rkatp (SEQ ID NO:34), Grkpf (SEQ ID NO:35), kwndd (SEQ ID NO:36), eldd (SEQ ID NO:37), anGsw (SEQ ID NO:38), tkGne (SEQ ID NO:39), pintd (SEQ ID NO:40), kvetd (SEQ ID NO:41), neGfd (SEQ ID NO:42), ekfld (SEQ ID NO:43), dkkaw (SEQ ID NO:44), veyGn (SEQ ID NO:45), and eyprh (SEQ ID NO:46).

23. The capture agent of claim 15, wherein the first ligand comprises the structure

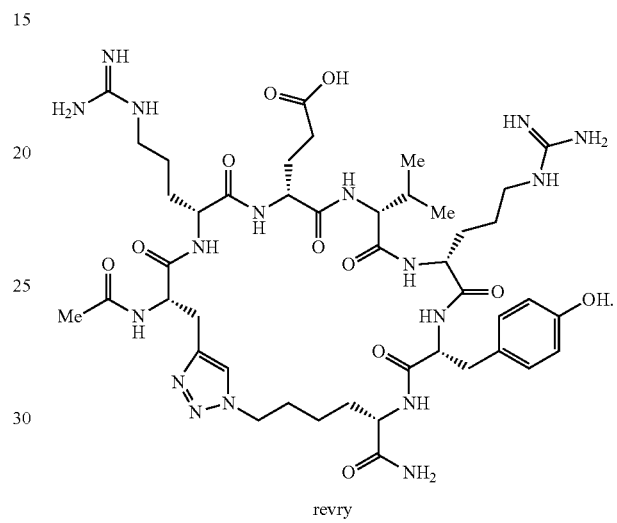

revry

24. The capture agent of claim 15, wherein the first ligand comprises the structure

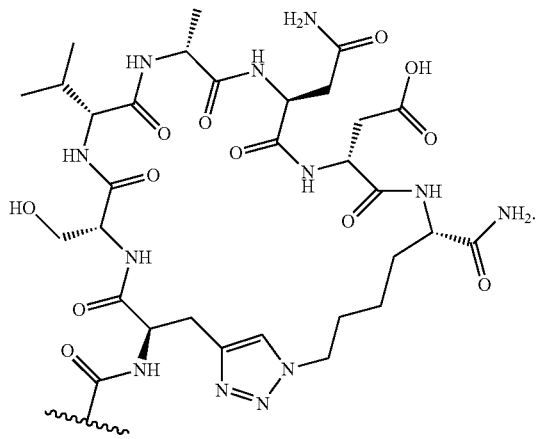 [SMILES: *C(=O)N[C@@H]1Cc2cn(nn2)CCCC[C@@H](C(N)=O)NC(=O)[C@@H](CC(=O)O)NC(=O)[C@H](CC(N)=O)NC(=O)[C@@H](C)NC(=O)[C@@H](C(C)C)NC(=O)[C@@H](CO)NC1=O]

25. The capture agent of claim 15, wherein the second epitope comprises the amino acid sequence EYAYRRGI-AEAVGLPSI (SEQ ID NO:1).

26. The capture agent of claim 25, wherein the second ligand comprises an amino acid sequence 80-100% identical to an amino acid sequence selected from the group consisting of lpwtr (SEQ ID NO:6), hnwlG (SEQ ID NO:19), wende (SEQ ID NO:20), and lnhGt (SEQ ID NO:21).

27. The capture agent of claim 25, wherein the second ligand comprises an amino acid sequence selected from the group consisting of lpwtr (SEQ ID NO:6), hnwlG (SEQ ID NO:19), wende (SEQ ID NO:20), and lnhGt (SEQ ID NO:21).

28. The capture agent of claim 15, wherein the second epitope comprises the amino acid sequence TKKSPSPE-FSGMP (SEQ ID NO:11).

29. The capture agent of claim 28, wherein the second ligand comprises an amino acid sequence 80-100% identical to an amino acid sequence selected from the group consisting of revry (SEQ ID NO:3), rdlhw (SEQ ID NO:4), drlhw (SEQ ID NO:5), and ert.

30. The capture agent of claim 28, wherein the second ligand comprises an amino acid sequence selected from the group consisting of revry (SEQ ID NO:3), rdlhw (SEQ ID NO:4), drlhw (SEQ ID NO:5), and ert.

31. The capture agent of claim 15, wherein the second epitope comprises the amino acid sequence YTKNWETNKFSG (SEQ ID NO:13).

32. The capture agent of claim 31, wherein the second ligand comprises an amino acid sequence 80-100% identical to an amino acid sequence selected from the group consisting of lfkhh (SEQ ID NO:16), fGyvd (SEQ ID NO:17), and ernta (SEQ ID NO:18).

33. The capture agent of claim 31, wherein the second ligand comprises an amino acid sequence selected from the group consisting of lfkhh (SEQ ID NO:16), fGyvd (SEQ ID NO:17), and ernta (SEQ ID NO:18).

34. The capture agent of claim 15, wherein the second epitope comprises the amino acid sequence RTEDFFKLER-DMK (SEQ ID NO:2).

35. The capture agent of claim 34, wherein the second ligand comprises an amino acid sequence 80-100% identical to an amino acid sequence selected from the group consisting of hreww (SEQ ID NO:10), tfnkn (SEQ ID NO:7), wlsGk (SEQ ID NO:8), and srdwp (SEQ ID NO:9).

36. The capture agent of claim 34, wherein the second ligand comprises an amino acid sequence selected from the group consisting of hreww (SEQ ID NO:10), tfnkn (SEQ ID NO:7), wlsGk (SEQ ID NO:8), and srdwp (SEQ ID NO:9).

37. The capture agent of claim 15, wherein the second epitope comprises the amino acid sequence TKKSPSPE-FSGMPRISKLG (SEQ ID NO:12), PADYFAPGVKSYPDGWNLPG (SEQ ID NO:14), or GSAPPDSSWRGSLKVPYNVGPGF (SEQ ID NO:15).

38. The capture agent of claim 37, wherein the second ligand comprises an amino acid sequence 80-100% identical to an amino acid sequence selected from the group consisting of ehtye (SEQ ID NO:22), dwpve (SEQ ID NO:23), kwtsd (SEQ ID NO:24), svand (SEQ ID NO:25), and dntwp (SEQ ID NO:26).

39. The capture agent of claim 37, wherein the second ligand comprises an amino acid sequence selected from the group consisting of ehtye (SEQ ID NO:22), dwpve (SEQ ID NO:23), kwtsd (SEQ ID NO:24), svand (SEQ ID NO:25), and dntwp (SEQ ID NO:26).

40. The capture agent of claim 15, wherein the second epitope comprises the amino acid sequence TKKSPSPE-FSGMPRISKLG (SEQ ID NO:12).

41. The capture agent of claim 15, wherein the second epitope comprises the amino acid sequence PADYFAPGVKSYPDGWNLPG (SEQ ID NO:14).

42. The capture agent of claim 15, wherein the second epitope comprises the amino acid sequence GSAPPDSS-WRGSLKVPYNVGPGF (SEQ ID NO:15).

43. The capture agent of claim 2, wherein the first ligand is cyclic.

44. The capture agent of claim 2, wherein the first ligand comprises a 1,4-substituted-1,2,3-triazole residue (Tz4) or a 1,5-substituted-1,2,3-triazole residue (Tz5).

45. The capture agent of claim 44, wherein the first ligand comprises a 1,4-substituted-1,2,3-triazole residue (Tz4).

46. The capture agent of claim 44, wherein the first ligand comprises a 1,5-substituted-1,2,3-triazole residue (Tz5).

47. The capture agent of claim 2, wherein the second ligand is cyclic.

48. The capture agent of claim 2, wherein the second ligand comprises a 1,4-substituted-1,2,3-triazole residue (Tz4) or a 1,5-substituted-1,2,3-triazole residue (Tz5).

49. The capture agent of claim 48, wherein the second ligand comprises a 1,4-substituted-1,2,3-triazole residue (Tz4).

50. The capture agent of claim 48, wherein the second ligand comprises a 1,5-substituted-1,2,3-triazole residue (Tz5).

51. The capture agent of claim 2, wherein the linker is divalent.

52. The capture agent of claim 2, wherein the length of the linker corresponds to distance between the first epitope and the second epitope.

53. The capture agent of claim 2, wherein the length of the linker is from ~4.4 Å to ~26.4 Å, from ~8.8 Å to ~26.4 Å or from ~7 Å to ~15 Å.

54. The capture agent of claim 2, wherein the length of the linker is ~15 Å.

55. The capture agent of claim 2, wherein the linker comprises one or more repeat units of ethylene glycol.

56. The capture agent of claim 55, wherein the linker is selected from the group consisting of $PEG_1$, $PEG_2$, $PEG_3$, $PEG_4$ and PEGS.

57. The capture agent of claim 2, wherein the linker comprises a peptide.

58. The capture agent of claim 57, wherein the linker is glycine.

59. A method for detecting PSMA in a biological sample, the method comprising:
(a) contacting the biological sample with one or more capture agents of claim 1 to allow PSMA in the biological sample to bind the capture agents, wherein each of the capture agents is linked to a detectable moiety; and
(b) detecting the detectable moiety of capture agents that bind to PSMA in (a), wherein the detection of the detectable moiety indicates the presence of PSMA in the biological sample.

60. The method of claim 59, wherein PSMA is detected via an immunoassay selected from the group comprising a western blot, pull-down assay, dot blot, and ELISA.

61. A method for detecting PSMA in a subject, the method comprising:
(a) administering one or more capture agents of claim 1 to the subject, wherein each capture agent is linked to a detectable moiety; and
(b) detecting the detectable moiety linked to the one or more capture agents in the subject, wherein detection of the detectable moiety indicates the presence of PSMA in the subject.

62. The method of claim 61, wherein at least one of the capture agents specifically binds PSMA.

63. The method of claim 61, wherein PSMA is detected via diagnostic imaging selected from the group comprising Magnetic Resonance Imaging (MRI), x-ray, Positron Emission Tomography (PET), Single Photon Emission Computed Tomography (SPECT) and scintigraphic imaging.

64. A method for treating a subject in need thereof, the method comprising the step of administering one or more capture agents of claim 1 to the subject, wherein the subject has a disease or condition that is characterized by PSMA overexpression, wherein the disease or condition is cancer.

65. The method of claim 64, wherein at least one of the capture agents specifically binds PSMA.

66. The method of claim 64, wherein one or more of the capture agents further comprise a therapeutic moiety.

67. The method of claim 66, wherein one or more of the one or more capture agents further comprises a detectable moiety.

68. The method of claim 66, wherein one or more of the one or more capture agents loaded with the therapeutic moiety are also loaded with a detectable moiety.

69. The method of claim 66 further comprising administering one or more additional capture agents to the subject, wherein one or more of the one or more additional capture agents are loaded with a detectable moiety.

70. The method of claim 69, wherein one or more of the one or more additional capture agents are administered at or near the same time as, or together with, one or more of the capture agents are administered.

71. The method of claim 69, wherein one or more of the one or more additional capture agents are administered at a different time than one or more of the capture agents are administered.

\* \* \* \* \*

SEQUENCE LISTING

```
<160> NUMBER OF SEQ ID NOS: 51

<210> SEQ ID NO 1
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 1

Glu Tyr Ala Tyr Arg Arg Gly Ile Ala Glu Ala Val Gly Leu Pro Ser
1               5                   10                  15

Ile

<210> SEQ ID NO 2
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 2

Arg Thr Glu Asp Phe Phe Lys Leu Glu Arg Asp Met Lys
1               5                   10

<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MISC_FEATURE
<222> LOCATION: (1)..(5)
<223> OTHER INFORMATION: D amino acids

<400> SEQUENCE: 3

Arg Glu Val Arg Tyr
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 4

Arg Asp Leu His Trp
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 5

Asp Arg Leu His Trp
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 6

Leu Pro Trp Thr Arg
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 7

Thr Phe Asn Lys Asn
1               5

<210> SEQ ID NO 8
```

```
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(3)
<223> OTHER INFORMATION: D amino acids
<220> FEATURE:
<221> NAME/KEY: MISC_FEATURE
<222> LOCATION: (5)..(5)
<223> OTHER INFORMATION: D amino acid

<400> SEQUENCE: 8

Trp Leu Ser Gly Lys
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 9

Ser Arg Asp Trp Pro
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 10

His Arg Glu Trp Trp
1               5

<210> SEQ ID NO 11
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 11

Thr Lys Lys Ser Pro Ser Pro Glu Phe Ser Gly Met Pro
1               5                   10

<210> SEQ ID NO 12
<211> LENGTH: 19
<212> TYPE: PRT
<213> ORGANISM: Artificial Sequence
<220> FEATURE:
<223> OTHER INFORMATION: Synthetic Peptide
```

```
<400> SEQUENCE: 12

Thr Lys Lys Ser Pro Ser Pro Glu Phe Ser Gly Met Pro Arg Ile Ser
1               5                   10                  15

Lys Leu Gly

<210> SEQ ID NO 13
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 13

Tyr Thr Lys Asn Trp Glu Thr Asn Lys Phe Ser Gly
1               5                   10

<210> SEQ ID NO 14
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 14

Pro Ala Asp Tyr Phe Ala Pro Gly Val Lys Ser Tyr Pro Asp Gly Trp
1               5                   10                  15

Asn Leu Pro Gly
            20

<210> SEQ ID NO 15
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 15

Gly Ser Ala Pro Pro Asp Ser Ser Trp Arg Gly Ser Leu Lys Val Pro
1               5                   10                  15

Tyr Asn Val Gly Pro Gly Phe
            20

<210> SEQ ID NO 16
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 16

Leu Phe Lys His His
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
```

```
<222> LOCATION: (1)..(1)
<223> OTHER INFORMATION: D amino acid
<220> FEATURE:
<221> NAME/KEY: MISC_FEATURE
<222> LOCATION: (3)..(5)
<223> OTHER INFORMATION: D amino acids

<400> SEQUENCE: 17

Phe Gly Tyr Val Asp
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 18

Glu Arg Asn Thr Ala
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(4)
<223> OTHER INFORMATION: D amino acids

<400> SEQUENCE: 19

His Asn Trp Leu Gly
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 20

Trp Glu Asn Asp Glu
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(3)
<223> OTHER INFORMATION: D amino acids
<220> FEATURE:
<221> NAME/KEY: MISC_FEATURE
<222> LOCATION: (5)..(5)
<223> OTHER INFORMATION: D amino acid
```

```
<400> SEQUENCE: 21

Leu Asn His Gly Thr
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 22

Glu His Thr Tyr Glu
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 23

Asp Trp Pro Val Glu
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 24

Lys Trp Thr Ser Asp
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 25

Ser Val Ala Asn Asp
1               5

<210> SEQ ID NO 26
<211> LENGTH: 5
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 26

Asp Asn Thr Trp Pro
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: mis
<222> LOCATION: (1)..(5)
<223> OTHER INFORMATION: D amino acids

<400> SEQUENCE: 27

Pro Lys Val Arg Asp
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 28

Phe Arg Val Lys Asp
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 29

Leu Tyr Asn Arg Glu
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(5)
<223> OTHER INFORMATION: D amino acids

<400> SEQUENCE: 30

Gly Tyr Asp Phe Pro
1               5
```

```
<210> SEQ ID NO 31
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 31

Ser Phe Lys Tyr Lys
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 32

Asp Tyr Lys Ser Lys
1               5

<210> SEQ ID NO 33
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(4)
<223> OTHER INFORMATION: D amino acids

<400> SEQUENCE: 33

Trp Lys Ser Leu
1

<210> SEQ ID NO 34
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 34

Arg Lys Ala Thr Pro
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(5)
<223> OTHER INFORMATION: D amino acids
```

```
<400> SEQUENCE: 35

Gly Arg Lys Pro Phe
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 36

Lys Trp Asn Asp Asp
1               5

<210> SEQ ID NO 37
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(4)
<223> OTHER INFORMATION: D amino acids

<400> SEQUENCE: 37

Glu Leu Asp Asp
1

<210> SEQ ID NO 38
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(2)
<223> OTHER INFORMATION: D amino acids
<220> FEATURE:
<221> NAME/KEY: MISC_FEATURE
<222> LOCATION: (4)..(5)
<223> OTHER INFORMATION: D amino acids

<400> SEQUENCE: 38

Ala Asn Gly Ser Trp
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(2)
<223> OTHER INFORMATION: D amino acids
<220> FEATURE:
<221> NAME/KEY: MISC_FEATURE
<222> LOCATION: (4)..(5)
<223> OTHER INFORMATION: D amino acids
```

```
<400> SEQUENCE: 39

Thr Lys Gly Asn Glu
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 40

Pro Leu Asn Thr Asp
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 41

Lys Val Glu Thr Asp
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(2)
<223> OTHER INFORMATION: D amino acids
<220> FEATURE:
<221> NAME/KEY: MISC_FEATURE
<222> LOCATION: (4)..(5)
<223> OTHER INFORMATION: D amino acids

<400> SEQUENCE: 42

Asn Glu Gly Phe Asp
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 43

Glu Lys Phe Leu Asp
1               5
```

```
<210> SEQ ID NO 44
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 44

Asp Lys Lys Ala Trp
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(3)
<223> OTHER INFORMATION: D amino acids
<220> FEATURE:
<221> NAME/KEY: MISC_FEATURE
<222> LOCATION: (5)..(5)
<223> OTHER INFORMATION: D amino acid

<400> SEQUENCE: 45

Val Glu Tyr Gly Asn
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: D amino acids

<400> SEQUENCE: 46

Glu Tyr Pro Arg His
1               5

<210> SEQ ID NO 47
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 47

Cys Pro Ala Asp Tyr Phe Ala Pro Gly Val Lys Ser Tyr Pro Asp Gly
1               5                   10                  15

Trp Asn Leu Pro Gly Cys
            20

<210> SEQ ID NO 48
<211> LENGTH: 25
<212> TYPE: PRT
<213> ORGANISM: Artificial Sequence
<220> FEATURE:
<223> OTHER INFORMATION: Synthetic Peptide
```

```
<400> SEQUENCE: 48

Cys Gly Ser Ala Pro Pro Asp Ser Ser Trp Arg Gly Ser Leu Lys Val
1               5                   10                  15

Pro Tyr Asn Val Gly Pro Gly Phe Cys
            20                  25

<210> SEQ ID NO 49
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 49

Gly Cys Pro Ala Asp Tyr Phe Ala Pro Gly Val Lys Ser Tyr Pro Asp
1               5                   10                  15

Gly Trp Asn Leu Pro Gly Cys Gly
            20

<210> SEQ ID NO 50
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 50

Gly Cys Gly Ser Ala Pro Pro Asp Ser Ser Trp Arg Gly Ser Leu Lys
1               5                   10                  15

Val Pro Tyr Asn Val Gly Pro Gly Phe Cys Gly
            20                  25

<210> SEQ ID NO 51
<211> LENGTH: 750
<212> TYPE: PRT
<213> ORGANISM: Artificial Sequence
<220> FEATURE:
<223> OTHER INFORMATION: Synthetic peptide

<400> SEQUENCE: 51

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140
```

```
Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
            165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
            195                 200                 205

Phe Arg Gly Asn Lys Val Lys Asn Ala Gln Leu Ala Gly Ala Lys Gly
            210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
            245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
            275                 280                 285

Leu Pro Ser Ile Pro Val His Pro Ile Gly Tyr Tyr Asp Ala Gln Lys
            290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
            325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
            355                 360                 365

Asp Arg Tyr Val Ile Leu Gly Gly His Arg Asp Ser Trp Val Phe Gly
            370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
            405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
            435                 440                 445

Tyr Ile Asn Ala Asp Ser Ser Ile Glu Gly Asn Tyr Thr Leu Arg Val
            450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
            485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
            530                 535                 540

Lys Phe Ser Gly Tyr Pro Leu Tyr His Ser Val Tyr Glu Thr Tyr Glu
545                 550                 555                 560
```

```
Leu Val Glu Lys Phe Tyr Asp Pro Met Phe Lys Tyr His Leu Thr Val
            565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
            595                 600                 605

Asp Lys Ile Tyr Ser Ile Ser Met Lys His Pro Gln Glu Met Lys Thr
            610                 615                 620

Tyr Ser Val Ser Phe Asp Ser Leu Phe Ser Ala Val Lys Asn Phe Thr
625             630                 635                 640

Glu Ile Ala Ser Lys Phe Ser Glu Arg Leu Gln Asp Phe Asp Lys Ser
            645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
            690                 695                 700

Phe Pro Gly Ile Tyr Asp Ala Leu Phe Asp Ile Glu Ser Lys Val Asp
705             710                 715                 720

Pro Ser Lys Ala Trp Gly Val Lys Arg Gln Ile Tyr Val Ala Ala
            725                 730                 735

Phe Thr Val Gln Ala Ala Ala Glu Thr Leu Ser Glu Val Ala
            740                 745                 750
```